(12) United States Patent
Soong

(10) Patent No.: US 10,857,156 B2
(45) Date of Patent: Dec. 8, 2020

(54) COMBINATION THERAPY OF TETRACYCLIC QUINOLONE ANALOGS FOR TREATING CANCER

(71) Applicant: Senhwa Biosciences, Inc., New Taipei (TW)

(72) Inventor: John Soong, Chino, CA (US)

(73) Assignee: SENHWA BIOSCIENCES, INC., New Taipei (TW)

( * ) Notice: Subject to any disclaimer, the term of this patent is extended or adjusted under 35 U.S.C. 154(b) by 0 days.

(21) Appl. No.: 15/347,656

(22) Filed: Nov. 9, 2016

(65) Prior Publication Data
US 2017/0143737 A1 May 25, 2017

Related U.S. Application Data

(60) Provisional application No. 62/258,211, filed on Nov. 20, 2015.

(51) Int. Cl.
| | | |
|---|---|---|
| *A61K 31/551* | (2006.01) | |
| *A61K 45/06* | (2006.01) | |
| *A61K 31/502* | (2006.01) | |
| *A61K 31/52* | (2006.01) | |
| *A61K 39/395* | (2006.01) | |
| *C07K 16/28* | (2006.01) | |

(52) U.S. Cl.
CPC .......... *A61K 31/551* (2013.01); *A61K 31/502* (2013.01); *A61K 31/52* (2013.01); *A61K 39/39558* (2013.01); *A61K 45/06* (2013.01); *C07K 16/2818* (2013.01); *C07K 2317/21* (2013.01); *C07K 2317/24* (2013.01)

(58) Field of Classification Search
CPC .................................................. A61K 31/551
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,703,055 A | 12/1997 | Felgner et al. |
| 7,179,805 B2 | 2/2007 | Grant, III et al. |
| 7,928,100 B2 | 4/2011 | Nagasawa et al. |
| 8,853,234 B2 | 10/2014 | Nagasawa et al. |
| 9,688,697 B2 | 6/2017 | Achiron et al. |
| 9,957,282 B2 | 5/2018 | Ryckman et al. |
| 2005/0227919 A1 | 10/2005 | Ashworth et al. |
| 2007/0099951 A1 | 5/2007 | Dube et al. |
| 2009/0093455 A1 | 4/2009 | Nagasawa et al. |
| 2009/0291437 A1 | 11/2009 | O'Brien et al. |
| 2010/0305136 A1 | 12/2010 | Nagasawa |
| 2011/0218184 A1 | 9/2011 | Nagasawa et al. |
| 2013/0274198 A1 | 10/2013 | Kufe et al. |
| 2014/0086839 A1 | 3/2014 | Achiron et al. |
| 2014/0113951 A1 | 4/2014 | Vincent et al. |
| 2014/0364434 A1 | 12/2014 | Daeman et al. |
| 2015/0125463 A1* | 5/2015 | Cogswell ........... C07K 16/2827 424/142.1 |
| 2019/0224209 A1 | 7/2019 | Soong |
| 2019/0374550 A1 | 12/2019 | Liu |

FOREIGN PATENT DOCUMENTS

| | | |
|---|---|---|
| EA | 201492105 | 6/2015 |
| JP | 2006-519827 A | 8/2006 |
| JP | 2007-537291 A | 12/2007 |
| JP | 2010-540663 A | 12/2010 |
| RU | 2404183 C2 | 11/2010 |
| WO | WO 2000/059882 | 10/2000 |
| WO | WO 2003/050107 | 6/2003 |

(Continued)

OTHER PUBLICATIONS

Supplementary European Search Report and Search Opinion for European Patent Application No. 08835342.0, dated Oct. 12, 2010, 6 pages.
International Search Report and Written Opinion for International Application No. PCT/US2008/078859, dated Dec. 24, 2008, 8 pages.
Office Action for U.S. Appl. No. 13/043,956, dated Nov. 6, 2013, 5 pages.
Office Action for U.S. Appl. No. 13/043,956, dated Dec. 12, 2011, 15 pages.
Office Action for U.S. Appl. No. 13/043,956, dated May 22, 2012, 12 pages.

(Continued)

*Primary Examiner* — Yong S. Chong
(74) *Attorney, Agent, or Firm* — Cooley LLP

(57) ABSTRACT

The present invention provides methods, compositions, and combinations for treating cancer via combined use of a compound of formula I or a pharmaceutically acceptable salt, ester, solvate and/or prodrug thereof, wherein A, Q, n, m, $R^7$, $R^8$, V, $X^1$, $X^2$, $X^3$, $X^4$, $X^5$, $X^6$, and $X^7$ are as defined herein, and at least one therapeutically active agents selected from immunotherapeutics, anticancer agents, and anti-angiogenics.

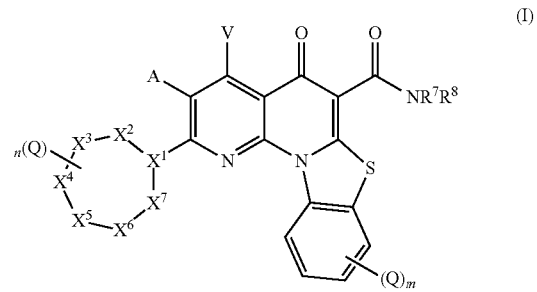

(I)

12 Claims, 20 Drawing Sheets

(56) References Cited

FOREIGN PATENT DOCUMENTS

Figure 1A:
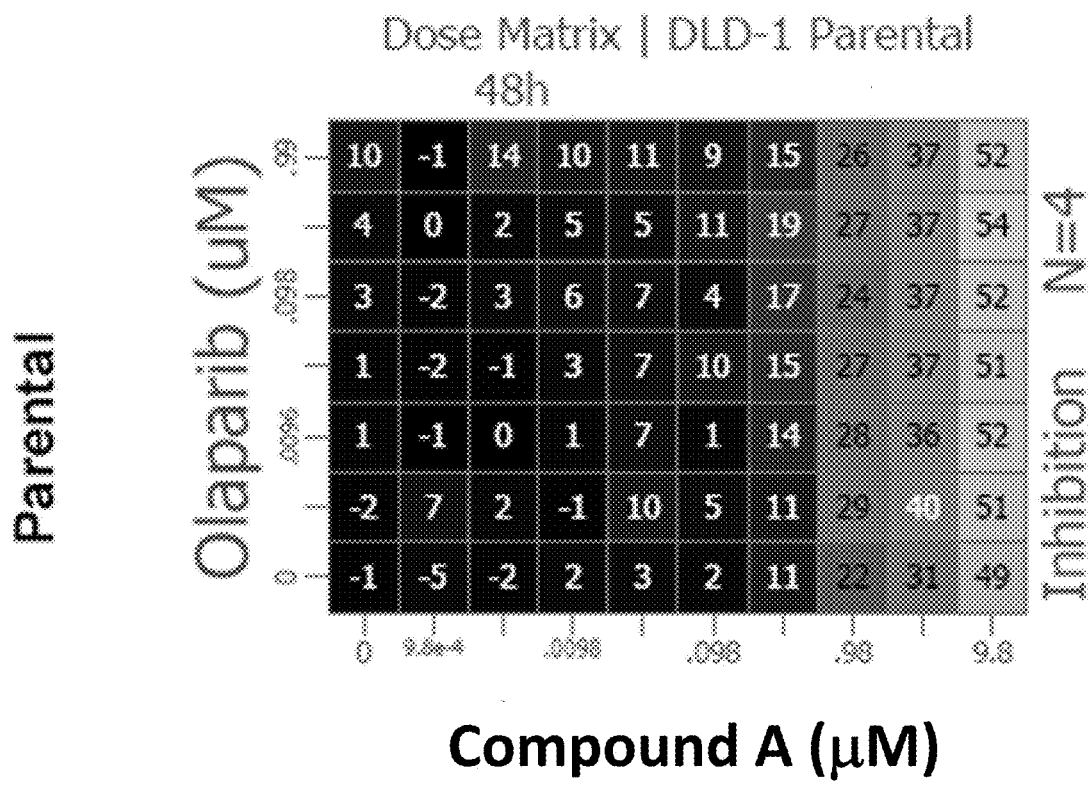

| WO | WO 2004/014893 | | 2/2004 |
|---|---|---|---|
| WO | WO 2004/080976 | A1 | 9/2004 |
| WO | WO-2005/012305 | | 2/2005 |
| WO | WO 2005/113556 | A1 | 12/2005 |
| WO | WO 2006/034113 | | 3/2006 |
| WO | WO 2007/019295 | | 2/2007 |
| WO | WO 2007/022474 | | 2/2007 |
| WO | WO 2007/056113 | | 5/2007 |
| WO | WO 2007/146813 | | 12/2007 |
| WO | WO 2007/146831 | | 12/2007 |
| WO | WO 2008/060693 | | 5/2008 |
| WO | WO 2008/092681 | | 8/2008 |
| WO | WO 2008/131134 | | 10/2008 |
| WO | WO 2009/046383 | | 4/2009 |
| WO | WO 2009/127414 | | 10/2009 |
| WO | WO 2012/123938 | | 9/2012 |
| WO | WO 2014/209804 | | 12/2014 |
| WO | WO 2015/079411 | | 6/2015 |
| WO | WO 2019/168688 | | 9/2019 |

OTHER PUBLICATIONS

Office Action for U.S. Appl. No. 14/967,574, dated Feb. 22, 2017, 5 pages.

International Search Report and Written Opinion for International Application No. PCT/US2015/065443, dated Oct. 4, 2016, 12 pages.

International Search Report and Written Opinion for International Application No. PCT/US2016/061176, dated Jan. 19, 2017, 10 pages.

Supplementary European Search Report and Search Opinion dated Jul. 22, 2009 based on European Patent Application No. 08731934.9, 10 pages.

Ansell, R.J. et al., "Molecularly imprinted polymers for bioanalysis: chromatography, binding assays and biomimetic sensors," Curr Opin Biotechnol 1996, 7:89-94.

Berge, S.M. et al., "Pharmaceutical Salts," J Pharm Sci 1977, 66:1-19.

Drygin, D. et al., "Targeting the nucleolus for cancer-specific activation of p53," Drug Discovery Today, Mar. 3, 2014, vol. 19, No. 3, pp. 259-265.

Gibson, U.E.M. et al., "A Novel Method for Real Time Quantitative RT-PCR," Genome Res 1996, 6:995-1001.

Heid, C.A. et al., "Real Time Quantitative PCR," Genome Res 1996, 6:986-994.

Jin, C.H. et al., "Human Vitamin D Receptor-Dependent Transactivation in *Saccharomyces cerevisiae* Requires Retinoid X Receptor," Mol Endocrinol 1996, 10:196-205.

Kriz, D. et al., "Introducing Biomimetic Sensors Based on Molecularly Imprinted Polymers as Recognition Elements," Analytical Chemistry 1995, 67:2142-2144.

Mei, H. et al., "Rapid In Vivo Oral Screening in Rats: Reliability, Acceptance Criteria, and Filtering Efficiency," The AAPS Journal 2006, 8(3) Article 58:E493-E500.

Quin, J. E. et al., "Targeting the nucleolus for cancer intervention," Biochimica et Biophysica Acta, vol. 1842, pp. 802-816 (2014).

Shea, K.J., "Molecular Imprinting of synthetic Network Polymers: The De Novo Synthesis of Macromolecular Binding and Catalytic Sites," Trends in Polymer Sci 1994, 2(5):166-173.

Vaickus, L. et al., "Immune markers in hematologic malignancies," Crit Rev in Oncol/Hematol 1991, 11:267-297.

Vlatakis, G. et al., "Drug assay using antibody mimics made by molecular imprinting," Nature 1993, 361:645-647.

Braga et al., "Crystal Polymorphism and Multiple Crystal Forms", Struct. Bond (2009) 132:25-50.

Caira, M. R. "Crystalline Polymorphism of Organic Compounds, In: Weber E. et al. (eds) Design of Organic Solids. Topics in Current Chemistry", vol. 198. 1998; Springer, Berlin, Heidelberg. Epub Feb. 26, 1999.

Extended European Search Report for EP. Application No. 16866873.9, dated May 21, 2019, 9 pages.

Li, L. et al. "CX-5461 induces autophagy and inhibits tumor growth via mammalian target of rapamycin-related signaling pathways in osteosarcoma", Onco Targets Ther. 2016 [Retrieved from the Internet May 7, 2019]. 9: 5985-5997. Published online Sep. 29, 2016.

Morissette, S. L., et al. "High-throughput crystallization: polymorphs, salts, co-crystals and solvates of pharmaceutical solids", Adv Drug Deliv Rev. Feb. 23, 2004. 56(3): 275-300.

Sandeep, S. N. et al. "rRNA synthesis inhibitor, CX-5461, activates ATM/ATR pathway in acute lymphoblastic leukemia, arrests cells in G2 phase and induces apoptosis", Oncotarget. Jul. 20, 2015; 6(20): 18094-18104. Published online Jun. 5, 2015.

Sandeep, S. N. et al. "Transient rRNA synthesis inhibition with CX-5461 is sufficient to elicit growth arrest and cell death in acute lymphoblastic leukemia cells", Oncotarget. Oct. 27, 2015; 6(33): 34846-34858. Published online Oct. 12, 2015.

Rodriguez-Spong, B. et al. "General principles of pharmaceutical solid polymorphism: a supramolecular perspective", Adv Drug Deliv Rev. Feb. 23, 2004; 56(3):241-74.

International Search Report and Written Opinion for International Application No. PCT/US2019/018225, dated Aug. 19, 2019, 13 pages.

National Center for Biotechnology Information. "PubChem Database. CID=68237161"; [retrieved on Aug. 30, 2019]. Retrieved from the Internet. <https://pubchem.ncbi.nlm.nih.gov/compound/68237161>, 5 pages.

Abdelwahed W., et al. "Freeze-drying of nanoparticles: formulation, process and storage considerations", Adv Drug Deliv Rev.;58(15):1688-713. (Dec. 30, 2006). Epub Oct. 6, 2006.

Haddach, M. et al. "Discovery of CX-5461, the First Direct and Selective Inhibitor of RNA Polymerase I, for Cancer Therapeutics", ACS Med Chem Lett.; 3(7): 602-606. (Jul. 12, 2012).

Schwaebe, M. K. et al. "Facile and efficient generation of quinolone amides from esters using aluminum chloride", Tetrahedron Letters; 52(1):1096-1100. (Mar. 9, 2011).

Yang, D. L. "Polymorphic Drugs", People's Health Publishing House: 6, 24-25 and 138 (2009).

Search Report dated Jun. 24, 2020 for Chinese Application No. 201580085777.5, 6 pages.

Devlin, J. R., et al. "Combination Therapy Targeting Ribosome Biogenesis and mRNA Translation Synergistically Extends Survival in MYC-Driven Lymphoma", Cancer Discov.; 6(1):59-70. (Jan. 2016). Epub Oct. 21, 2015.

\* cited by examiner

Compound A (μM)

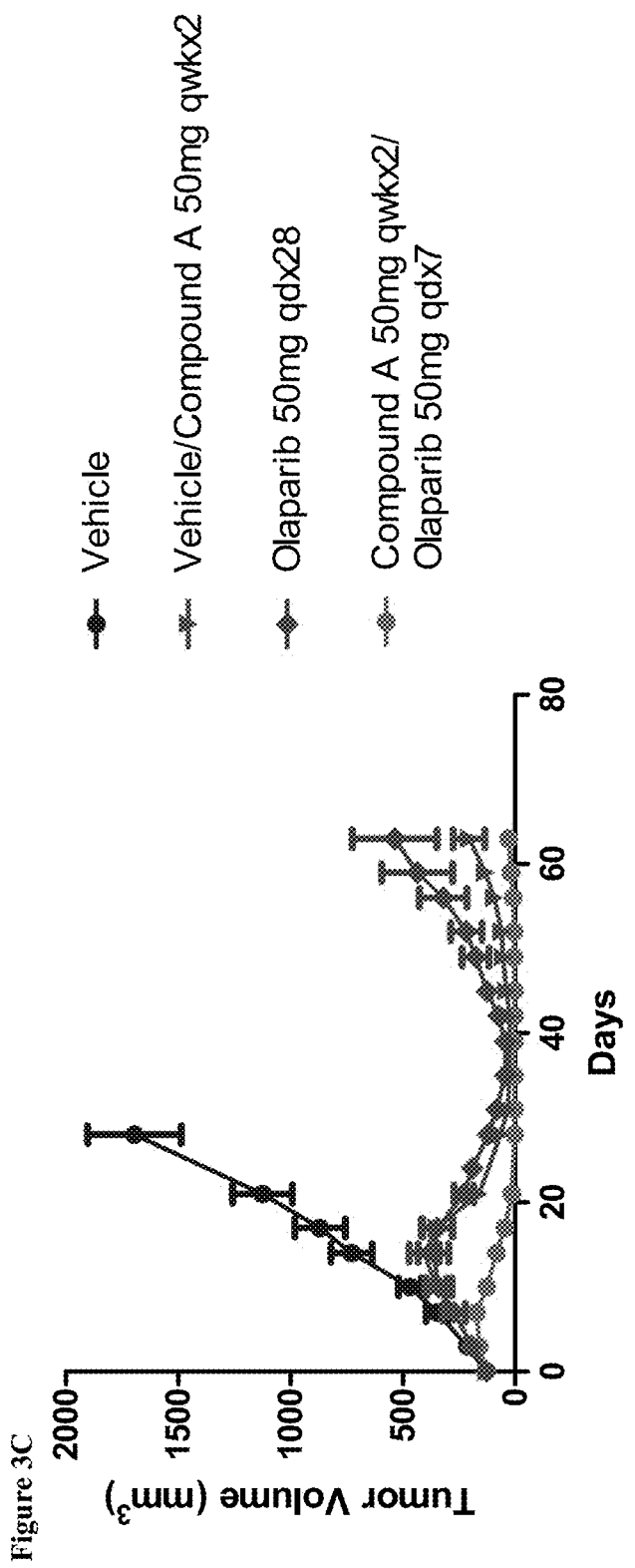

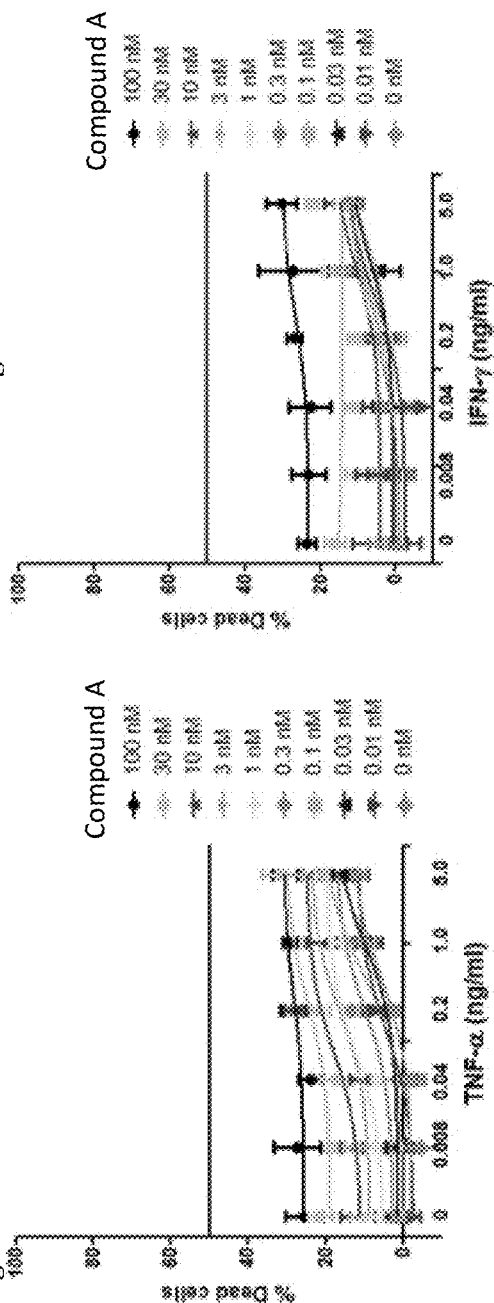

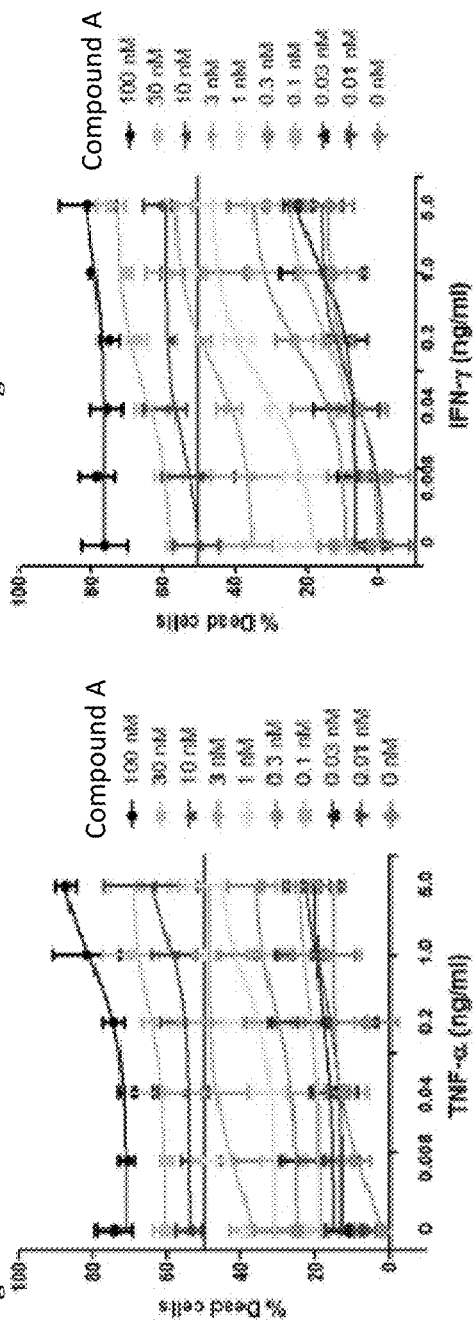

COMBINATION THERAPY OF TETRACYCLIC QUINOLONE ANALOGS FOR TREATING CANCER

CROSS-REFERENCE TO RELATED PATENT APPLICATIONS

The present application claims priority to, and the benefit of U.S. Provisional Patent Application Ser. No. 62/258,211, filed Nov. 20, 2015, which is hereby incorporated by reference in its entirety for all purposes.

FIELD OF THE DISCLOSURE

The present invention generally relates to a combination therapy for treating cancer and tumors.

BACKGROUND OF THE DISCLOSURE

A variety of tetracyclic quinolone compounds have been suggested to function by interacting with quadruplex-forming regions of nucleic acids and modulating ribosomal RNA transcription. See, for example, U.S. Pat. Nos. 7,928,100 and 8,853,234. Specifically, the tetracyclic quinolone compounds can stabilize the DNA G-quadruplexes (G4s) in cancer cells and thereby induce synthetic lethality in cancer cells. Since treatment of cells with G4-stabilizing agents can lead to the formation of DNA double strand breaks (DSBs), DSB formation induced by G4-stabilizing ligand/agent (such as the tetracyclic quinolones) treatment would be more pronounced in cells genetically deficient in, or chemically inhibited in, repair pathways including both non-homologous end joining (NHEJ), homologous recombination repair (HRR). Furthermore, the tetracyclic quinolone compounds selectively inhibit rRNA synthesis by Pol I in the nucleolus, but do not inhibit mRNA synthesis by RNA Polymerase II (Pol II) and do not inhibit DNA replication or protein synthesis. For example, it is suggested that targeting RNA polymerase I (Pol I) to activate p53 through the nucleolar stress pathway may results in selective activation of p53 in tumor cells. The p53 protein normally functions as a tumor suppressor by causing cancer cells to self-destruct. Activating p53 to kill cancer cells is a well validated anticancer strategy and many approaches are being employed to exploit this pathway. Selective activation of p53 in tumor cells would be an attractive method of treating, controlling, ameliorating tumor cells while not affecting normal healthy cells. The aforementioned tetracyclic quinolones are disclosed in U.S. Pat. Nos. 7,928,100 and 8,853,234, and the contents of this publication are herein incorporated by reference in their entirety for all intended purposes.

Despite the recent development of anti-cancer agents, there is still a strong need for developing effective novel cancer therapy.

SUMMARY OF THE DISCLOSURE

In one embodiment, the present invention provides a pharmaceutical combination comprising a tetracyclic quinolone compound having the structure of formula (I);

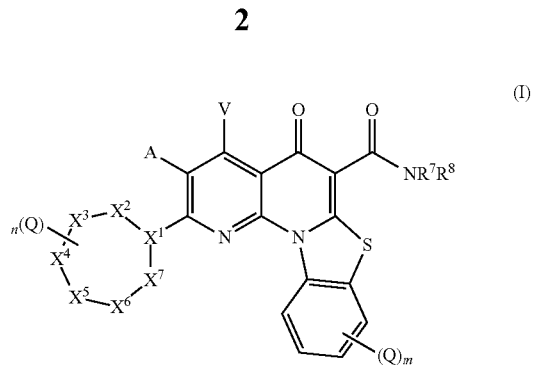

or a pharmaceutically acceptable salt, ester, solvate and/or prodrug thereof;

wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that zero, one or two of $X^2$, $X^3$, $X^4$, $X^5$, $X^6$ and $X^7$ are $NR^4$;

A and V independently are H, halo, azido, —CN, —$CF_3$, —$CONR^1R^2$, —$NR^1R^2$, —$SR^2$, —$OR^2$, or —$R^3$;

each Q is independently halo, azido, —CN, —$CF_3$, —$CONR^1R^2$, —$NR^1R^2$, —$SR^2$, —$OR^2$, or —$R^3$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4; and n is 0, 1, 2, 3, 4, or 5;

and at least one additional therapeutically active agent selected from the group consisting of immunotherapeutic agents, anticancer agents, and angiogenic agents.

In another embodiment, a pharmaceutical combination is provided comprising a therapeutically effective amount of a compound of formula (II);

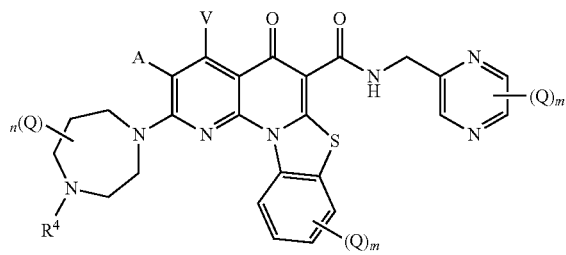

(II)

or a pharmaceutically acceptable salt, ester, solvate and/or prodrug thereof;
wherein:
A and V independently are H, halo, azido, —CN, —CF$_3$, —CONR$^1$R$^2$, —NR$^1$R$^2$, —SR$^2$, —OR$^2$, or —R$^3$;
each Q is independently halo, azido, —CN, —CF$_3$, —CONR$^1$R$^2$, —NR$^1$R$^2$, —SR$^2$, —OR$^2$, or —R$^3$;
in each —NR$^1$R$^2$, R$^1$ and R$^2$ together with N may form an optionally substituted azacyclic ring, optionally containing an additional heteroatom selected from N, O and S as a ring member;
R$^1$ is H or C1-C6 alkyl, optionally substituted with one or more halogens, or =O;
R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;
R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;
each R$^4$ is independently H, or C1-C6 alkyl;
m is 0, 1, 2, 3 or 4;
n is 0, 1, 2, 3, 4 or 5; and
p is 0, 1, 2 or 3;
and at least one additional therapeutically active agent selected from the group consisting of immunotherapeutic agents, anticancer agents, and angiogenic agents.

In one embodiment, a pharmaceutical combination is provided comprising a therapeutically effective amount of a compound of formula (III);

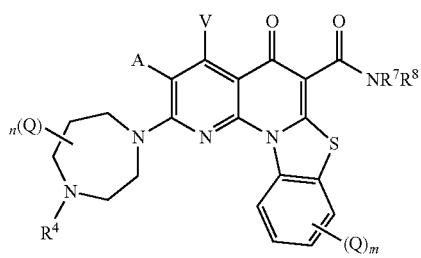

(III)

or a pharmaceutically acceptable salt, ester, solvate and/or prodrug thereof;
wherein:
A and V independently are H, halo, azido, —CN, —CF$_3$, —CONR$^1$R$^2$, —NR$^1$R$^2$, —SR$^2$, —OR$^2$, or —R$^3$;
each Q is independently halo, azido, —CN, —CF$_3$, —CONR$^1$R$^2$, —NR$^1$R$^2$, —SR$^2$, —OR$^2$, or —R$^3$;

in each —NR$^1$R$^2$, R$^1$ and R$^2$ together with N may form an optionally substituted azacyclic ring, optionally containing an additional heteroatom selected from N, O and S as a ring member;
R$^1$ is H or C1-C6 alkyl, optionally substituted with one or more halogens, or =O;
R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;
R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;
each R$^4$ is independently H, or C1-C6 alkyl;
R$^7$ is H and R$^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;
m is 0, 1, 2, 3 or 4; and
n is 0, 1, 2, 3, 4 or 5;
and at least one additional therapeutically active agent selected from the group consisting of immunotherapeutic agents, anticancer agents, and angiogenic agents.

In one embodiment, a pharmaceutical combination is provided comprising Compound A and at least one additional therapeutically active agent.

Compound A

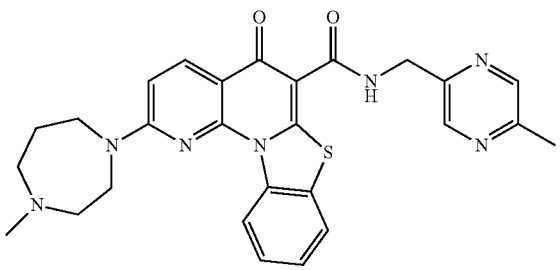

In one embodiment, a pharmaceutical combination is provided comprising a compound of formula (I) and at least one additional therapeutically active agent in a single dosage form or in separate dosage forms. In another embodiment, the pharmaceutical combination where the compound of formula (I) and at least one additional therapeutically active agent are in separate dosage forms are administered by the same mode of administration or a different mode of administration. In one embodiment, the separate dosage forms of a pharmaceutical combination provided herein, are co-administered by simultaneous administration, sequential administration, overlapping administration, interval administration, continuous administration, or a combination thereof.

In one embodiment of the present invention, a pharmaceutical combination is provided comprising a compound of formula (I), (IA), (IB), (II), (IIA), (III), (IIIA), and/or their subgenera, or Compound A, or salts, solvates, esters and/or prodrugs thereof and at least one additional therapeutically active agent. In some embodiments, the additional therapeutically active agent is an immunotherapeutic agent, an anticancer agent, and/or an anti-angiogenic agent.

In one embodiment, the at least one additional therapeutically active agent is an immunotherapeutic agent. In some embodiments, an immunotherapeutic agent is selected from the group consisting of: monoclonal antibody, an immune effector cell, adoptive cell transfer, an immunotoxin, a vaccine, or a cytokine.

In other embodiments, an immunotherapeutic agent is an agent that can modulate the physiological levels of one or more cytokines in the tumor microenvironment of cancers. In some embodiments, the immunotherapeutic agent induces local production of at least one endogenous cytokine that has cytotoxic effect on tumor cells, such as TNF-α or IFN-γ. In some embodiments, the immunotherapeutic agent inhibits the production of an endogenous cytokine that interferes with T-cell recognition and destruction of cancer cells, such as IL-10, TGFβ, or VEGF.

In other embodiments, an immunotherapeutic agent is an agent that can induce tumor cell production of one or more chemokines that attract immune cells such as dendritic cells, effector T-cell (e.g., CD8+ lymphocytes), and natural killer (NK) cells to tumor cells. In some embodiments, the chemokines include, but are not limited to, CCL19, CCL20, CCL21, CX3CL1, CXCL9, and CXCL10.

In other embodiments, an immunotherapeutic agent is an agent that induces immune checkpoint blockade, such as PD-1 blockade and CTLA-4 blockade.

In some embodiments, the immunotherapeutic agent is an antibody or an antigen-binding portion thereof that disrupts the interaction between Programmed Death-1 (PD-1) and Programmed Death Ligand-1 (PD-L1). In one embodiment, an immunotherapeutic agent is selected from the group consisting of: an anti-PD-1 antibody, a PD-1 antagonist, an anti-PD-L1 antibody, a siRNA targeting expression of PD-1, a siRNA targeting the expression of PD-L1, and a peptide, fragment, dominant negative form, or soluble form of PD-1 or PD-L1.

In one embodiment, an immunotherapeutic agent is a monoclonal antibody. In one embodiment, the monoclonal antibody is selected from the group consisting of anti-PD-1 antibody, nivolumab, pembrolizumab alemtuzumab, bevacizumab, brentuxima b vedotin, cetuximab, gemtuzumab ozogamicin, ibritumomab tiuxetan, ipilimumab, ofatumumab, panitumumab, rituximab, tositumomab, trastuzumab, anti-B7-H4, anti-B7-H1, anti-LAG3, BTLA, anti-Tim3, anti-B7-DC, anti-CD160, MR antagonist antibodies, anti-4-1BB, anti-OX40, anti-CD27, and/or CD40 agonist antibodies. In some embodiments, an immunotherapeutic agent is an anti-PD-1 antibody. In other embodiments, an anti-PD-1 antibody is a humanized antibody. In one embodiment, the monoclonal antibody is selected from the group consisting of nivolumab and pembrolizumab. In a specific embodiment, the monoclonal antibody is nivolumab.

In one embodiment, an immunotherapeutic agent is selected from the group consisting of a CTLA-4 antagonist, an anti-CTLA-4 antibody, a siRNA targeting the expression of CTLA-4, and/or a peptide, fragment, dominant negative or soluble form of CTLA-4. In one embodiment, the anti-CTLA-4 antibody is ipilimumab.

In some embodiments, the pharmaceutical combination is provided comprising a compound of formula (I), (IA), (IB), (II), (IIA), (III), (IIIA), and/or their subgenera, or Compound A, or salts, solvates, esters and/or prodrugs thereof and at least one anticancer agent. In one embodiment, said anticancer agent is selected from the group consisting of an alkylating agent, an anti-metabolite, a vinca alkaloid, a taxane, a topoisomerase inhibitor, an anti-tumor antibiotic, a tyrosine kinase inhibitor, an immunosuppressive macrolide, an Akt inhibitor, an HDAC inhibitor an Hsp90 inhibitor, an mTOR inhibitor, a PI3K/mTOR inhibitor, a PI3K inhibitor, a CDK (cyclin-dependent kinase) inhibitor, CHK (checkpoint kinase) inhibitor, PARP (poly (DP-ribose)polymerase) inhibitors, and combinations thereof.

In one embodiment, at least one anticancer agent is a PI3K inhibitor. In another embodiment, the PI3K inhibitor is Idelalisib.

In one embodiment, at least one anticancer agent is a PARP inhibitor. In another embodiment, the PARP inhibitor is Olaparib.

In other embodiments, the pharmaceutical combination is provided comprising a compound of formula (I), (IA), (IB), (II), (IIA), (III), (IIIA), and/or their subgenera, or Compound A, or salts, solvates, esters and/or prodrugs thereof and at least one anti-angiogenic agent. In one embodiment, said antiangiogenic agent is selected from the group consisting of 2-methoxyestradiol, AG3340, prinomastat, batimastat, BAY 12-9566, carboxyamidotriazole, CC-1088, dextromethorphan acetic acid, dimethylxanthenone acetic acid, EMD 121974, endostatin, IM-862, marimastat, matrix metalloproteinase, penicillamine, PTK787/ZK 222584, RPI.4610, squalamine, squalamine lactate, 3-[2,4-dimethylpyrrol-5-yl-methyl-idenyl]-2-indolinone (SU5416), (±)-thalidomide, S-thalidomide, R-thalidomide, O-(chloroacetylcarbamoyl) fumagillol (TNP-470), combretastatin, paclitaxel, tamoxifen, COL-3, neovastat, BMS-275291, SU6668, 2-ME, interferon-alpha, anti-VEGF antibody, Medi-522 (Vitaxin II), CAI (inhibitor of calcium influx), celecoxib, Interleukin-12, IM862, amilloride, Angiostatin® protein, angiostatin K1-3, angiostatin K1-5, captopril, DL-alpha-difluoromethylornithine, DL-alpha-difluoromethylornithine HCl, His-Tag® Endostatin™ Protein, fumagillin, herbimycin A, 4-hydroxyphenylretinamide, gamma-interferon, juglone, laminin, laminin hexapeptide, laminin pentapeptide, lavendustin A, medroxyprogesterone, medroxyprogesterone acetate, minocycline, minocycline HCl, placental ribonuclease inhibitor, suramin, sodium salt Suramin, human platelet thrombospondin, tissue inhibitor of metalloproteinase 1,neutrophil granulocyte tissue inhibitor of metalloproteinase 1, rheumatoid synovial fibroblast tissue inhibitor of metalloproteinase 2, and combinations thereof.

In some embodiments, a pharmaceutical combination is provided comprising a compound of formula (I), (IA), (IB), (II), (IIA), (III), (IIIA), and/or their subgenera, or Compound A, or salts, solvates, esters and/or prodrugs thereof, at least one additional therapeutically active agent, and a pharmaceutically acceptable excipient or a pharmaceutically acceptable carrier.

In one embodiment, a pharmaceutical combination is provided comprising a compound of formula (I), (IA), (IB), (II), (IIA), (III), (IIIA), and/or their subgenera, or Compound A, or salts, solvates, esters and/or prodrugs thereof, which is present in an amount from about 1 mg to about 500 mg.

In another embodiment, the pharmaceutical combination is provided wherein the compound is compound A and wherein the at least one additional therapeutically active agent is selected from one or more of the group consisting of a PARP inhibitor and an anti-PD-1 antibody. In a specific embodiment the PARP inhibitor is Olaparib. In another specific embodiment, the anti-PD-1 antibody is nivolumab.

In one embodiment, a method for stabilizing G-quadruplexes (G4s) in a subject is provided where the method comprises administering to the subject a therapeutically effective amount of a pharmaceutical combination comprising a compound of formula (I), (IA), (IB), (II), (IIA), (III), (IIIA), and/or their subgenera, or Compound A, or salts, solvates, esters and/or prodrugs thereof and at least one additional therapeutically active agent, as described herein. In some embodiments, a method for stabilizing G-quadruplexes (G4s) in a subject is provided where the method comprises administering to the subject a therapeutically effective amount of a pharmaceutical combination comprising a compound of formula (I), (IA), (IB), (II), (IIA), (III), (IIIA), and/or their subgenera, or Compound A, or salts, solvates, esters and/or prodrugs thereof and administering radiotherapy or at least one additional therapeutically active agent before, during, or after the subject has been administered the aforementioned compound.

In one embodiment, a method for modulating p53 activity in a subject is provided where the method comprises administering to the subject a therapeutically effective amount of a pharmaceutical combination comprising a compound of formula (I), (IA), (IB), (II), (IIA), (III), (IIIA), and/or their subgenera, or Compound A, or salts, solvates, esters and/or prodrugs thereof and at least one additional therapeutically active agent, as described herein. In some embodiments, a method for modulating p53 activity in a subject is provided where the method comprises administering to the subject a therapeutically effective amount of a pharmaceutical combination comprising a compound of formula (I), (IA), (IB), (II), (IIA), (III), (IIIA), and/or their subgenera, or Compound A, or salts, solvates, esters and/or prodrugs thereof and administering radiotherapy or at least one additional therapeutically active agent before, during, or after the subject has been administered the aforementioned compound.

In one embodiment, a method for treating or ameliorating cell proliferation disorder in a subject is provided where said method comprises administering to a subject in need thereof a therapeutically effective amount of a pharmaceutical combination comprising a compound of formula (I), (IA), (IB), (II), (IIA), (III), (IIIA), and/or their subgenera, or Compound A, or salts, solvates, esters and/or prodrugs thereof and at least one additional therapeutically active agent, as described herein. In some embodiments, a method for treating or ameliorating cell proliferation disorder in a subject is provided where said method comprises administering to a subject in need thereof a therapeutically effective amount of a compound of formula (I), (IA), (IB), (II), (IIA), (III), (IIIA), and/or their subgenera, or Compound A, or salts, solvates, esters and/or prodrugs thereof and administering radiotherapy or at least one additional therapeutically active agent before, during, or after the subject has been administered the aforementioned compound.

In one embodiment, the methods described herein provides administering a therapeutically effective amount of a pharmaceutical combination comprising a compound of formula (I), (IA), (IB), (II), (IIA), (III), (IIIA), and/or their subgenera, or Compound A, or salts, solvates, esters and/or prodrugs thereof and at least one additional therapeutically active agent, where said at least one additional therapeutically active agent is selected from the group consisting of immunotherapeutic agents, anticancer agents, and angiogenic agents.

In one embodiment, the methods described herein are useful for the treatment of cancer. In one embodiment, said cancer is selected from the group consisting of: heme cancer, colorectum cancer, ovarian cancer, breast cancer, cervical cancer, lung cancer, liver cancer, pancreatic cancer, cancer of the lymph nodes, colon cancer, prostate cancer, brain cancer, cancer of the head and neck, bone cancer, Ewing's sarcoma, skin cancer, kidney cancer, and cancer of the heart. In another embodiment, said cancer is selected from the group consisting of wherein the cancer is selected from the group consisting of breast cancer, ovarian cancer, pancreatic cancer, prostate cancer, lung cancer, Ewing's sarcoma, head and neck cancer, and cervical cancer.

In one embodiment, the methods described herein are useful for treatment of heme cancer. In some embodiments, said heme cancer is selected from the group consisting of: leukemia, lymphoma, myeloma, and multiple myeloma.

In some embodiments, the methods described herein are useful for treatment of cancer which is homologous recombination dependent double strand break repair deficient cancer. In another embodiment, the methods described herein are useful for treatment of cancer cells harboring defects in breast cancer 1 (BRCA1), breast cancer 2 (BRCA2), and/or other members of the homologous recombination pathway. In one embodiment, the cancer cells have phenotype selected from the group consisting of: an ataxia telangiectasia mutated (ATM) deficient phenotype, an ataxia telangiectasia and Rad3 related (ATR) deficient phenotype, an CHK1 checkpoint homolog (S. pombe) (CHK1) deficient phenotype, an CHK2 checkpoint homolog (S. pombe) (CHK2) deficient phenotype, an RAD51 homoiog (RecA homolog, E. coli) (S. cerevisiae) (Rad51) deficient phenotype, an replication protein A (RPA) deficient phenotype and an X-ray repair complementing defective repair in Chinese hamster cells 3 (XRCC3) deficient phenotype. In one embodiment, the cancer cells are deficient in a gene selected from the group consisting of: ATM, ATR, CHK1, CHK2, Rad51, RPA and XRCC3. In another embodiment, the cancer cells are deficient in a gene selected from the group consisting of: Fanconi anemia, complementation group A (FANCA), Fanconi anemia, complementation group (FANCC), Fanconi anemia, complementation group D2 (FANCD2), Fanconi anemia, complementation group F (FANCF), Fanconi anemia, complementation group G (FANCG) and Fanconi anemia, complementation group M (FANCM). In another embodiment, the cancer cells are homozygous for a mutation in a gene selected from the group consisting of: FANCA, FANCC, FANCD2, FANCF, FANCG and FANCM. In some embodiments, said cancer cells are deficient in BRCA1 and/or BRCA2. In one embodiment, the cancer cells are homozygous for a mutation in BRCA1 and/or BRCA2. In another embodiment, the cancer cells are heterozygous for a mutation in BRCA1 and/or BRCA2.

In one embodiment, the methods described herein are useful for treating a human subject.

In another embodiment, the methods described herein, further comprises administering one or more additional therapeutic agents. In one embodiment, said one or more additional therapeutic agent is an anticancer agent.

In one embodiment, a method is provided for reducing or inhibiting cell proliferation where said method comprises contacting cells with a therapeutically effective amount of a pharmaceutical combination comprising a compound of formula (I), (IA), (IB), (II), (IIA), (III), (IIIA), and/or their subgenera, or Compound A, or salts, solvates, esters and/or prodrugs thereof and at least one additional therapeutically active agent, as described herein. In some embodiments, a method is provided for reducing or inhibiting cell proliferation where said method comprises contacting cells with a compound of formula (I), (IA), (IB), (II), (IIA), (III), (IIIA), and/or their subgenera, or Compound A, or salts, solvates, esters and/or prodrugs thereof and administering radiotherapy before, during, or after the cell has been contacted with a compound of formula (I), (IA), (IB), (II), (IIA), (III), (IIIA), and/or their subgenera, or Compound A.

In one embodiment, the method for reducing or inhibiting cell proliferation as described herein are in a cancer cell line or in a tumor in a subject. In one embodiment, said cancer cell line is a cancer cell line selected from the group consisting of: heme cancer, colorectum cancer, ovarian cancer, breast cancer, cervical cancer, lung cancer, liver cancer, pancreatic cancer, cancer of the lymph nodes, colon cancer, prostate cancer, brain cancer, cancer of the head and neck, bone cancer, Ewing's sarcoma, skin cancer, kidney cancer, and cancer of the heart. In another embodiment, a cancer cell line selected from the group consisting of wherein the cancer is selected from the group consisting of breast cancer, ovarian cancer, pancreatic cancer, prostate cancer, lung cancer, Ewing's sarcoma, head and neck cancer, and cervical cancer.

In one embodiment, the method for reducing or inhibiting cell proliferation as described herein are in a cancer cell line or in a tumor in a subject is a heme cancer cell line is selected from the group consisting of: leukemia, lymphoma, myeloma, and multiple myeloma.

In one embodiment, the method for reducing or inhibiting cell proliferation as described herein are in cancer cells harboring a defect in breast cancer 1 (BRCA1), breast cancer 2 (BRCA2), and/or other members of the homologous recombination pathway. In one embodiment, the cancer cells have phenotype selected from the group consisting of: an ataxia telangiectasia mutated (ATM) deficient phenotype, an ataxia telangiectasia and Rad3 related (ATR) deficient phenotype, an CHK1 checkpoint homolog (S. pombe) (CHK1) deficient phenotype, an CHK2 checkpoint homolog (S. pombe) (CHK2) deficient phenotype, an RAD51 homoiog (RecA homolog, E. coli) (S. cerevisiae) (Rad51) deficient phenotype, an replication protein A (RPA) deficient phenotype and an X-ray repair complementing defective repair in Chinese hamster cells 3 (XRCC3) deficient phenotype. In one embodiment, the cancer cells are deficient in a gene selected from the group consisting of: ATM, ATR, CHK1, CHK2, Rad51, RPA and XRCC3. In another embodiment, the cancer cells are deficient in a gene selected from the group consisting of: Fanconi anemia, complementation group A (FANCA), Fanconi anemia, complementation group (FANCC), Fanconi anemia, complementation group D2 (FANCD2), Fanconi anemia, complementation group F (FANCF), Fanconi anemia, complementation group G (FANCG) and Fanconi anemia, complementation group M (FANCM). In another embodiment, the cancer cells are homozygous for a mutation in a gene selected from the group consisting of: FANCA, FANCC, FANCD2, FANCF, FANCG and FANCM. In some embodiments, said cancer cells are deficient in BRCA1 and/or BRCA2. In one embodiment, the cancer cells are homozygous for a mutation in BRCA1 and/or BRCA2. In another embodiment, the cancer cells are heterozygous for a mutation in BRCA1 and/or BRCA2.

In one embodiment, the methods described herein is useful in administering said pharmaceutical combinations 1-4 times a day, 1-6 times a week, 1-4 times a month, once a week, once every two weeks, once every three weeks, or once a month.

BRIEF DESCRIPTIONS OF THE FIGURES

Figure 1B:
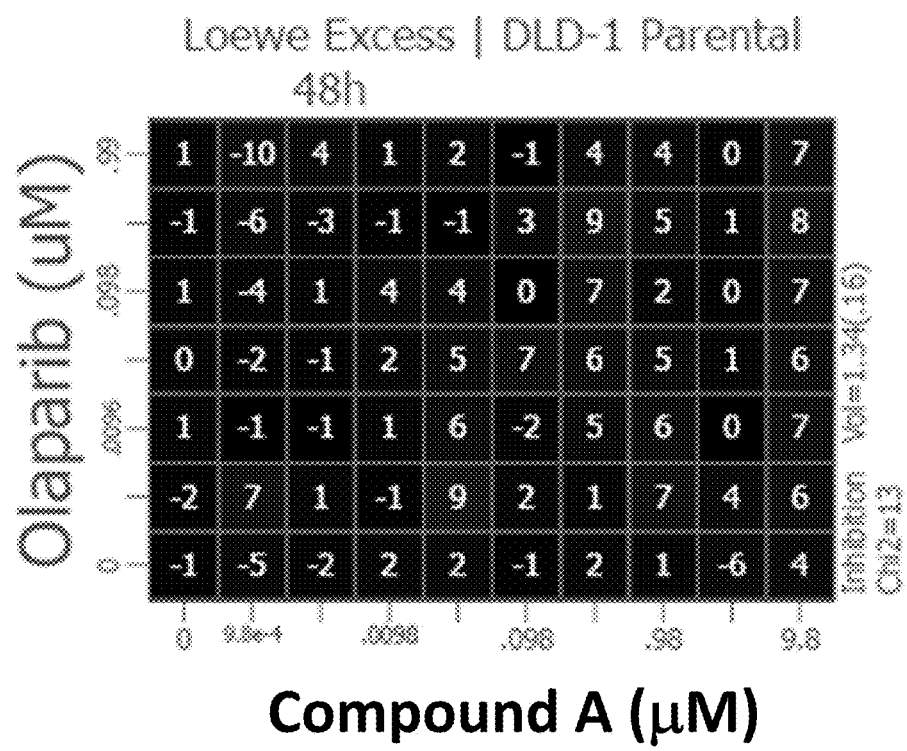
Figure 1C:
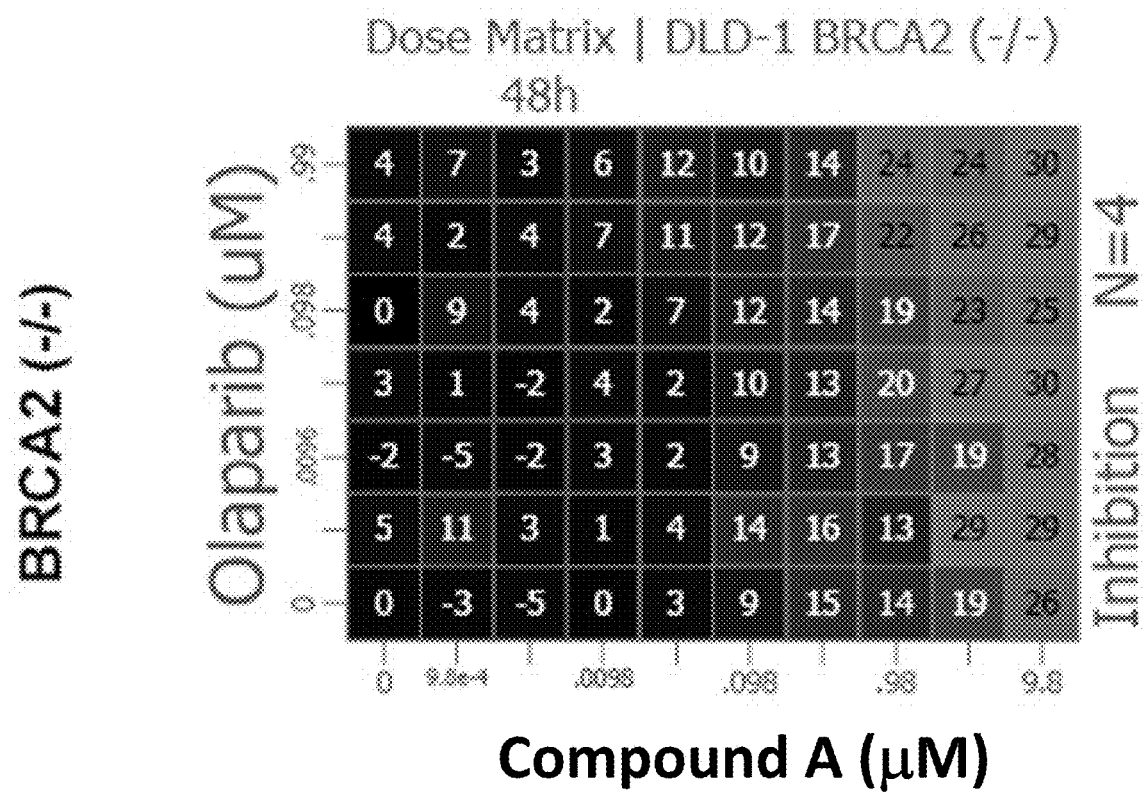
Figure 1D:
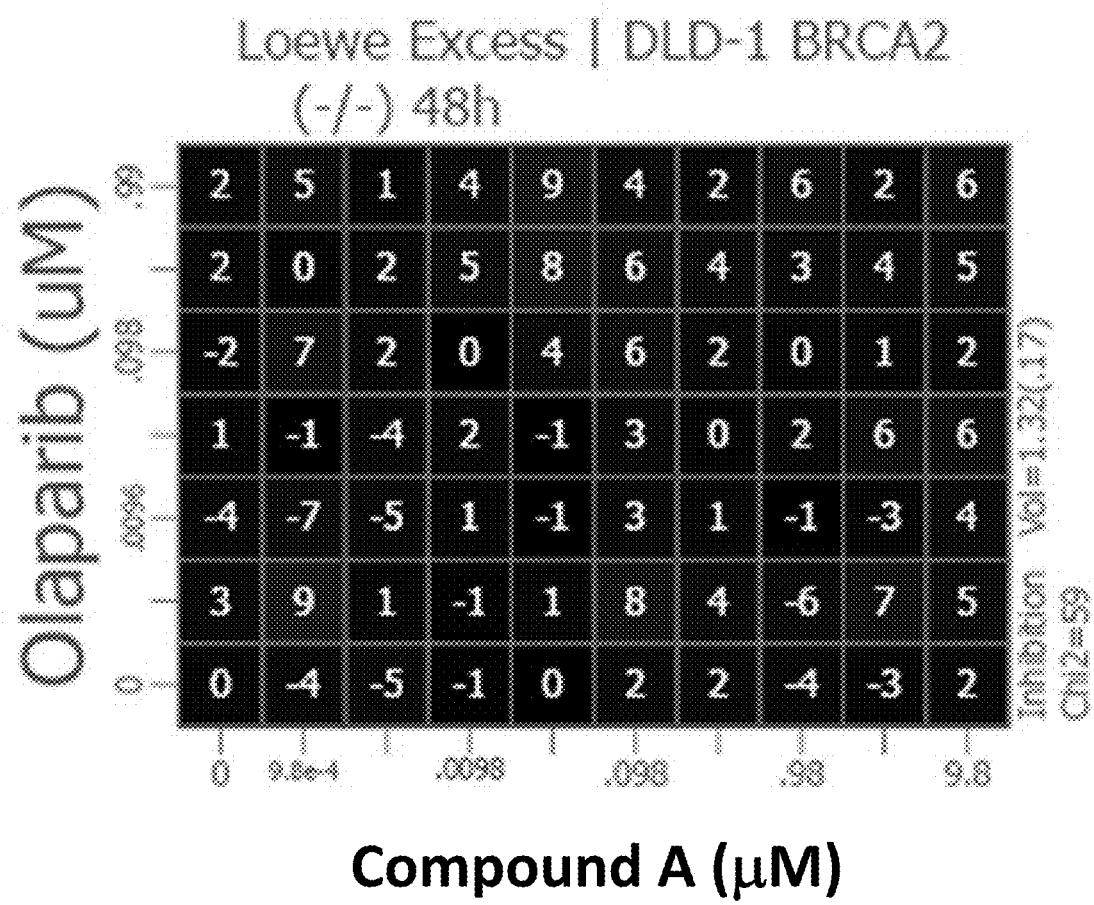

FIGS. 1A-1D show growth inhibition and Loewe Excess in Compound A and Olaparib combination for 48 hours. FIG. 1A shows a dose matrix showing inhibition (%) for the combination in DLD1 parental cell lines. FIG. 1B shows Loewe excess for the combination in FIG. 1A. FIG. 1C shows a dose matrix showing inhibition (%) for the combination in DLD1-BRCA2 (−/−) isogenic cell lines. FIG. 1D shows Loewe excess for the combination in FIG. 1C.

Figure 2A:
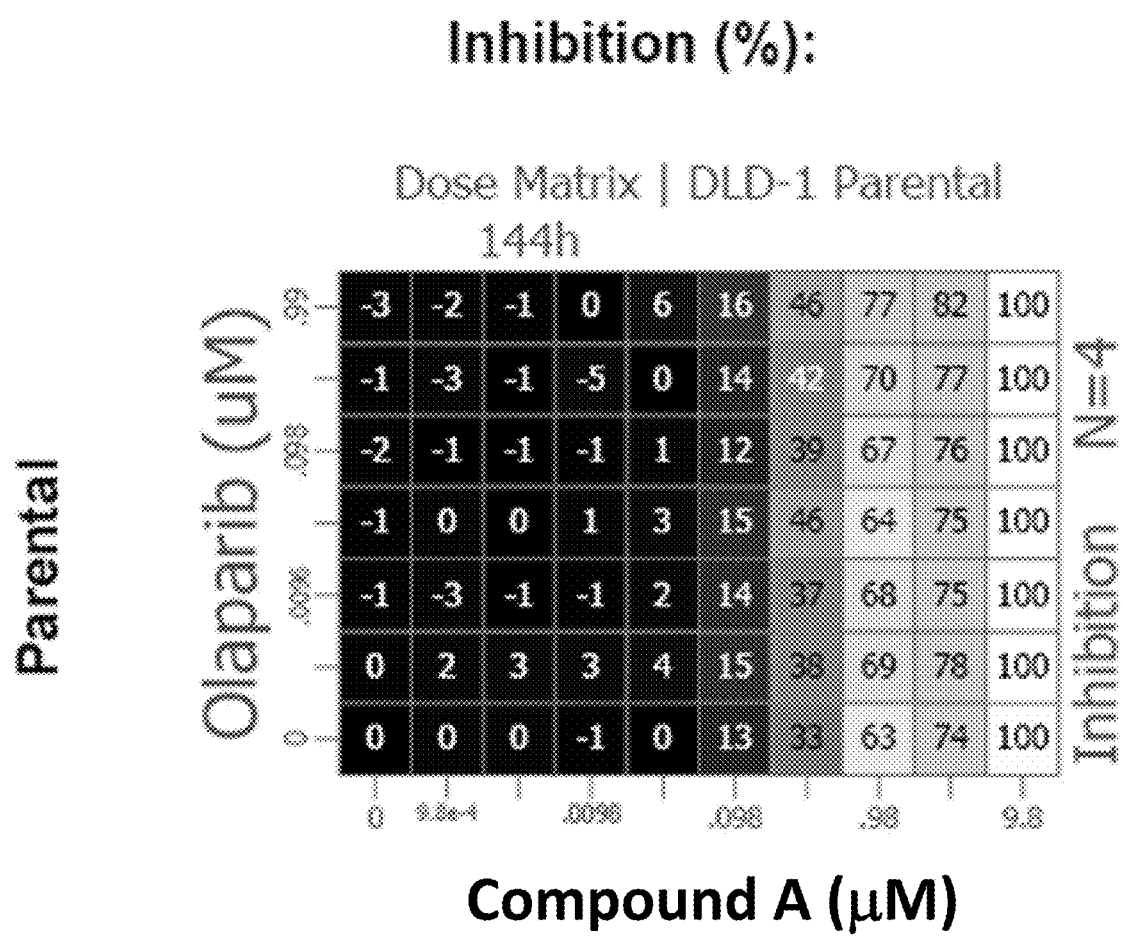
Figure 2B:
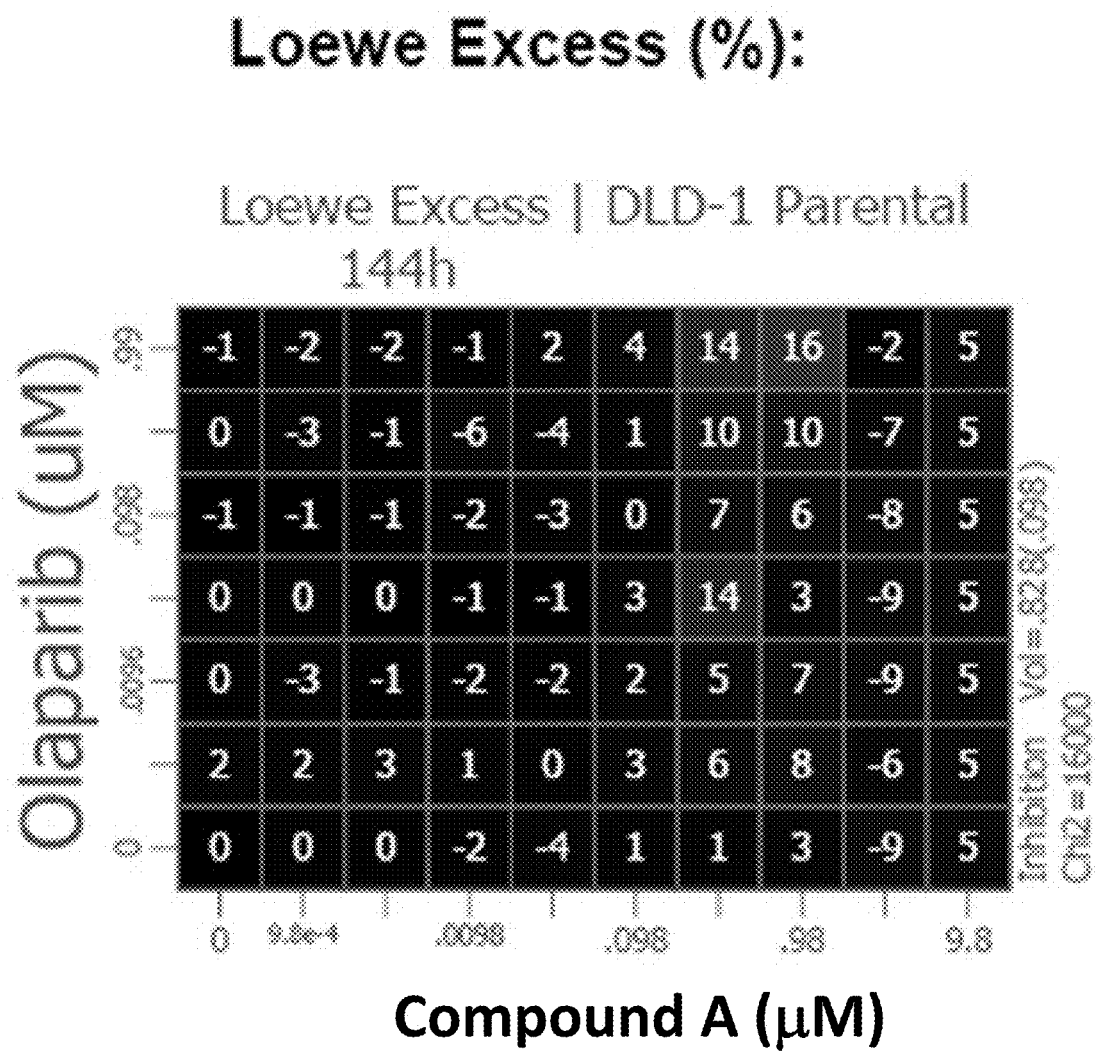
Figure 2C:
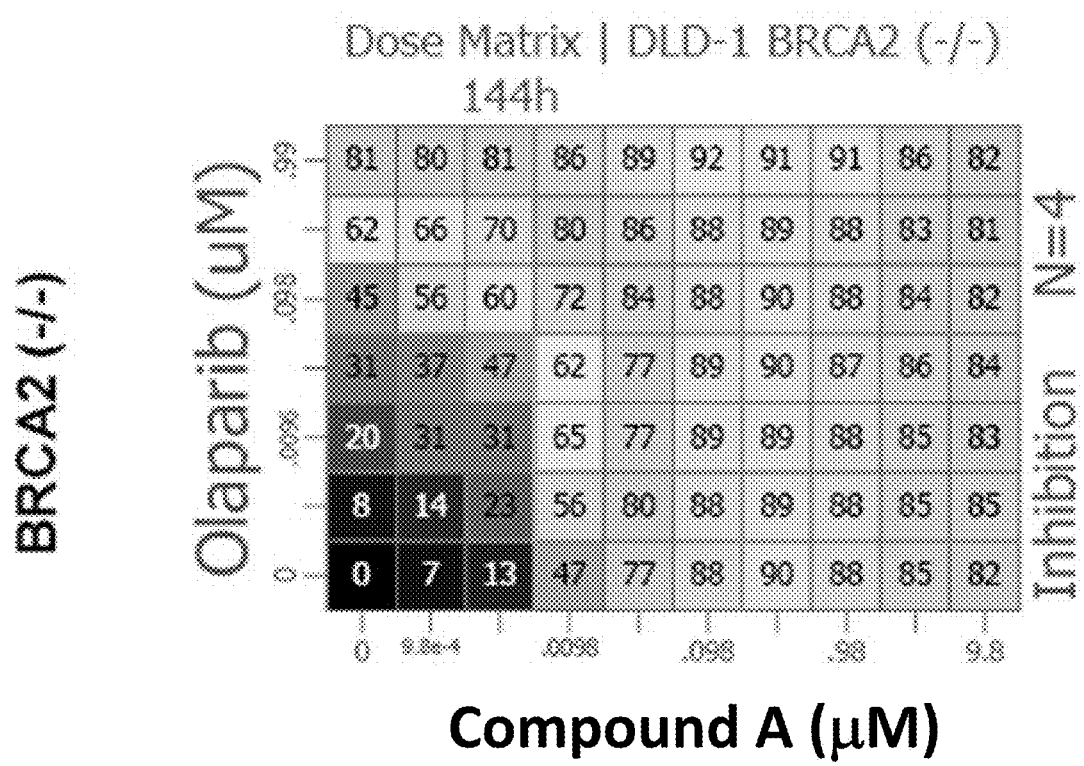
Figure 2D:
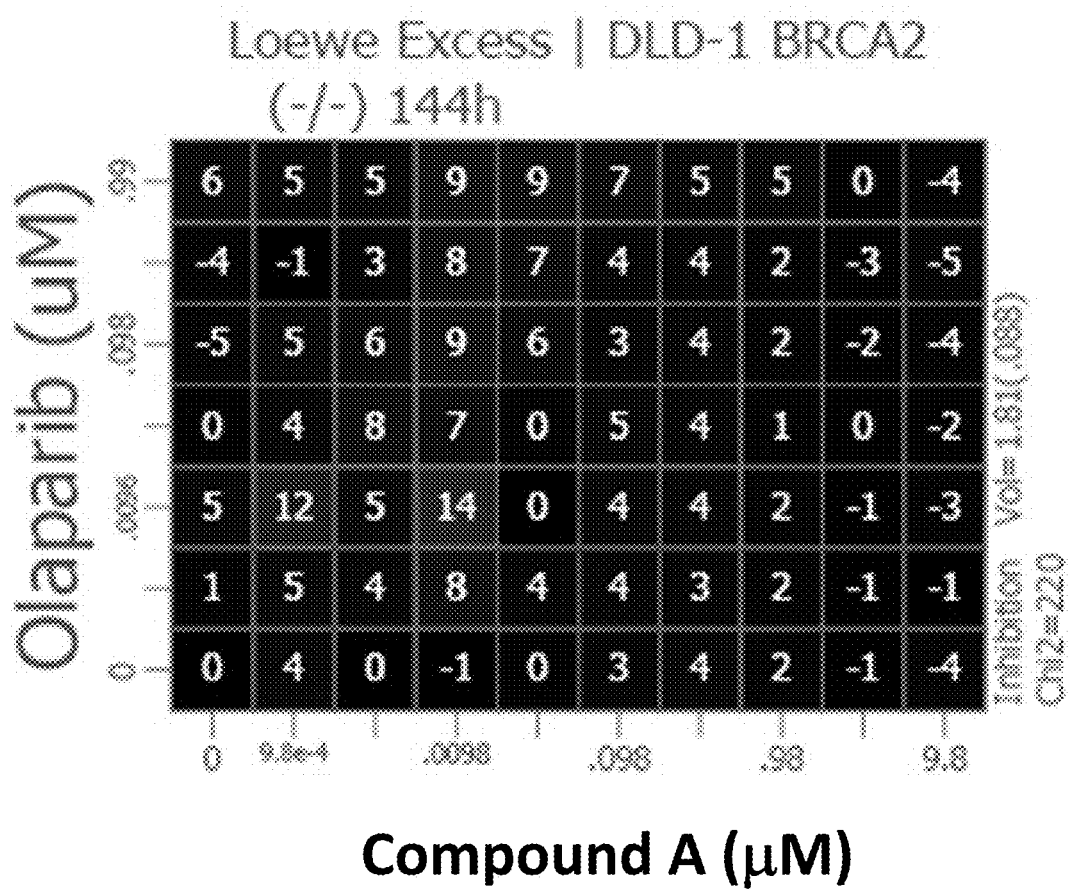

FIGS. 2A-2D show growth inhibition and Loewe Excess in Compound A and Olaparib combination for 144 hours. FIG. 2A shows a dose matrix showing inhibition (%) for the combination in DLD1 parental cell lines. FIG. 2B shows Loewe excess for the combination in FIG. 2A. FIG. 2C shows a dose matrix showing inhibition (%) for the combination in DLD1-BRCA2 (−/−) isogenic cell lines. FIG. 2D shows Loewe excess for the combination in FIG. 2C.

Figure 3A:
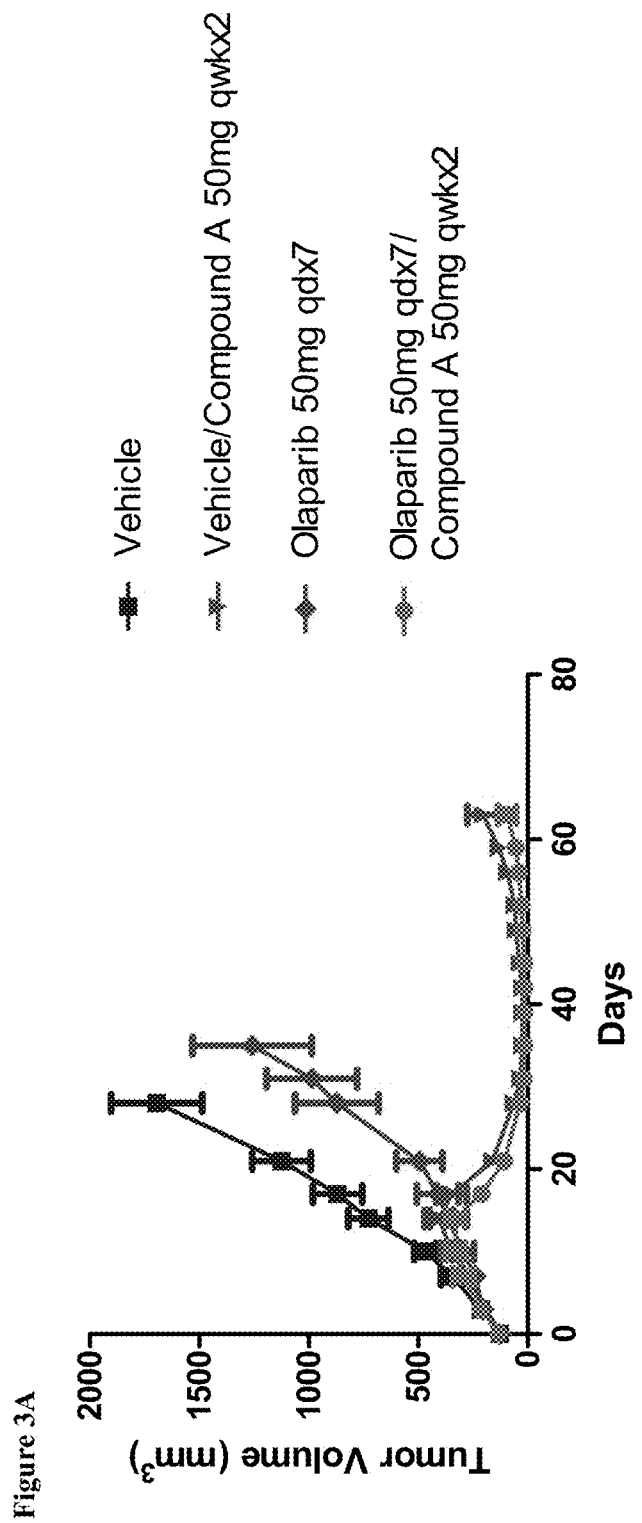
Figure 3B:
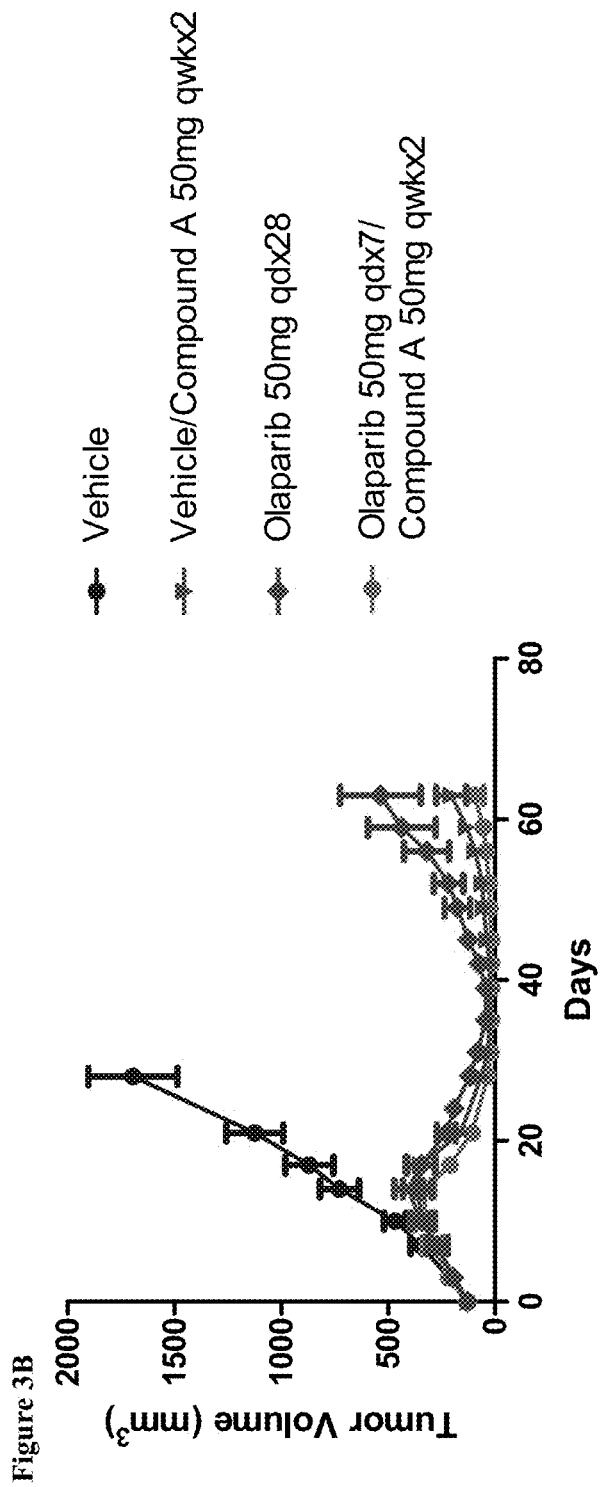

FIGS. 3A-3C show combination therapy of Compound A and the PARP inhibitor Olaparib demonstrating in vivo synergy in a PDX model of BRCA2-deficient TNBC. FIG. 3A shows treatments of Olaparib (50 mg, qd×7) and Olaparib (50 mg, qd×7) combined with Compound A (50 mg qwk×2). FIG. 3B shows treatments of Olaparib (50 mg, qd×28) and Olaparib (50 mg, qd×28) combined with Compound A (50 mg qwk×2). FIG. 3C shows treatments of Olaparib (50 mg, qd×28) and Compound A (50 mg qwk×2) combined with Olaparib (50 mg, qd×7).

FIG. 4A shows dose response curves of TNF-α on BRCA positive (UWB1.289) cell viability following treatment with various concentrations of Compound A. FIG. 4B shows dose response curves of INF-γ on BRCA positive cell viability following treatment with various concentrations of Compound A. % inhibition values of CellTiter-Glo® Luminescent cell viability assay.

FIG. 5A shows dose response curves of TNF-α on BRCA1 negative (UWB1.289-2945) cell viability following treatment with various concentrations of Compound A. FIG. 5B shows dose response curves of INF-γ on BRCA1 negative cell viability following treatment with various concentrations of Compound A. % inhibition values of CellTiter-Glo® Luminescent cell viability assay. Each data point is mean±SD from three independent determinations.

Figure 6A:
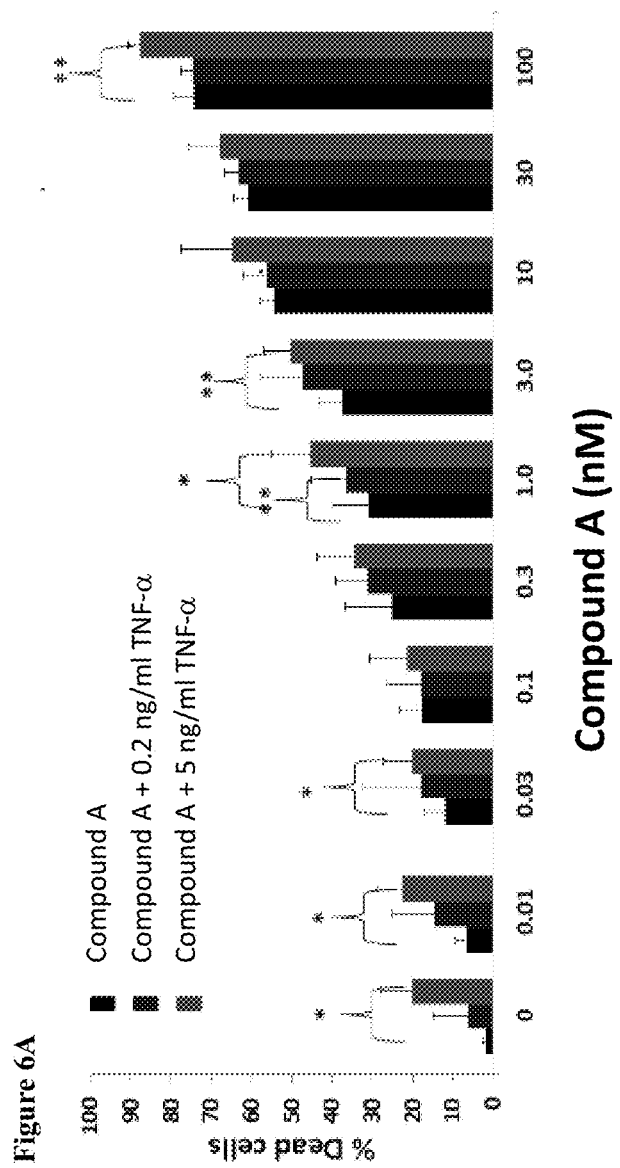
Figure 6B:
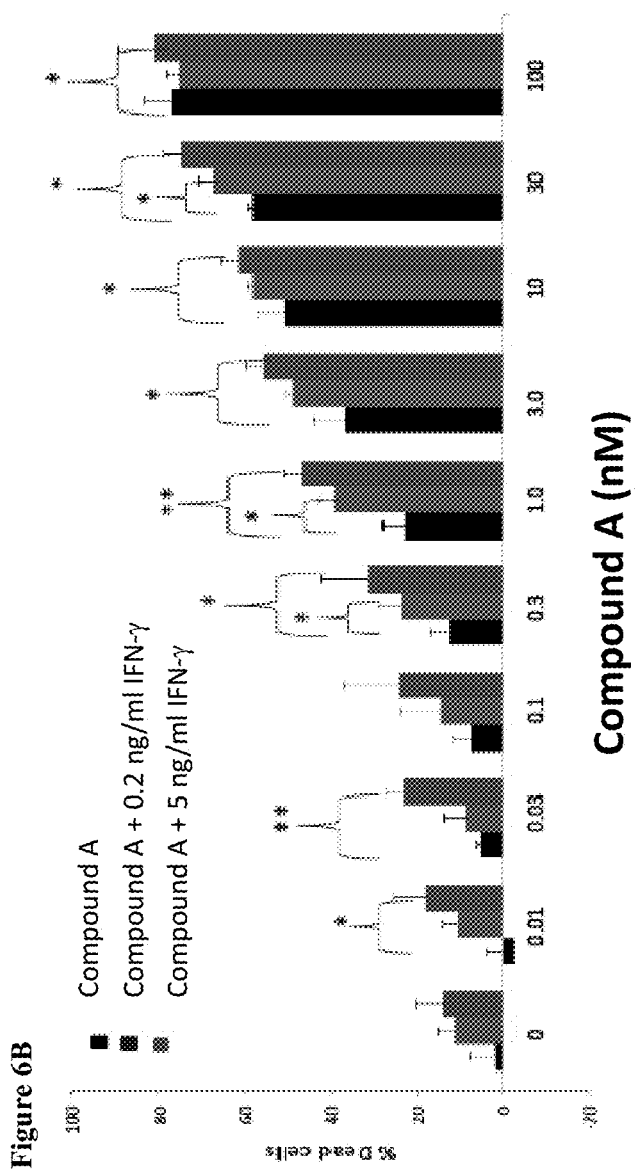

FIG. 6A shows student t-test of viability of TNF-α on BRCA1 negative (UWB1.289-2945) cell following treatment with various concentrations of Compound A. FIG. 6B shows student t-test of viability of INF-γ on BRCA1 negative cell following treatment with various concentrations of Compound A. Each data point is mean±SD from three independent determinations. ** $p<0.01$, * $p<0.05$.

Figure 7:
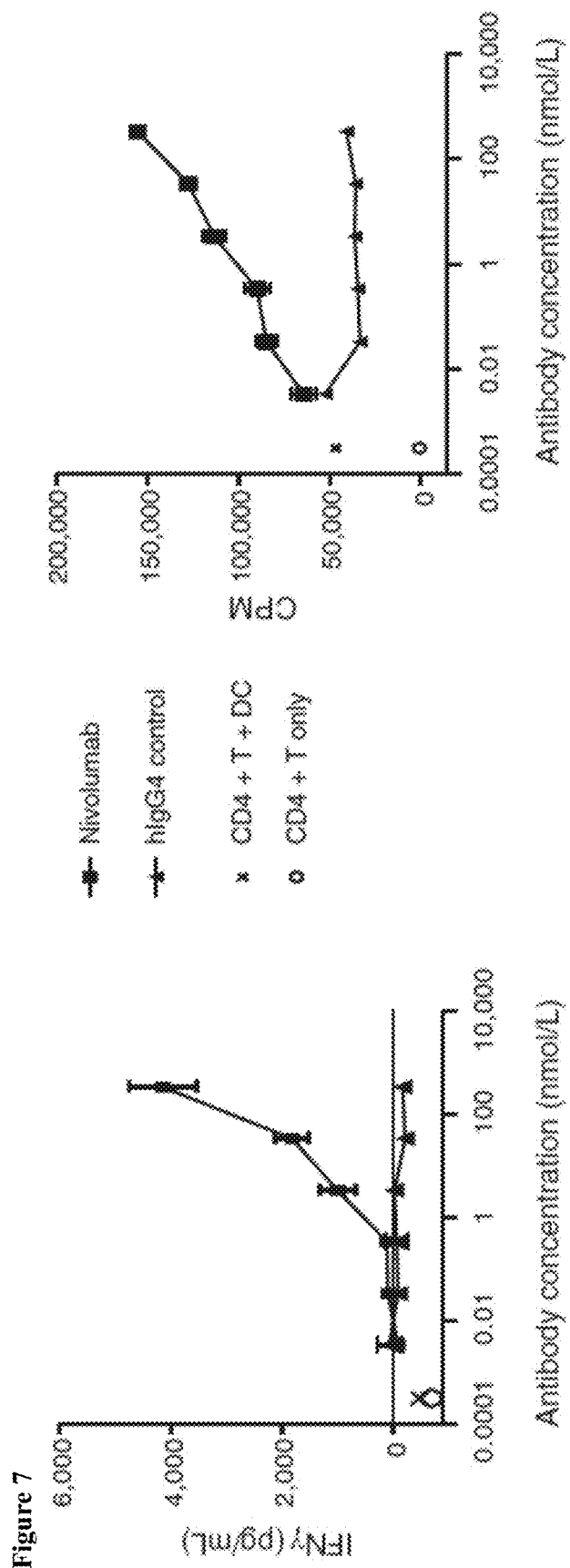

FIG. 7 shows in vitro induction of IFN-γ by nivolumab or isotype control antibody (hIgG4 control). $10^5$ purified $CD4^+$ T cells were cultured with $10^4$ allogeneic monocyte-derived dendritic cells (DCs) in the presence of a titration of nivolumab or isotype control antibody in triplicates for 6 days. Supernatants were collected at day 5 and measured for IFN-γ production by ELISA. Representative data from multiple donor DC/T-cell pairs are show. Left panel: induced IFN-γ concentration in the presence of a titration of nivolumab or isotype control antibody. Right panel: IFN-γ concentration as measured by counts per minute (CPM).

Figure 8A:
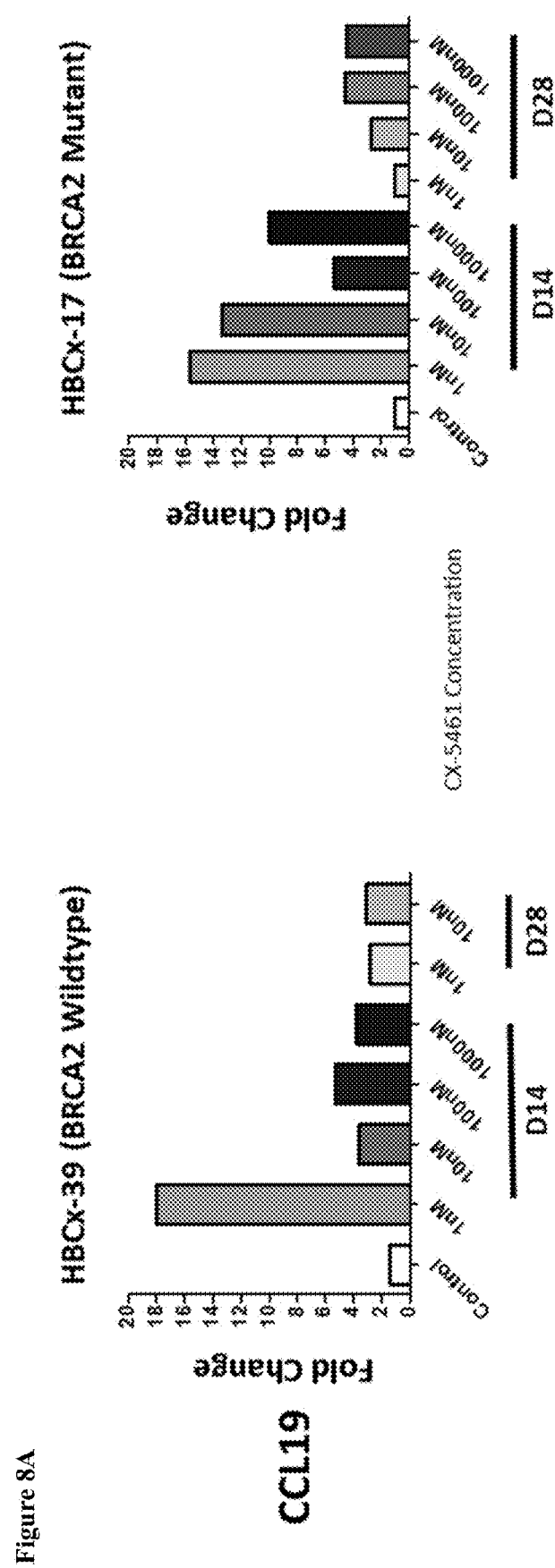
Figure 8B:
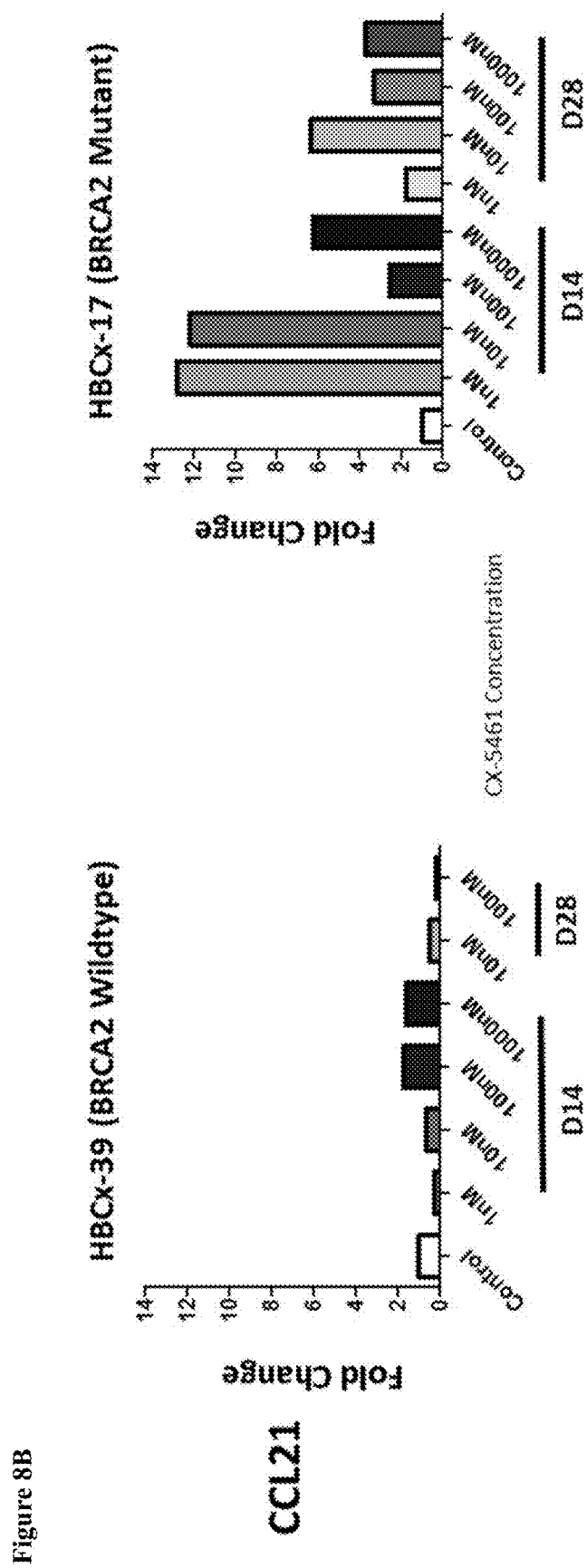
Figure 8C:
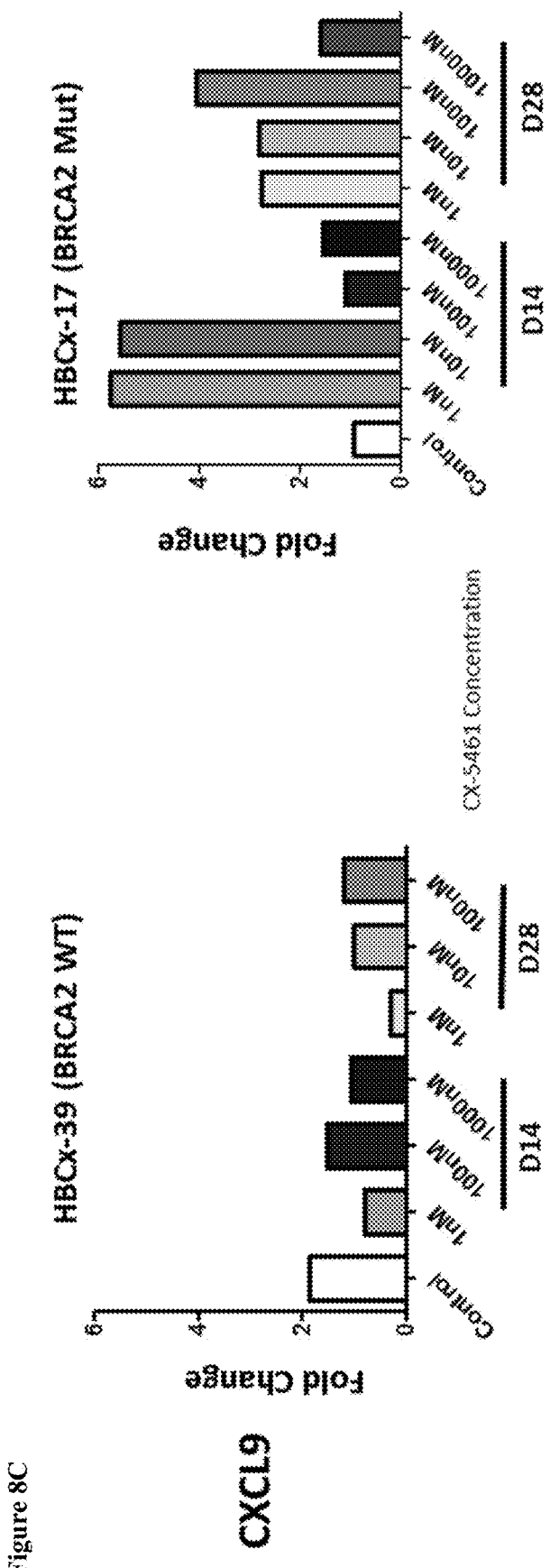

FIG. 8A-8C show effects of Compound A treatment on chemokine expressions in BRCA2 wild type (WT) and mutant (Mut) PDX-derived breast cancer cells. FIG. 8A shows fold changes of CCL19 in both WT (left panel) and Mut (right panel) in cancer cells with the treatment of a titration of Compound A at day 14 and day 28. FIG. 8B shows fold changes of CCL21 in both WT (left panel) and Mut (right panel) in cancer cells with the treatment of a titration of Compound A at day 14 and day 28. FIG. 8C shows fold changes of CXCL9 in both WT (left panel) and Mut (right panel) in cancer cells with the treatment of a titration of Compound A at day 14 and day 28.

Figure 9:
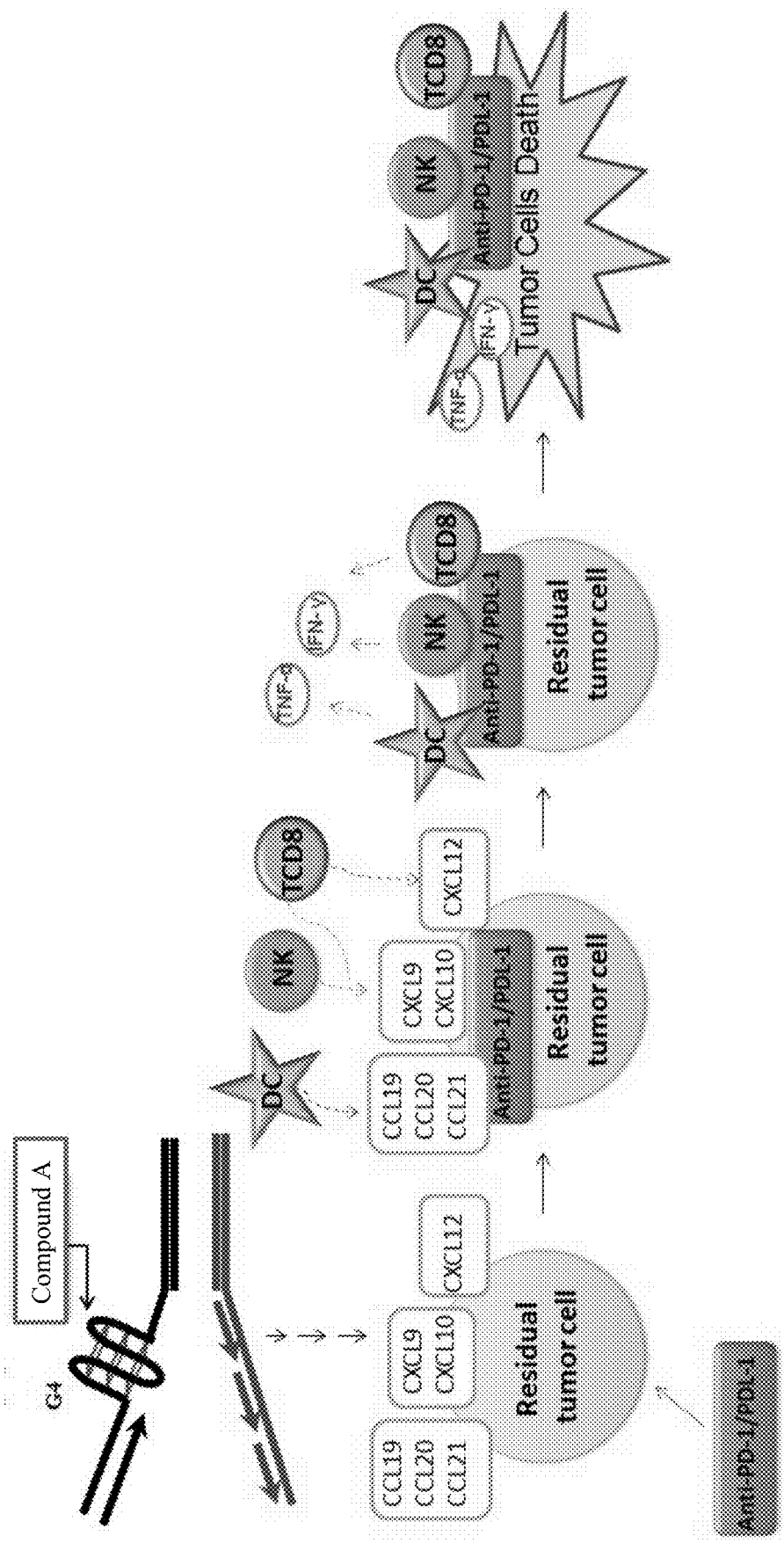

FIG. 9 shows hypothetical mechanisms by which a pharmaceutical combination comprising a compound of the present invention, such as Compound A, and an immunotherapeutic agent, such as an agent that can induce the production of endogenous cytotoxic cytokines (e.g., TNF-α and IFN-γ), such as an anti-PD-1 antibody, in treating cancer. The combination may exert potent antitumor effects through increased immunogenicity of cancer cells. Compound A includes production of chemokines such as CCL19, CCL20, CCL21, CXCL9, CXCL10, and CXCL12 in tumor cells. These chemokines in turn attract active immune cells such as DC, NK, and TCD8. These immune cells release cytotoxic compounds such as cytokines TNF-α and IFN-γ. Compound A thus enhances the cytotoxicity of TNF-α and IFN-γ which leads to tumor cells death. DC: dendritic cell; NL: natural killer cell; TCD8: CD8+ T-cell.

DETAILED DESCRIPTIONS OF THE DISCLOSURE

In patients with disorders related to proliferation of cells, such as cancers, activation of p53 protein may inhibit, alter, or reduce cell proliferation and/or induce cell apoptosis. Accordingly, by providing patients suffering from such disorders with a pharmaceutically active Pol I inhibitor that selectively activates p53 protein of the cancer and/or tumor cells can be alleviate or prevent the disorders or the progression of the disorders. The present invention provides methods, combinations, and compositions for treating a cancer or tumor which comprise the use of Compound A, or a pharmaceutically acceptable salt, ester, solvate, and/or prodrug thereof in combination with at least one additional therapeutically active agents or a therapy. In one embodiment, the present disclosure provides a combination therapy for the use of Compound A and another therapy, such as radiotherapy. In another embodiment, The present invention relates to combination therapy for Compound A and at least one additional therapeutically active agents, including immunotherapetuics, targeted therapeutics (including kinase inhibitors), and anti-angiogenics.

DEFINITIONS

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±15% or ±10%, in another example ±5%, in another example ±1%, and in yet another example ±0.1% from the specified amount, as such variations are appropriate to perform the disclosed method.

The term "compound(s) of the present invention" or "present compound(s)" refers compounds of formula (I), (IA), (IB), (II), (IIA), (III), (IIIA), and/or their subgenera, or 2-(4-Methyl-[1,4]diazepan-1-yl)-5-oxo-5H-7-thia-1,11b-diaza-benzo[c]fluorene-6-carboxylic acid (5-methyl-pyrazin-2-ylmethyl)-amide (Compound A) or isomers, N-oxides, salts, esters, solvates, prodrugs thereof. Alternatively the above terms may refer to salt form of compounds of formula (I), (IA), (IB), (II), (IIA), (III), (IIIA), and/or their subgenera, or Compound A, or solvate thereof. Compounds of formula (I), (IA), (IB), (II), (IIA), (III), (IIIA), and/or their subgenera, or Compound A described throughout the application may include any single isomer or a mixture of any number of isomers.

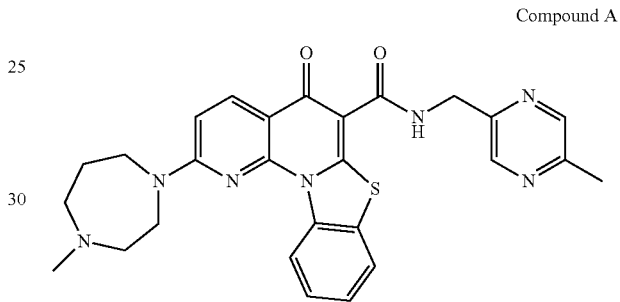

Compound A

The term "isomer" refers to compounds having the same chemical formula but may have different stereochemical formula, structural formula, or special arrangements of atoms. Examples of isomers include stereoisomers, diastereomers, enantiomers, conformational isomers, rotamers, geometric isomers, and atropisomers.

The term "N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N=O$ or $R_3N \rightarrow O$).

The term "ester" refers to any ester of a compound of the present invention in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester" includes but is not limited to pharmaceutically acceptable esters thereof. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

The term "composition" or "formulation" denotes one or more substance in a physical form, such as solid, liquid, gas, or a mixture thereof. One example of composition is a pharmaceutical composition, i.e., a composition related to, prepared for, or used in medical treatment.

The term "carboxylic acid" refers to an organic acid characterized by one or more carboxyl groups, such as acetic acid and oxalic acid. "Sulfonic acid" refers to an organic acid with the general formula of R—$(S(O)_2$—$OH)_n$, wherein R is an organic moiety and n is an integer above zero, such as 1, 2, and 3. The term "polyhydroxy acid" refers to a carboxylic acid containing two or more hydroxyl groups. Examples of polyhydroxy acid include, but are not limited to, lactobionic acid, gluconic acid, and galactose.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The terms "excipient", "carrier", and "vehicle" are used interexchangeably throughout this application and denote a substance with which a compound of the present invention is administered.

"Therapeutically effective amount" means the amount of a compound or a therapeutically active agent that, when administered to a patient for treating a disease or other undesirable medical condition, is sufficient to have a beneficial effect with respect to that disease or condition. The therapeutically effective amount will vary depending on the type of the selected compound or a therapeutically active agent, the disease or condition and its severity, and the age, weight, etc. of the patient to be treated. Determining the therapeutically effective amount of a given compound or a therapeutically active agent is within the ordinary skill of the art and requires no more than routine experimentation.

The term "combination therapy" refers to a first therapy that includes a compound of formula (I), (IA), (IB), (II), (IIA), (III), (IIIA), and/or their subgenera, or Compound A in conjunction with a second therapy (e.g., therapy, surgery and/or an additional pharmaceutical agent) useful for treating, stabilizing, preventing, and/or delaying the disease or condition. Administration in "conjunction with" another therapeutically active agent includes administration in the same or different composition(s) and/or combinations, either sequentially, simultaneously, or continuously, through the same or different routes. In some embodiments, the combination therapy optionally includes one or more pharmaceutically acceptable carriers or excipients, non-pharmaceutically active compounds, and/or inert substances.

The terms "pharmaceutical combination," "therapeutic combination" or "combination" as used herein, refers to a single dosage form comprising at least two therapeutically active agents, or separate dosage forms comprising at least two therapeutically active agents together or separately for use in combination therapy. For example, one therapeutically active agent may be formulated into one dosage form and the other therapeutically active agent may be formulated into a single or different dosage forms. For example, one therapeutically active agent may be formulated into a solid oral dosage form whereas the second therapeutically active agent may be formulated into a solution dosage form for parenteral administration.

As used herein, the terms "additional pharmaceutical agent" or "additional therapeutic agent" or "additional therapeutically active agent" with respect to the compounds described herein refers to an active agent other than the compounds of formula (I), (IA), (IB), (II), (IIA), (III), (IIIA), and/or their subgenera, or Compound A, which is administered to elicit a therapeutic effect. The pharmaceutical agent(s) may be directed to a therapeutic effect related to the condition that the compounds of the present disclosure is intended to treat or prevent (e.g., cancer) or, the pharmaceutical agent may be intended to treat or prevent a symptom of the underlying condition (e.g., tumor growth, hemorrhage, ulceration, pain, enlarged lymph nodes, cough, jaundice, swelling, weight loss, cachexia, sweating, anemia, paraneoplastic phenomena, thrombosis, etc.) or to further reduce the appearance or severity of side effects of the compounds of the present disclosure.

The term "immunotherapeutics" refers to chemicals and biologics which modulates a person's immune response to impart desirable therapeutic effect.

The term "anticancer agents" refers to chemicals and biologics which may treat, reduce, prevent, or ameliorate conditions cause by cancer or tumor growth.

The term "anti-angiogenics" or "angiogenesis inhibitors" refers to chemicals that blocks formation of new blood vessels by tumor and cancer cells (angiogenesis).

The term "radiotherapy" or "radiation therapy" refers to treatment of cancer or tumors through the use of beam of ionizing radiation, as is well known in the art.

As used herein, the phrase "a disorder characterized by cell proliferation" or "a condition characterized by cell proliferation" include, but are not limited to, cancer, benign and malignant tumors. Examples of cancer and tumors include, but are not limited to, cancers or tumor growth of the colorectum, breast, lung, liver, pancreas, lymph node, colon, prostate, brain, head and neck, skin, kidney, blood and heart (e.g., leukemia, lymphoma, carcinoma).

The terms "treat", "treating" or "treatment" in reference to a particular disease or disorder includes prevention of the disease or disorder, and/or lessening, improving, ameliorating or abrogating the symptoms and/or pathology of the disease or disorder. Generally the terms as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the terms "inhibiting" or "reducing" cell proliferation is meant to slow down, to decrease, or, for example, to stop the amount of cell proliferation, as measured using methods known to those of ordinary skill in the art, by, for example, 10%, 20%, 30%, 40%, 50%, 60%, 70%, 80%, 90%, 95%, or 100%, when compared to proliferating cells that are not subjected to the methods, compositions, and combinations of the present application.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

The term "patient" or "subject" as used herein, includes humans and animals, preferably mammals.

Compounds

The present invention provides quinolone compounds of formula (I), (IA), (IB), (II), (IIA), (III), (IIIA), and/or their subgenera, or Compound A, or salts, solvates, esters and/or prodrugs thereof. The compounds disclosed herein can be used in a combination with at least one additional therapeutically agents or therapy (combination therapy).

In one embodiment, the invention includes a compound of formula (IA),

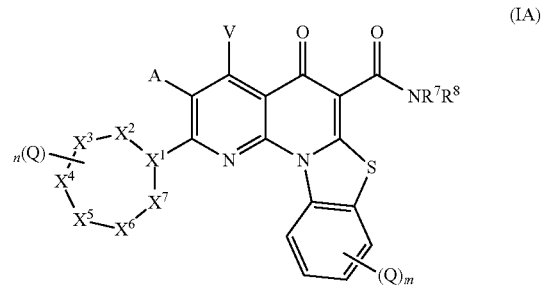

(IA)

or a pharmaceutically acceptable salt, ester, solvate and/or prodrug thereof;

wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that: (i) zero, one or two of $X^2$, $X^3$, $X^4$, $X^5$, $X^6$ and $X^7$ are $NR^4$; (ii) when $X^1$ is N, both of $X^2$ and $X^7$ are not $NR^4$; (iii) when $X^1$ is N, $X^3$ and $X^6$ are not $NR^4$; and (iv) when $X^1$ is CH and two of $X^2$, $X^3$, $X^4$, $X^5$, $X^6$ and $X^7$ are $NR^4$, the two $NR^4$ are located at adjacent ring positions or are separated by two or more other ring positions;

A and V independently are H, halo, azido, —CN, —$CF_3$, —$CONR^1R^2$, —$NR^1R^2$, —$SR^2$, —$OR^2$, —$R^3$, —W, -L—W, —$W^0$, or -L—N(R)—$W^0$;

each Q is independently halo, azido, —CN, —$CF_3$, —$CONR^1R^2$, —$NR^1R^2$, —$SR^2$, —$OR^2$, —$R^3$, —W, -L—W, —$W^0$, or -L—N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L—W or -L—N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

In some embodiments of these compounds, $X^1$ is CH and two of $X^2$, $X^3$, $X^4$, $X^5$, $X^6$ and $X^7$ are $NR^4$. In some embodiments, $X^1$ is CH and one of $X^2$, $X^3$, $X^4$, $X^5$, $X^6$ and $X^7$ are $NR^4$. In other embodiments, $X^1$ is CH and none of $X^2$, $X^3$, $X^4$, $X^5$, $X^6$ and $X^7$ are $NR^4$. In yet other embodiments, $X^1$ is N and none of $X^2$, $X^3$, $X^4$, $X^5$, $X^6$ and $X^7$ are $NR^4$. In still other embodiments, $X^1$ is N and one of $X^4$ or $X^5$ is $NR^4$.

In one embodiment, the invention provides a compound of formula (IB), (IB)

or a pharmaceutically acceptable salt, ester, solvate and/or prodrug thereof;

wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that zero, one or two of $X^2$, $X^3$, $X^4$, $X^5$, $X^6$ and $X^7$ are $NR^4$;

A and V independently are H, halo, azido, —CN, —$CF_3$, —$CONR^1R^2$, —$NR^1R^2$, —$SR^2$, —$OR^2$, —$R^3$, —W, -L—W, —$W^0$, or -L—N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L—W or -L—N(R)—$W^0$; each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

In one embodiment, the invention provides a compound of formula (I), (I)

or a pharmaceutically acceptable salt, ester, solvate and/or prodrug thereof;

wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that zero, one or two of $X^2$, $X^3$, $X^4$, $X^5$, $X^6$ and $X^7$ are $NR^4$;

A and V independently are H, halo, azido, —CN, —$CF_3$, —$CONR^1R^2$, —$NR^1R^2$, —$SR^2$, —$OR^2$, or —$R^3$;

each Q is independently halo, azido, —CN, —$CF_3$, —$CONR^1R^2$, —$NR^1R^2$, —$SR^2$, —$OR^2$, or —$R^3$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R³ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl;

R⁷ is H and R⁸ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —NR⁷R⁸, R⁷ and R⁸ together with N may form an optionally substituted azacyclic ring, optionally containing an additional heteroatom selected from N, O and S as a ring member;

m is 0, 1, 2, 3 or 4; and n is 0, 1, 2, 3, 4, or 5.

In one embodiment, the invention provides a compound of formula (IIA),

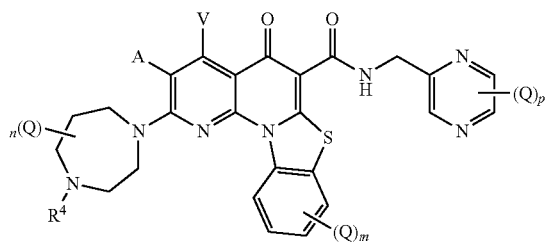

(IIA)

or a pharmaceutically acceptable salt, ester, solvate and/or prodrug thereof;

wherein:

A and V independently are H, halo, azido, —CN, —CF₃, —CONR¹R², —NR¹R², —SR², —OR², —R³, —W, -L—W, —W⁰, or -L—N(R)—W⁰;

each Q is independently halo, azido, —CN, —CF₃, —CONR¹R², —NR¹R², —SR², —OR², —R³, —W, -L-W, —W⁰, or -L-N(R)—W⁰;

in each —NR¹R², R¹ and R² together with N may form an optionally substituted azacyclic ring, optionally containing an additional heteroatom selected from N, O and S as a ring member;

R¹ is H or C1-C6 alkyl, optionally substituted with one or more halogens, or =O;

R² is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R³ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl; or R⁴ may be —W, -L—W or -L—N(R)—W⁰;

each R is independently H or C1-C6 alkyl;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W⁰ is an optionally substituted 3-4 membered carbocyclic ring, or a C1-C6 alkyl group substituted with from 1 to 4 fluorine atoms.

In one embodiment, the invention provides a compound of formula (II),

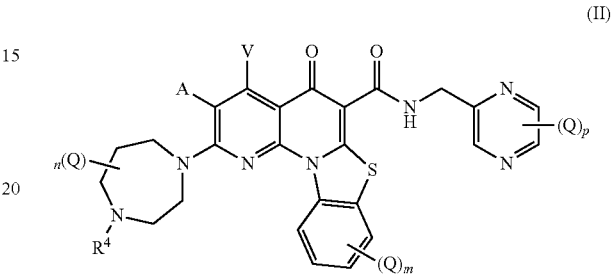

(II)

or a pharmaceutically acceptable salt, ester, solvate and/or prodrug thereof;

wherein:

A and V independently are H, halo, azido, —CN, —CF₃, —CONR¹R², —NR¹R², —SR², —OR², or —R³;

each Q is independently halo, azido, —CN, —CF₃, —CONR¹R², —NR¹R², —SR², —OR², or —R³;

in each —NR¹R², R¹ and R² together with N may form an optionally substituted azacyclic ring, optionally containing an additional heteroatom selected from N, O and S as a ring member;

R¹ is H or C1-C6 alkyl, optionally substituted with one or more halogens, or =O;

R² is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R³ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl;

m is 0, 1, 2, 3 or 4;

n is 0, 1, 2, 3, 4 or 5; and p is 0, 1, 2 or 3.

In another embodiment, the invention provides a compound of formula (IIIA),

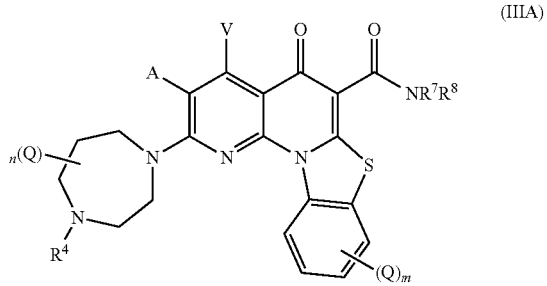

(IIIA)

or a pharmaceutically acceptable salt, ester, solvate and/or prodrug thereof;

wherein:

A and V independently are H, halo, azido, —CN, —CF$_3$, —CONR$^1$R$^2$, —NR$^1$R$^2$, —SR$^2$, —OR$^2$, —R$^3$, —W, -L—W, —W$^0$, or -L—N(R)—W$^0$;

each Q is independently halo, azido, —CN, —CF$_3$, —CONR$^1$R$^2$, —NR$^1$R$^2$, —SR$^2$, —OR$^2$, —R$^3$, —W, -L-W, —W$^0$, or -L-N(R)—W$^0$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O;

R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl; or R$^4$ may be —W, -L—W or -L—N(R)—W$^0$; each R is independently H or C1-C6 alkyl;

R$^7$ is H and R$^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —NR$^7$R$^8$, R$^7$ and R$^8$ together with N may form an optionally substituted azacyclic ring, optionally containing an additional heteroatom selected from N, O and S as a ring member;

m is 0, 1, 2, 3 or 4;

n is 0, 1, 2, 3, 4 or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W$^0$ is an optionally substituted 3-4 membered carbocyclic ring, or a C1-C6 alkyl group substituted with from 1 to 4 fluorine atoms.

In another embodiment, the invention provides a compound of formula (III),

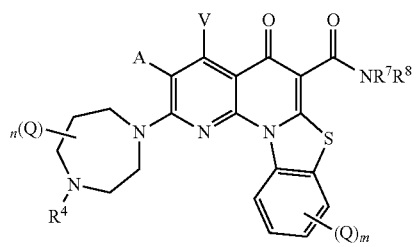

(III)

or a pharmaceutically acceptable salt, ester, solvate and/or prodrug thereof;

wherein:

A and V independently are H, halo, azido, —CN, —CF$_3$, —CONR$^1$R$^2$, —NR$^1$R$^2$, —SR$^2$, —OR$^2$, or —R$^3$;

each Q is independently halo, azido, —CN, —CF$_3$, —CONR$^1$R$^2$, —NR$^1$R$^2$, —SR$^2$, —OR$^2$, or —R$^3$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O;

R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl;

R$^7$ is H and R$^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

m is 0, 1, 2, 3 or 4; and n is 0, 1, 2, 3, 4 or 5.

In one embodiment, the disclosure provides 2-(4-Methyl-[1,4]diazepan-1-yl)-5-oxo-5H-7-thia-1,11b-diaza-benzo[c]fluorene-6-carboxylic acid (5-methyl-pyrazin-2-ylmethyl)-amide (Compound A) as shown below.

Compound A

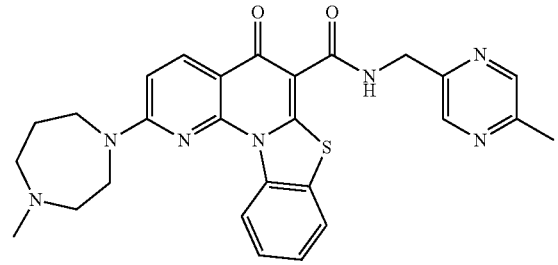

In another embodiment, the present invention provides a salt and/or solvate of Compound A.

Additional Therapeutically Active Agents

In one embodiment, the present invention provides a combination therapy comprising a compound of formula (I), (IA), (IB), (II), (IIA), (III), (IIIA), and/or their subgenera, or Compound A with at least one additional therapeutically agents or therapy. The following therapeutics, therapeutically active agents, and therapy may be employed in conjunction with the administration of the compounds described above.

Immunotherapeutics

Immunotherapy refers to a treatment of a subject afflicted with, or at risk of contracting or suffering a recurrence of, a disease by a method comprising inducing, enhancing, suppressing or otherwise modifying an immune response. In one embodiment, an immunotherapeutic disrupts, reduces or suppresses signaling from an inhibitory immunoregulator. Most immunotherapeutic approaches on their own are of limited value against majority of cancers. Reasons for this include immune regulation mediated by cancer cells and leukocyte populations through a variety of cell-expressed and secreted molecules. For example, antitumor immunity within tumor microenvironment is suppressed by a variety of tumor infiltrating leukocytes, including regulatory T cells (Treg), myeloid-derived suppressor cells (MDSC) and alternatively activated (type 2) macrophages (M2). Mechanisms employed by these cell types to suppress effective immunity include secretion of cytokines such as IL-10 and TGFβ, and expression of inhibitory receptors such as CTLA-4 and PD-L1. Tumor cells can actively inhibit immunotherapy through a number of mechanisms, such as secretion of cytokines (e.g., VEGF and TGFβ) that actively inhibit T cell recognition and destruction of tumor cells, or production of the ligand of Programmed Cell Death-1 (PD-L1) which inhibits the function of PD-1 expressed on activated T cells, see (Devaud et al., Oncolmmunology 2:8 e25961, 2013).

The present invention provides pharmaceutical combinations comprising a chemical compound described herein, such as Compound A, and at least one immunotherapeutic agent. The combinations are useful in treating or ameliorating cell proliferation disorders, such as cancers. In some embodiments, the combinations provide synergistic therapeutic effect compared to the chemical compound alone or the immunotherapeutic agent alone.

Without wishing to be bound by any particular theory, such pharmaceutical combinations are effective in treating or ameliorating cell proliferation disorders through one or more of the mechanisms described herein. In some embodiments, an immunotherapeutic agent of the present invention increases the local production of one or more cytokines that have cytotoxic effect on tumor cells. Such cytokines include, but are not limited to Tumor necrosis factor α (TNFα) and Interferon gamma (IFNγ). A chemical compound described herein, such as Compound A, can enhance the cytotoxic effect of TNF-α and/or IFN-γ, thus the combination can achieve greater therapeutic effect. In some embodiments, the chemical compound described herein, such as Compound A, can induce the production of chemokines in tumor cells, such as tumor cells with homologous recombination deficiency (e.g., tumor cells having BRCA1 and/or BRCA2 mutation). The produced chemokines in turn attract immune cells, dendritic cells (DCs), activated effector T-cells (e.g., CD8+ lymphocytes), and/or natural killer (NK) cells to tumor cells, and destruct the tumor cells. In some embodiments, the induced chemokines are CCL19, CCL20, and/or CCL21 that attract dendritic cells. In some embodiments, the induced chemokine is CX3CL1 that attracts activated effector T-cells (e.g., CD8+ lymphocytes). In some embodiments, the induced chemokines are CXCL9 and/or CXCL10 that attract activated effector T-cells (e.g., CD8+ lymphocytes) and NK cells.

In one embodiment, the immunotherapeutic agent is a monoclonal antibody, an immune effector cell, adoptive cell transfer, an immunotoxin, a vaccine, and/or a cytokine.

In one embodiment, the immunotherapeutic agent is an agent that can modulate the physiological levels of one or more cytokines in the tumor microenvironment of cancers. In one embodiment, the cytokine modulated by the immunotherapeutic is selected from one or more of the group consisting of TNF-α, IFN-γ, IL-10, TGFβ, and VEGF. In some embodiments, the immunotherapeutic agent induces production of an endogenous cytokine that has cytotoxic effect on tumor cells, such as TNF-α or IFN-γ. In some embodiments, the immunotherapeutic agent inhibits the production of an endogenous cytokine that interferes with T-cell recognition and destruction of cancer cells, such as IL-10, TGFβ, or VEGF.

In other embodiments, an immunotherapeutic agent is an agent that can induce tumor cell production of one or more chemokines that attract immune cells such as dendritic cells, effector T-cell (e.g., CD8+ lymphocytes), and/or natural killer (NK) cells to tumor cells. In some embodiments, the chemokines include, but are not limited to, CCL19, CCL20, CCL21, CX3CL1, CXCL9, and CXCL10.

In other embodiments, the immunotherapeutic agent is an agent that induces immune checkpoint blockade, such as PD-1 blockade and CTLA-4 blockade.

In some embodiments an immunotherapeutics is an antibody or an antigen-binding portion thereof that disrupts the interaction between PD-1 and PD-L1. In some embodiments, an immunotherapeutic agent is anti-PD-1 antibody, a PD-1 antagonist, an anti-PD-L1 antibody, a siRNA targeting expression of PD-1, a siRNA targeting the expression of PD-L1, or a peptide, fragment, dominant negative form, or soluble form of PD-1 or PD-L1. In one embodiment, an anti-PD-1 antibody is a monoclonal antibody and/or a humanized antibody. Cytotoxic T-lymphocyte antigen 4 (CTLA4, also known as CD152) is a member of the immunoglobulin superfamily that is expressed exclusively on T-cells. CTLA4 acts to inhibit T-cell activation and is reported to inhibit helper T-cell activity and enhance regulatory T-cell immunosuppressive activity. In some embodiments, an immunotherapeutic is an antibody that disrupts CTLA4. In other embodiments, an immunotherapeutic agent is a CTLA-4 antagonist, anti-CLTA-4 antibody, a siRNA targeting the expression of CTLA-4, or a peptide, fragment, dominant negative form, or soluble form of CTLA-4. Other immunoglobulin superfamily members include, but are not limited to, CD28, ICOS and BTLA.

In some embodiments, an immunotherapeutic agent is selected from the group consisting of anti-PD-1 antibody, nivolumab (BMS-936558, ONO-4538), lambrolizumab (MK-3475), pidilizumab (CT-011), alemtuzumab, bevacizumab, brentuximab vedotin, cetuximab, gemtuzumab ozogamicin, ibritumomab tiuxetan, ipilimumab, ofatumumab, panitumumab, rituximab, tositumomab, trastuzumab, tremelimumab, lirlumab, trevilizumab, AB134090, 11159-H03H, 11159-H08H, PA5-29572, PA5-23967, PA5-26465, MA1-12205, MA1-35914, AMP-224, MDX-1105, MEDI4736, MPDL3280A, BMS-936559, MIH1, anti-B7-H4, anti-B7-H1, anti-LAG3, BTLA, anti-Tim3, anti-B7-DC, anti-CD160, MR antagonist antibodies, anti-4-1BB, anti-OX40, anti-CD27, CD40 agonist antibodies, clone UC10-4F10-11, clone RPM1-14, clone 9D9, clone 10F.9G2, and the like, and mixtures thereof.

In one embodiment, an immunotherapeutic agent is an anti-PD-1 antibody. In another embodiment, an immunotherapeutic agent is nivolumab or pembrolizumab. In other embodiments, an immunotherapeutic agent is an anti-CTLA-4 antibody. In one embodiment, n immunotherapeutic agent is ipilimumab.

Anticancer Agents

Anticancer agents used in combination with the compounds of the present application may include agents selected from any of the classes known to those of ordinary skill in the art, including, for example, alkylating agents, anti-metabolites, plant alkaloids and terpenoids (e.g., taxanes), topoisomerase inhibitors, anti-tumor antibiotics, kinase inhibitors, hormonal therapies, molecular targeted agents, and the like. Generally such an anticancer agent is an alkylating agent, an anti-metabolite, a vinca alkaloid, a taxane, a topoisomerase inhibitor, an anti-tumor antibiotic, a tyrosine kinase inhibitor, an immunosuppressive macrolide, an Akt inhibitor, an HDAC inhibitor an Hsp90 inhibitor, an mTOR inhibitor, a PI3K/mTOR inhibitor, a PI3K inhibitor, a CDK (cyclin-dependent kinase) inhibitor, CHK (checkpoint kinase) inhibitor, PARP (poly (DP-ribose)polymerase) inhibitors, and the like.

Alkylating agents include (a) alkylating-like platinum-based chemotherapeutic agents such as cisplatin, carboplatin, nedaplatin, oxaliplatin, satraplatin, and (SP-4-3)-(cis)-amminedichloro-[2-methylpyridine] platinum(II); (b) alkyl sulfonates such as busulfan; (c) ethyleneimine and methylmelamine derivatives such as altretamine and thiotepa; (d) nitrogen mustards such as chlorambucil, cyclophosphamide, estramustine, ifosfamide, mechlorethamine, trofosamide, prednimustine, melphalan, and uramustine; (e) nitrosoureas such as carmustine, lomustine, fotemustine, nimustine, ranimustine and streptozocin; (f) triazenes and imidazotetrazines such as dacarbazine, procarbazine, temozolamide, and temozolomide.

Anti-metabolites include (a) purine analogs such as fludarabine, cladribine, chlorodeoxyadenosine, clofarabine, mercaptopurine, pentostatin, and thioguanine; (b) pyrimidine analogs such as fluorouracil, gemcitabine, capecitabine, cytarabine, azacitidine, edatrexate, floxuridine, and troxacitabine; (c) antifolates, such as methotrexate, pemetrexed, raltitrexed, and trimetrexate. Anti-metabolites also include thymidylate synthase inhibitors, such as fluorouracil, raltitrexed, capecitabine, floxuridine and pemetrexed; and ribonucleotide reductase inhibitors such as claribine, clofarabine and fludarabine.

Plant alkaloid and terpenoid derived agents include mitotic inhibitors such as the vinca alkaloids vinblastine, vincristine, vindesine, and vinorelbine; and microtubule polymer stabilizers such as the taxanes, including, but not limited to paclitaxel, docetaxel, larotaxel, ortataxel, and tesetaxel.

Topoisomerase inhibitors include topoisomerase I inhibitors such as camptothecin, topotecan, irinotecan, rubitecan, and belotecan; and topoisomerase II inhibitors such as etoposide, teniposide, and amsacrine.

Anti-tumor antibiotics include (a) anthracyclines such as daunorubicin (including liposomal daunorubicin), doxorubicin (including liposomal doxorubicin), epirubicin, idarubicin, and valrubicin; (b) streptomyces-related agents such as bleomycin, actinomycin, mithramycin, mitomycin, porfiromycin; and (c) anthracenediones, such as mitoxantrone and pixantrone. Anthracyclines have three mechanisms of action: intercalating between base pairs of the DNA/RNA strand; inhibiting topoiosomerase II enzyme; and creating iron-mediated free oxygen radicals that damage the DNA and cell membranes. Anthracyclines are generally characterized as topoisomerase II inhibitors.

Hormonal therapies include (a) androgens such as fluoxymesterone and testolactone; (b) antiandrogens such as bicalutamide, cyproterone, flutamide, and nilutamide; (c) aromatase inhibitors such as aminoglutethimide, anastrozole, exemestane, formestane, and letrozole; (d) corticosteroids such as dexamethasone and prednisone; (e) estrogens such as diethylstilbestrol; (f) antiestrogens such as fulvestrant, raloxifene, tamoxifen, and toremifine; (g) LHRH agonists and antagonists such as buserelin, goserelin, leuprolide, and triptorelin; (h) progestins such as medroxyprogesterone acetate and megestrol acetate; and (i) thyroid hormones such as levothyroxine and liothyronine.

Molecular targeted agents include (a) receptor tyrosine kinase (RTK) inhibitors, such as inhibitors of EGFR, including erlotinib, gefitinib, and neratinib; inhibitors of VEGFR including vandetanib, semaxinib, and cediranib; and inhibitors of PDGFR; further included are RTK inhibitors that act at multiple receptor sites such as lapatinib, which inhibits both EGFR and HER2, as well as those inhibitors that act at of each of C-kit, PDGFR and VEGFR, including but not limited to axitinib, sunitinib, sorafenib and toceranib; also included are inhibitors of BCR-ABL, c-kit and PDGFR, such as imatinib; (b) FKBP binding agents, such as an immunosuppressive macrolide antibiotic, including bafilomycin, rapamycin (sirolimus) and everolimus; (c) gene therapy agents, antisense therapy agents, and gene expression modulators such as the retinoids and rexinoids, e.g. adapalene, bexarotene, trans-retinoic acid, 9 cis retinoic acid, and N (4 hydroxyphenyl)retinamide; (d) phenotype-directed therapy agents, including: monoclonal antibodies such as alemtuzumab, bevacizumab, cetuximab, ibritumomab tiuxetan, rituximab, and trastuzumab; (e) immunotoxins such as gemtuzumab ozogamicin; (f) radioimmunoconjugates such as 131I-tositumomab; and (g) cancer vaccines.

Akt inhibitors include, but are not limited to, 1L6 Hydroxymethyl-chiro-inositol-2-(R)-2-O-methyl-3-O-octadecyl-sn-glycerocarbonate, SH-5 (Calbiochem Cat. No. 124008), SH-6 (Calbiochem Cat. No. Cat. No. 124009), Calbiochem Cat. No. 124011, Triciribine (NSC 154020, Calbiochem Cat. No. 124012), 10-(4'-(N-diethylamino)butyl)-2-chlorophenoxazine, Cu(II)Cl2(3-Formylchromone thiosemicarbazone), 1,3-dihydro-1-(1-((4-(6-phenyl-1H-imidazo[4,5-g]quinoxalin-7-yl)phenyl)methyl)-4-piperidinyl)-2H-benzimidazol-2-one, GSK690693 (4-(2-(4-amino-1,2,5-oxadiazol-3-yl)-1-ethyl-7-{[(3 S)-3-piperidinylmethyl]oxy}-1H-imidazo[4, 5-c]pyridin-4-yl)-2-methyl-3-butyn-2-ol), SR13668 ((2,10-dicarbethoxy-6-methoxy-5,7-dihydro-indolo[2,3-b] carbazole), GSK2141795, Perifosine, GSK21110183, XL418, XL147, PF-04691502, BEZ-235 [2-Methyl-2-[4-(3-methyl-2-oxo-8-quinolin-3-yl-2,3-dihydro-imidazo[4,5-c]quinolin-1-yl)-phenyl]-propionitrile], PX-866 ((acetic acid (1S,4E,10R, 11R,13S,14R)-[4-diallylaminomethylene-6-hydroxy-1-methoxymethyl-10,13-dimethyl-3,7,17-trioxo-1,3,4,7,10, 11,12,13,14,15,16,17-dodecahydro-2-oxa-cyclopenta[a] phenanthren-11-yl ester)), D 106669, CAL-101, GDC0941 (2-(1H-indazol-4-yl)-6-(4-methanesulfonyl-piperazin-1-yl-methyl)-4-morpholin-4-yl-thieno[3,2-d]pyrimidine), SF1126, SF1188, SF2523, TG100-115 [3-[2,4-diamino-6-(3-hydroxyphenyl)pteridin-7-yl]phenol]. A number of these inhibitors, such as, for example, BEZ-235, PX-866, D 106669, CAL 101, GDC0941, SF1126, SF2523 are also identified in the art as PI3K/mTOR inhibitors; additional examples, such as PI-103 [3-[4-(4-morpholinylpyrido[3',2': 4,5]furo[3,2-d]pyrimidin-2-yl]phenol hydrochloride] are well-known to those of skill in the art. Additional well-known PI3K inhibitors include LY294002 [2-(4-morpholinyl)-8-phenyl-4H-1-benzopyran-4-one] and wortmannin. mTOR inhibitors known to those of skill in the art include temsirolimus, deforolimus, sirolimus, everolimus, zotarolimus, and biolimus A9. A representative subset of such inhibitors includes temsirolimus, deforolimus, zotarolimus, and biolimus A9.

HDAC inhibitors include, but are not limited to, (i) hydroxamic acids such as Trichostatin A, vorinostat (suberoylanilide hydroxamic acid (SAHA)), panobinostat (LBH589) and belinostat (PXD101) (ii) cyclic peptides, such as trapoxin B, and depsipeptides, such as romidepsin (NSC 630176), (iii) benzamides, such as MS-275 (3-pyridylmethyl-N-{4-[(2-aminophenyl)-carbamoyl]-benzyl}-carbamate), CI994 (4-acetylamino-N-(2aminophenyl)-benzamide) and MGCD0103 (N-(2-aminophenyl)-4-((4-(pyridin-3-yl)pyrimidin-2-ylamino)methyl)benzamide), (iv) electrophilic ketones, (v) the aliphatic acid compounds such as phenylbutyrate and valproic acid. In one embodiment, the PI3K inhibitor is Idelalisib (CAL-101).

Hsp90 inhibitors include, but are not limited to, benzoquinone ansamycins such as geldanamycin, 17 DMAG (17-Dimethylamino-ethylamino-17-demethoxygeldanamycin), tanespimycin (17 AAG, 17-allylamino-17 demethoxygeldanamycin), EC5, retaspimycin (IPI-504, 18,21 didehydro-17-demethoxy-18,21-dideoxo-18,21-dihydroxy-17-(2 propenylamino)-geldanamycin), and herbimycin; pyrazoles such as CCT 018159 (4-[4-(2,3-dihydro-1,4-benzodioxin-6-yl)-5-methyl-1H-pyrazol-3-yl]-6-ethyl-1,3-benzenediol); macrolides, such as radicocol; as well as BIIB021 (CNF2024), SNX-5422, STA-9090, and AUY922.

CDK inhibitors include, but are not limited to, AZD-5438, BMI-1040, BMS-032, BMS-387, CVT-2584, flavopyridol, GPC-286199, MCS-5A, PD0332991, PHA-690509, seliciclib (CYC202, R-roscovitine), ZK-304709 AT7519M, P276-00, SCH 727965, AG-024322, LEEO11, LY2835219, P1446A-05, BAY 1000394, SNS-032. and the like.

CHK inhibitors include, but are not limited to, 5-(3-fluorophenyl)-3-ureidothiophene-N—[(S)-piperidin-3-yl]-2-carboxamide (AZD7762), 7-nitro-1H-indole-2-carboxylic acid {4-[1-(guanidinohydrazone)-ethyl]-phenyl}-amide (PV1019), 5-[(8-chloro-3-isoquinolinyl)amino]-3-[(1R)-2-(dimethylamino)-1-methylethoxy]-2-pyrazinecarbonitrile (SAR-020106), PF-00477736, CCT241533, 6-bromo-3-(1-methyl-1H-pyrazol-4-yl)-5-(3R)-3-piperidinyl-pyrazolo[1,5-a]pyrimidin-7-amine (SCH900776), 7-hydroxystaurosporine (UCN-01), 4-[((3 S)-1-azabicyclo[2.2.2]oct-3-yl)amino]-3-(1H-benzimidazol-2-yl)-6-chloroquinolin-2(1H)-one (CHIR 124), 7-aminodactinomycin (7-AAD), isogranulatimide, debromohymenialdisine, N-[5-Bromo-4-methyl-2-[(2 S)-2-morpholinylmethoxy]-phenyl]-N'-(5-methyl-2-pyrazinyl)urea) (LY2603618), sulforaphane (4-methylsulfinylbutyl isothiocyanate), 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078), TAT-S216A (synthetic peptide; see U.S. Pat. No. 9,415,118, incorporated herein by reference in its entirety), CBP501 (, see US20100112089A1, incorporated herein by reference in its entirety), and the like.

PARP inhibitors include, but are not limited to, 4-(3-(1-(cyclopropanecarbonyl)piperazine-4-carbonyl)-4-fluorobenzyl)phthalazin-1(2H)-one (olaparib, AZD2281, Ku-0059436), 2-[(2R)-2-methylpyrrolidin-2-yl]-1H-benzimidazole-4-carboxamide (Veliparib, ABT-888), (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (talazoparib, BMN 673), 4-iodo-3-nitrobenzamide (iniparib, BSI-201), 8-fluoro-5-(4-((methylamino)methyl)phenyl)-3,4-dihydro-2H-azepino[5,4,3-cd]indol-1(6H)-one phosphoric acid (Rucaparib, AG-014699, PF-01367338), 2-[4-[(dimethylamino)methyl]phenyl]-5,6-dihydroimidazo[4,5,1-jk][1,4]benzodiazepin-7(4H)-one (AG14361), 3-aminobenzamide (INO-1001), 2-(2-fluoro-4-((S)-pyrrolidin-2-yl)phenyl)-3H-benzo[d]imidazole-4-carboxamide (A-966492), N-(5,6-dihydro-6-oxo-2-phenanthridinyl)-2-acetamide hydrochloride (PJ34, PJ34 HCl), MK-4827, 3,4-dihydro-4-oxo-3,4-dihydro-4-oxo-N-[(1S)-1-phenylethyl]-2-quinazolinepropanamide (ME0328), 5-(2-oxo-2-phenylethoxy)-1(2H)-isoquinolinone (UPF-1069), 4-[[4-fluoro-3-[(4-methoxy-1-piperidinyl)carbonyl]phenyl]methyl]-1(2H)-phthalazinone (AZD 2461), and the like. In one embodiment, the PARP inhibitor is Olaparib.

Miscellaneous agents include altretamine, arsenic trioxide, gallium nitrate, hydroxyurea, levamisole, mitotane, octreotide, procarbazine, suramin, thalidomide, photodynamic compounds such as methoxsalen and sodium porfimer, and proteasome inhibitors such as bortezomib.

Biologic therapy agents include: interferons such as interferon-α2a and interferon-α2b, and interleukins such as aldesleukin, denileukin diftitox, and oprelvekin.

In addition to anticancer agents intended to act against cancer cells, combination therapies including the use of protective or adjunctive agents, including: cytoprotective agents such as armifostine, dexrazonxane, and mesna, phosphonates such as parmidronate and zoledronic acid, and stimulating factors such as epoetin, darbeopetin, filgrastim, PEG-filgrastim, and sargramostim, are also envisioned.

Anti-Angiogenics

Angiogenesis refers to the formation of new blood vessels. Cancer cells and tumors release chemicals which signal the growth and formation of new blood vessels. Angiogenesis plays an important in cell proliferation of cancer and tumor cells because the formations of new blood vessels allow delivery of necessary nutrition to the growing cells. Angiogenesis inhibitors are important group of chemicals because they can prevent the growth of cancer by blocking the formation of new blood vessels from surrounding tissue to a solid tumor.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Angiogenesis inhibitors may also include, but are not limited to, 2-methoxyestradiol, AG3340, prinomastat, batimastat, BAY 12-9566, carboxyamidotriazole, CC-1088, dextromethorphan acetic acid, dimethylxanthenone acetic acid, EMD 121974, endostatin, IM-862, marimastat, matrix metalloproteinase, penicillamine, PTK787/ZK 222584, RPI.4610, squalamine, squalamine lactate, 3-[2,4-dimethylpyrrol-5-yl-methyl-idenyl]-2-indolinone (SU5416), (±)-thalidomide, S-thalidomide, R-thalidomide, O-(chloroacetylcarbamoyl)fumagillol (TNP-470), combretastatin, paclitaxel, tamoxifen, COL-3, neovastat, BMS-275291, SU6668, 2-ME, interferon-alpha, anti-VEGF antibody, Medi-522 (Vitaxin II), CAI (inhibitor of calcium influx), celecoxib, Interleukin-12, IM862, amilloride, Angiostatin® protein, angiostatin K1-3, angiostatin K1-5, captopril, DL-alpha-difluoromethylornithine, DL-alpha-difluoromethylornithine HCl, His-Tag® Endostatin™ Protein, fumagillin, herbimycin A, 4-hydroxyphenylretinamide, gamma-interferon, juglone, laminin, laminin hexapeptide, laminin pentapeptide, lavendustin A, medroxyprogesterone, medroxyprogesterone acetate, minocycline, minocycline HCl, placental ribonuclease inhibitor, suramin, sodium salt Suramin, human platelet thrombospondin, tissue inhibitor of metalloproteinase 1,neutrophil granulocyte tissue inhibitor of metalloproteinase 1, rheumatoid synovial fibroblast tissue inhibitor of metalloproteinase 2, and the like.

Radiotherapy

Radiotherapy uses high-energy x-rays given as external beam radiotherapy or internal beam radiotherapy to prevent or reduce further proliferation of cancer cells or to cause apoptosis in cancer cells. Although radiotherapy can affect both cancer cells as well as healthy cells, healthy cells are better able to resist or recover from the effects of radiation.

In one embodiment, radiotherapy may be useful when administered in combination with the administration of a therapeutically effective amount of compounds of formula (I), (IA), (IB), (II), (IIA), (III), (IIIA), and/or their subgenera, or Compound A, or a pharmaceutically acceptable salt, ester, solvate and/or prodrug thereof. In some embodiments, radiotherapy may be administered before, during, or after a subject has started or ended a treatment regime comprising a therapeutically effective amount of compounds of formula (I), (IA), (IB), (II), (IIA), (III), (IIIA), and/or their subgenera, or Compound A, or a pharmaceutically acceptable salt, ester, solvate and/or prodrug thereof.

Combination Therapy

In one embodiment, the present invention provides a method of treating a condition associated with cell proliferation in a patient in need thereof. In one embodiment, the present invention provides a method of treating cancer or tumors. The method comprises co-administering to a patient in need thereof a therapeutically effective amount of at least one compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent. In some embodiment, at least one additional therapeutically active agent is selected from the group consisting of immunotherapeutics, anticancer agents, and anti-angeogenics.

In one embodiment, the compound of formula (I), (IA), (IB), (II), (IIA), (III), (IIIA), and/or their subgenera, or Compound A, or a pharmaceutically acceptable salt, ester, solvate and/or prodrug thereof, is administered at a dose from about 5 mg/day to about 500 mg/day. In one embodiment, at least one additional therapeutically active agent is administered at about 1 mg/day to about 500 mg/day.

In another embodiment, the compound of formula (I), (IA), (IB), (II), (IIA), (III), (IIIA), and/or their subgenera, or Compound A, or a pharmaceutically acceptable salt, ester, solvate and/or prodrug thereof and/or at least one additional therapeutically active agent is administered at a dose from about 1 mg/m$^2$ to about 3 g/m$^2$, from about 5 mg/m$^2$ to about 1 g/m$^2$, or from about 10 mg/m$^2$ to about 500 mg/m$^2$.

The administered dose may be expressed in units of mg/m$^2$/day in which a patient's body surface area (BSA) may be calculated in m$^2$ using various available formulae using the patient's height and weight. The administered dose may alternatively be expressed in units of mg/day which does not take into consideration the patient's BSA. It is straightforward to convert from one unit to another given a patient's height and weight.

The term "co-administration" or "coadministration" refers to administration of (a) a compound of formula (I), (IA), (IB), (II), (IIA), (III), (IIIA), and/or their subgenera, or Compound A, or a pharmaceutically acceptable salt, ester, solvate and/or prodrug thereof and (b) at least one additional therapeutically active agent, together in a coordinated fashion. For example, the co-administration can be simultaneous administration, sequential administration, overlapping administration, interval administration, continuous administration, or a combination thereof. In one embodiment, a compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent are formulated into a single dosage form. In another embodiment, formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent are provided in a separate dosage forms.

In one embodiment, the co-administration is carried out for one or more treatment cycles. By "treatment cycle", it is meant a pre-determined period of time for co-administering the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent. Typically, the patient is examined at the end of each treatment cycle to evaluate the effect of the present combination therapy. In one embodiment, the co-administration is carried out for 1 to 48 treatment cycles. In another embodiment, the co-administration is carried out for 1 to 36 treatment cycles. In another embodiment, the co-administration is carried out for 1 to 24 treatment cycles.

In one embodiment, each of the treatment cycle has about 3 or more days. In another embodiment, each of the treatment cycle has from about 3 days to about 60 days. In another embodiment, each of the treatment cycle has from about 5 days to about 50 days. In another embodiment, each of the treatment cycle has from about 7 days to about 28 days. In another embodiment, each of the treatment cycle has 28 days. In one embodiment, the treatment cycle has about 29 days. In another embodiment, the treatment cycle has about 30 days. In another embodiment, the treatment cycle has about a month-long treatment cycle. In another embodiment, the treatment cycle has from about 4 to about 6 weeks.

Depending on the patient's condition and the intended therapeutic effect, the dosing frequency for each of the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent may vary from once per day to six times per day. That is, the dosing frequency may be once per day, twice per day, three times per day, four times per day, five times per day, or six times per day. In some embodiments, dosing frequency may be one to six times per week or one to four times per month. In one embodiment, dosing frequency may be once a week, once every two weeks, once every three weeks, once every four weeks, or once a month.

There may be one or more void days in a treatment cycle. By "void day", it is meant a day when neither the compound of formula (I), (IA), (IB), (II), (IIA), (III), (IIIA), and/or their subgenera, or Compound A, or a pharmaceutically acceptable salt, ester, solvate and/or prodrug thereof or at least one therapeutically active agent is administered. In other words, none of the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent is administered on a void day. Any treatment cycle must have at least one non-void day. By "non-void day", it is meant a day when at least one of the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent is administered.

By "simultaneous administration", it is meant that the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent are administered on the same day. For the simultaneous administration, the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent can be administered at the same time or one at a time.

In one embodiment of the simultaneous administration, the compound of formula (I), (IA), (IB), (II), (IIA), (III), (IIIA), and/or their subgenera, or Compound A, or a pharmaceutically acceptable salt, ester, solvate and/or prodrug thereof, is administered from 1 to 4 times per day, 1 to 4 times per week, once every two weeks, once every three weeks, once every four weeks or 1 to 4 times per month; and the at least one additional therapeutically active agent is administered 1 to 4 times per day, 1 to 4 times per week, once every two weeks, once every three weeks, once every four weeks or 1 to 4 times per month. In another embodiment of the simultaneous administration, the compound of formula (I), (IA), (IB), (II), (IIA), (III), (IIIA), and/or their subgenera, or Compound A, or a pharmaceutically acceptable salt, ester, solvate and/or prodrug thereof, is administered once a week, once every two weeks, once every three weeks, once every four weeks, or once a month; and the at least one additional therapeutically active agent is administered 1 to 4 times per day, 1 to 4 times per week, once every two weeks, once every three weeks, once every four weeks or 1 to 4 times per month.

By "sequential administration", it is meant that during a period of two or more days of continuous co-administration without any void day, only one of the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent is administered on any given day.

In one embodiment of the sequential administration, the compound of formula (I), (IA), (IB), (II), (IIA), (III), (IIIA), and/or their subgenera, or Compound A, or a pharmaceutically acceptable salt, ester, solvate and/or prodrug thereof, is administered from 1 to 4 times per day, 1 to 4 times per week, once every two weeks, once every three weeks, once every four weeks or 1 to 4 times per month; and at least one additional therapeutically active agent is administered 1 to 4 times per day, 1 to 4 times per week, once every two weeks, once every three weeks, once every four weeks or 1 to 4 times per month. In another embodiment of the sequential administration, the compound of formula (I), (IA), (IB), (II), (IIA), (III), (IIIA), and/or their subgenera, or Compound A, or a pharmaceutically acceptable salt, ester, solvate and/or prodrug thereof, is administered from once a week, once every two weeks, once every three weeks, once every four weeks, or once a month; and at least one additional therapeutically active agent is administered 1 to 4 times per day, 1 to 4 times per week, once every two weeks, once every three weeks, once every four weeks or 1 to 4 times per month.

By "overlapping administration", it is meant that during a period of two or more days of continuous co-administration without any void day, there is at least one day of simultaneous administration and at least one day when only one of the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent is administered.

By "interval administration", it is meant a period of co-administration with at least one void day. By "continuous administration", it is meant a period of co-administration without any void day. The continuous administration may be simultaneous, sequential, or overlapping, as described above.

In the present method, the co-administration comprises oral administration, parenteral administration, or a combination thereof. Examples of the parenteral administration include, but are not limited to intravenous (IV) administration, intraarterial administration, intramuscular administration, subcutaneous administration, intraosseous administration, intrathecal administration, or a combination thereof. The compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent can be independently administered orally or parenterally. In one embodiment, the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent is administered parenterally. The parenteral administration may be conducted via injection or infusion.

In one embodiment of the present method, Compound A is provided for use in combination therapy with at least one additional therapeutically active agent. In one embodiment, the combination therapy involves co-administration on Compound A and an immunotherapeutic agent, an anticancer agent, or an anti-angiogenics. In another embodiment, the combination therapy of the present disclosure provides Compound A and at least one additional therapeutically active agent selected from nivolumab, pembrolizumab, and ipilimumab.

In one embodiment, Compound A and at least one additional therapeutically active agent are orally, subcutaneously, or intravenously administered.

Pharmaceutical Formulations

In another embodiment, the present invention provides a pharmaceutical composition and/or combination comprising a therapeutically effective amount of a compound of formula (I), (IA), (IB), (II), (IIA), (III), (IIIA), and/or their subgenera, or Compound A, or a pharmaceutically acceptable salt, ester, solvate and/or prodrug thereof, as disclosed herein, as the active ingredient, combined with a pharmaceutically acceptable excipient or carrier. The excipients are added to the formulation for a variety of purposes.

In some embodiments, the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent may be formulated into a single pharmaceutical composition and/or combination. In some embodiments, the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent are formulated into a separate pharmaceutical composition and/or combination comprising a pharmaceutically acceptable excipient or a carrier.

In one embodiment, the at least one therapeutically active agent in the single pharmaceutical composition and/or combination composition is an immunotherapeutic, anticancer agent, and/or an anti-angiogenic.

In one embodiment, the immunotherapeutic agent in the composition is a monoclonal antibody, an immune effector cell, adoptive cell transfer, an immunotoxin, a vaccine, and/or a cytokine. In one specific embodiment, the immunotherapeutic agent is cytokine. In one embodiment, the cytokine as is an immunotherapeutic is selected from TNF-α and/or IFN-γ.

In some embodiments the immunotherapeutics in the composition is an antibody or an antigen-binding portion thereof that disrupts the interaction between PD-1 and PD-L1, thereby attracting T cells to cancer cells. In some embodiments, an immunotherapeutic agent in the composition is anti-PD-1 antibody, a PD-1 antagonist, an anti-PD-L1 antibody, a siRNA targeting expression of PD-1, a siRNA targeting the expression of PD-L1, or a peptide, fragment, dominant negative form, or soluble form of PD-1 or PD-L1. In one embodiment, an anti-PD-1 antibody is a monoclonal antibody and/or a humanized antibody. Cytotoxic T-lymphocyte antigen 4 (CTLA4, also known as CD152) is a member of the immunoglobulin superfamily that is expressed exclusively on T-cells. CTLA4 acts to inhibit T-cell activation and is reported to inhibit helper T-cell activity and enhance regulatory T-cell immunosuppressive activity. In some embodiments, an immunotherapeutic in the composition is an antibody that disrupts CTLA4. In other embodiments, an immunotherapeutic agent in the composition is a CTLA-4 antagonist, anti-CLTA-4 antibody, a siRNA targeting the expression of CTLA-4, or a peptide, fragment, dominant negative form, or soluble form of CTLA-4. Other immunoglobulin superfamily members include, but are not limited to, CD28, ICOS and BTLA.

In some embodiments, the immunotherapeutic agent in the composition is selected from the group consisting of anti-PD-1 antibody, nivolumab (BMS-936558, ONO-4538), lambrolizumab (MK-3475), pidilizumab (CT-011), alemtuzumab, bevacizumab, brentuximab vedotin, cetuximab, gemtuzumab ozogamicin, ibritumomab tiuxetan, ipilimumab, ofatumumab, panitumumab, rituximab, tositumomab, trastuzumab, tremelimumab, lirlumab, trevilizumab, AB134090, 11159-H03H, 11159-H08H, PA5-29572, PA5-23967, PA5-26465, MA1-12205, MA1-35914, AMP-224, MDX-1105, MEDI4736, MPDL3280A, BMS-936559, MIH1, anti-B7-H4, anti-B7-H1, anti-LAG3, BTLA, anti-Tim3, anti-B7-DC, anti-CD160, MR antagonist antibodies, anti-4-1BB, anti-OX40, anti-CD27, CD40 agonist antibodies, clone UC10-4F10-11, clone RPM1-14, clone 9D9, clone 10F.9G2, and the like, and mixtures thereof.

In one embodiment, the immunotherapeutic agent in the composition is an anti-PD-1 antibody. In another embodiment, the immunotherapeutic agent in the composition is nivolumab or pembrolizumab. In other embodiments, the immunotherapeutic agent in the composition is an anti-CTLA-4 antibody. In one embodiment, the immunotherapeutic agent in the composition is ipilimumab.

In some embodiments, the immunotherapeutic agent in the composition is an antibody that disrupts CTLA4. In other embodiments, the immunotherapeutic agent in the composition is a CTLA-4 antagonist, anti-CLTA-4 antibody, a siRNA targeting the expression of CTLA-4, or a peptide, fragment, dominant negative form, and/or soluble form of CTLA-4. Other immunoglobulin superfamily members include, but are not limited to, CD28, ICOS and BTLA.

In some embodiments, the immunotherapeutic agent in the composition is selected from the group consisting of pidilizumab (CT-011), alemtuzumab, bevacizumab, brentuximab vedotin, cetuximab, gemtuzumab ozogamicin, ibritumomab tiuxetan, ipilimumab, ofatumumab, panitumumab, rituximab, tositumomab, trastuzumab, tremelimumab, lirlumab, trevilizumab, AB134090, 11159-H03H, 11159-H08H, PA5-29572, PA5-23967, PA5-26465, MA1-12205, MA1-35914, AMP-224, MDX-1105, MEDI4736, MPDL3280A, BMS-936559, MIH1, anti-B7-H4, anti-B7-H1, anti-LAG3, BTLA, anti-Tim3, anti-B7-DC, anti-CD160, MR antagonist antibodies, anti-4-1BB, anti-OX40, anti-CD27, CD40 agonist antibodies, clone UC10-4F10-11, clone RPM1-14, clone 9D9, clone 10F.9G2, and the like, and mixtures thereof.

In other embodiments, the immunotherapeutic agent in the composition is an anti-CTLA-4 antibody. In one embodiment, the immunotherapeutic agent in the composition is ipilimumab.

The anticancer agents in the composition of the present application may include agents selected from any of the classes known to those of ordinary skill in the art, including, for example, alkylating agents, anti-metabolites, plant alkaloids and terpenoids (e.g., taxanes), topoisomerase inhibitors, anti-tumor antibiotics, kinase inhibitors, hormonal therapies, molecular targeted agents, and the like. Generally such an anticancer agent is an alkylating agent, an antimetabolite, a vinca alkaloid, a taxane, a topoisomerase inhibitor, an anti-tumor antibiotic, a tyrosine kinase inhibitor, an immunosuppressive macrolide, an Akt inhibitor, an HDAC inhibitor an Hsp90 inhibitor, an mTOR inhibitor, a PI3K/mTOR inhibitor, a PI3K inhibitor, a CDK (cyclin-dependent kinase) inhibitor, CHK (checkpoint kinase) inhibitor, PARP (poly (DP-ribose)polymerase) inhibitors, and the like.

Alkylating agents in the composition may include (a) alkylating-like platinum-based chemotherapeutic agents such as cisplatin, carboplatin, nedaplatin, oxaliplatin, satraplatin, and (SP-4-3)-(cis)-amminedichloro-[2-methylpyridine] platinum(II); (b) alkyl sulfonates such as busulfan; (c) ethyleneimine and methylmelamine derivatives such as altretamine and thiotepa; (d) nitrogen mustards such as chlorambucil, cyclophosphamide, estramustine, ifosfamide, mechlorethamine, trofosamide, prednimustine, melphalan, and uramustine; (e) nitrosoureas such as carmustine, lomustine, fotemustine, nimustine, ranimustine and streptozocin; (f) triazenes and imidazotetrazines such as dacarbazine, procarbazine, temozolamide, and temozolomide.

Anti-metabolites in the composition may include (a) purine analogs such as fludarabine, cladribine, chlorodeoxyadenosine, clofarabine, mercaptopurine, pentostatin, and thioguanine; (b) pyrimidine analogs such as fluorouracil, gemcitabine, capecitabine, cytarabine, azacitidine, edatrexate, floxuridine, and troxacitabine; (c) antifolates, such as methotrexate, pemetrexed, raltitrexed, and trimetrexate. Anti-metabolites also include thymidylate synthase inhibitors, such as fluorouracil, raltitrexed, capecitabine, floxuridine and pemetrexed; and ribonucleotide reductase inhibitors such as claribine, clofarabine and fludarabine.

Plant alkaloid and terpenoid derived agents in the composition may include mitotic inhibitors such as the vinca alkaloids vinblastine, vincristine, vindesine, and vinorelbine; and microtubule polymer stabilizers such as the taxanes, including, but not limited to paclitaxel, docetaxel, larotaxel, ortataxel, and tesetaxel.

Topoisomerase inhibitors in the composition may include topoisomerase I inhibitors such as camptothecin, topotecan, irinotecan, rubitecan, and belotecan; and topoisomerase II inhibitors such as etoposide, teniposide, and amsacrine.

Anti-tumor antibiotics in the composition may include (a) anthracyclines such as daunorubicin (including liposomal daunorubicin), doxorubicin (including liposomal doxorubicin), epirubicin, idarubicin, and valrubicin; (b) streptomyces-related agents such as bleomycin, actinomycin, mithramycin, mitomycin, porfiromycin; and (c) anthracenediones, such as mitoxantrone and pixantrone.

Anthracyclines have three mechanisms of action: intercalating between base pairs of the DNA/RNA strand; inhibiting topoisomerase II enzyme; and creating iron-mediated free oxygen radicals that damage the DNA and cell membranes. Anthracyclines are generally characterized as topoisomerase II inhibitors.

Hormonal therapies in the composition may include (a) androgens such as fluoxymesterone and testolactone; (b) antiandrogens such as bicalutamide, cyproterone, flutamide, and nilutamide; (c) aromatase inhibitors such as aminoglutethimide, anastrozole, exemestane, formestane, and letrozole; (d) corticosteroids such as dexamethasone and prednisone; (e) estrogens such as diethylstilbestrol; (f) antiestrogens such as fulvestrant, raloxifene, tamoxifen, and toremifine; (g) LHRH agonists and antagonists such as buserelin, goserelin, leuprolide, and triptorelin; (h) progestins such as medroxyprogesterone acetate and megestrol acetate; and (i) thyroid hormones such as levothyroxine and liothyronine.

Molecular targeted agents in the composition may include (a) receptor tyrosine kinase (RTK) inhibitors, such as inhibitors of EGFR, including erlotinib, gefitinib, and neratinib; inhibitors of VEGFR including vandetanib, semaxinib, and cediranib; and inhibitors of PDGFR; further included are RTK inhibitors that act at multiple receptor sites such as lapatinib, which inhibits both EGFR and HER2, as well as those inhibitors that act at of each of C-kit, PDGFR and VEGFR, including but not limited to axitinib, sunitinib, sorafenib and toceranib; also included are inhibitors of BCR-ABL, c-kit and PDGFR, such as imatinib; (b) FKBP binding agents, such as an immunosuppressive macrolide antibiotic, including bafilomycin, rapamycin (sirolimus) and everolimus; (c) gene therapy agents, antisense therapy agents, and gene expression modulators such as the retinoids and rexinoids, e.g. adapalene, bexarotene, trans-retinoic acid, 9 cis retinoic acid, and N (4 hydroxyphenyl)retinamide; (d) phenotype-directed therapy agents, including: monoclonal antibodies such as alemtuzumab, bevacizumab, cetuximab, ibritumomab tiuxetan, rituximab, and trastuzumab; (e) immunotoxins such as gemtuzumab ozogamicin; (f) radioimmunoconjugates such as 131I-tositumomab; and (g) cancer vaccines.

Akt inhibitors in the composition may include, but are not limited to, 1L6 Hydroxymethyl-chiro-inositol-2-(R)-2-O-methyl-3-O-octadecyl-sn-glycerocarbonate, SH-5 (Calbiochem Cat. No. 124008), SH-6 (Calbiochem Cat. No. Cat. No. 124009), Calbiochem Cat. No. 124011, Triciribine (NSC 154020, Calbiochem Cat. No. 124012), 10-(4'-(N-diethylamino)butyl)-2-chlorophenoxazine, Cu(II)Cl2(3-Formylchromone thiosemicarbazone), 1,3-dihydro-1-(1-((4-(6-phenyl-1H-imidazo[4, 5-g] quinoxalin-7yl)phenyl) methyl)-4-piperidinyl)-2H-benzimidazol-2-one, GSK690693 (4-(2-(4-amino-1,2,5-oxadiazol-3-yl)-1-ethyl-7-{[(3S)-3-piperidinylmethyl]oxy}-1H-imidazo[4, 5-c]pyridin-4-yl)-2-methyl-3-butyn-2-ol), SR13668 ((2,10-dicarbethoxy-6-methoxy-5,7-dihydro-indolo[2,3-b] carbazole), GSK2141795, Perifosine, GSK21110183, XL418, XL147, PF-04691502, BEZ-235 [2-Methyl-2-[4-(3-methyl-2-oxo-8-quinolin-3-yl-2,3-dihydro-imidazo[4,5-c]quinolin-1-yl)-phenyl]-propionitrile], PX-866 ((acetic acid (1S,4E,10R, 11R,13S,14R)-[4-diallylaminomethylene-6-hydroxy-1-methoxymethyl-10,13-dimethyl-3,7,17-trioxo-1,3,4,7,10, 11,12,13,14,15,16,17-dodecahydro-2-oxa-cyclopenta[a] phenanthren-11-yl ester)), D 106669, CAL-101, GDC0941 (2-(1H-indazol-4-yl)-6-(4-methanesulfonyl-piperazin-1-yl-methyl)-4-morpholin-4-yl-thieno[3,2-d]pyrimidine), SF1126, SF1188, SF2523, TG100-115 [3-[2,4-diamino-6-(3-hydroxyphenyl)pteridin-7-yl]phenol]. A number of these inhibitors, such as, for example, BEZ-235, PX-866, D 106669, CAL 101, GDC0941, SF1126, SF2523 are also identified in the art as PI3K/mTOR inhibitors; additional examples, such as PI-103 [3-[4-(4-morpholinylpyrido[3',2':4,5]furo[3,2-d]pyrimidin-2-yl]phenol hydrochloride] are well-known to those of skill in the art. Additional well-known PI3K inhibitors in the composition may include LY294002 [2-(4-morpholinyl)-8-phenyl-4H-1-benzopyran-4-one] and wortmannin. mTOR inhibitors known to those of skill in the art include temsirolimus, deforolimus, sirolimus, everolimus, zotarolimus, and biolimus A9. A representative subset of such inhibitors in the composition may include temsirolimus, deforolimus, zotarolimus, and/or biolimus A9.

HDAC inhibitors in the composition may include, but are not limited to, (i) hydroxamic acids such as Trichostatin A, vorinostat (suberoylanilide hydroxamic acid (SAHA)), panobinostat (LBH589) and belinostat (PXD101) (ii) cyclic peptides, such as trapoxin B, and depsipeptides, such as romidepsin (NSC 630176), (iii) benzamides, such as MS-275 (3-pyridylmethyl-N-{4-[(2-aminophenyl)-carbamoyl]-benzyl}-carbamate), CI994 (4-acetylamino-N-(2aminophenyl)-benzamide) and MGCD0103 (N-(2-amino-phenyl)-4-((4-(pyridin-3-yl)pyrimidin-2-ylamino)methyl) benzamide), (iv) electrophilic ketones, (v) the aliphatic acid compounds such as phenylbutyrate and valproic acid. In one embodiment, the PI3K inhibitor in the composition is Idelalisib (CAL-101).

Hsp90 inhibitors in the composition may include, but are not limited to, benzoquinone ansamycins such as geldanamycin, 17 DMAG (17-Dimethylamino-ethylamino-17-demethoxygeldanamycin), tanespimycin (17 AAG, 17-allylamino-17 demethoxygeldanamycin), EC5, retaspimycin (IPI-504, 18,21 didehydro-17-demethoxy-18,21-dideoxo-18,21-dihydroxy-17-(2 propenylamino)-geldanamycin), and herbimycin; pyrazoles such as CCT 018159 (4-[4-(2,3-dihydro-1,4-benzodioxin-6-yl)-5-methyl-1H-pyrazol-3-yl]-6-ethyl-1,3-benzenediol); macrolides, such as radicocol; as well as BIIB021 (CNF2024), SNX-5422, STA-9090, and AUY922.

CDK inhibitors in the composition may include, but are not limited to, AZD-5438, BMI-1040, BMS-032, BMS-387, CVT-2584, flavopyridol, GPC-286199, MCS-5A, PD0332991, PHA-690509, seliciclib (CYC202, R-roscovitine), ZK-304709 AT7519M, P276-00, SCH 727965, AG-024322, LEE011, LY2835219, P1446A-05, BAY 1000394, SNS-032. and the like.

CHK inhibitors in the composition may include, but are not limited to, 5-(3-fluorophenyl)-3-ureidothiophene-N—[(S)-piperidin-3-yl]-2-carboxamide (AZD7762), 7-nitro-1H-indole-2-carboxylic acid {4-[1-(guanidinohydrazone)-ethyl]-phenyl}-amide (PV1019), 5-[(8-chloro-3-isoquinolinyl)amino]-3-[(1R)-2-(dimethylamino)-1-methylethoxy]-2-pyrazinecarbonitrile (SAR-020106), PF-00477736, CCT241533, 6-bromo-3-(1-methyl-1H-pyrazol-4-yl)-5-(3R)-3-piperidinyl-pyrazolo[1,5-a]pyrimidin-7-amine (SCH900776), 7-hydroxystaurosporine (UCN-01), 4-[((3 S)-1-azabicyclo[2.2.2]oct-3-yl)amino]-3-(1H-benz-imidazol-2-yl)-6-chloroquinolin-2(1H)-one (CHIR 124), 7-aminodactinomycin (7-AAD), isogranulatimide, debromohymenialdi sine, N-[5-Bromo-4-methyl-2-[(2S)-2-morpholinylmethoxy]-phenyl]-N'-(5-methyl-2-pyrazinyl)urea) (LY2603618), sulforaphane (4-methylsulfinylbutyl isothiocyanate), 9,10,11,12-Tetrahydro-9,12-epoxy-1H-diindolo[1, 2,3-fg:3',2',1'-kl]pyrrolo[3,4-i][1,6]benzodiazocine-1,3 (2H)-dione (SB-218078), TAT-S216A (synthetic peptide;

YGRKKRRQRRRLYRSPAMPENL), CBP501 ((d-Bpa)sws (d-Phe-F5)(d-Cha)rrrqrr), and the like.

PARP inhibitors in the composition may include, but are not limited to, 4-(3-(1-(cyclopropanecarbonyl)piperazine-4-carbonyl)-4-fluorobenzyl)phthalazin-1(2H)-one (olaparib, AZD2281, Ku-0059436), 2-[(2R)-2-methylpyrrolidin-2-yl]-1H-benzimidazole-4-carboxamide (Veliparib, ABT-888), (8S,9R)-5-fluoro-8-(4-fluorophenyl)-9-(1-methyl-1H-1,2,4-triazol-5-yl)-8,9-dihydro-2H-pyrido[4,3,2-de]phthalazin-3 (7H)-one (talazoparib, BMN 673), 4-iodo-3-nitrobenzamide (iniparib, BSI-201), 8-fluoro-5-(4-((methylamino)methyl) phenyl)-3,4-dihydro-2H-azepino[5,4,3-cd]indol-1(6H)-one phosphoric acid (Rucaparib, AG-014699, PF-01367338), 2-[4-[(dimethylamino)methyl]phenyl]-5,6-dihydroimidazo [4, 5,1-jk][1,4]benzodiazepin-7(4H)-one (AG14361), 3-aminobenzamide (INO-1001), 2-(2-fluoro-4-((S)-pyrrolidin-2-yl)phenyl)-3H-benzo[d]imidazole-4-carboxamide (A-966492), N-(5,6-dihydro-6-oxo-2-phenanthridinyl)-2-acetamide hydrochloride (PJ34, PJ34 HCl), MK-4827, 3,4-dihydro-4-oxo-3,4-dihydro-4-oxo-N-[(1S)-1-phenylethyl]-2-quinazolinepropanamide (ME0328), 5-(2-oxo-2-phenylethoxy)-1(2H)-isoquinolinone (UPF-1069), 4-[[4-fluoro-3-[(4-methoxy-1-piperidinyl)carbonyl]phenyl] methyl]-1(2H)-phthalazinone (AZD 2461), and the like. In one embodiment, the PARP inhibitor in the composition is Olaparib.

Other miscellaneous agents in the composition may include altretamine, arsenic trioxide, gallium nitrate, hydroxyurea, levamisole, mitotane, octreotide, procarbazine, suramin, thalidomide, photodynamic compounds such as methoxsalen and sodium porfimer, and proteasome inhibitors such as bortezomib.

Biologic therapy agents in the composition may include: interferons such as interferon-α2a and interferon-α2b, and interleukins such as aldesleukin, denileukin diftitox, and oprelvekin.

In addition to anticancer agents intended to act against cancer cells, combination therapies including the use of protective or adjunctive agents in the composition, including: cytoprotective agents such as armifostine, dexrazonxane, and mesna, phosphonates such as parmidronate and zoledronic acid, and stimulating factors such as epoetin, darbeopetin, filgrastim, PEG-filgrastim, and sargramostim, are also envisioned.

Angiogenesis inhibitors in the composition may include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Angiogenesis inhibitors in the composition may also include, but are not limited to, 2-methoxyestradiol, AG3340, prinomastat, batimastat, BAY 12-9566, carboxyamidotriazole, CC-1088, dextromethorphan acetic acid, dimethylxanthenone acetic acid, EMD 121974, endostatin, IM-862, marimastat, matrix metalloproteinase, penicillamine, PTK787/ZK 222584, RPI.4610, squalamine, squalamine lactate, 3-[2,4-dimethylpyrrol-5-yl-methyl-idenyl]-2-indolinone (SU5416), (+)-thalidomide, S-thalidomide, R-thalidomide, O-(chloroacetylcarbamoyl)fumagillol (TNP-470), combretastatin, paclitaxel, tamoxifen, COL-3, neovastat, BMS-275291, SU6668, 2-ME, interferon-alpha, anti-VEGF antibody, Medi-522 (Vitaxin II), CAI (inhibitor of calcium influx), celecoxib, Interleukin-12, IM862, amiloride, Angiostatin® protein, angiostatin K1-3, angiostatin K1-5, captopril, DL-alpha-difluoromethylornithine, DL-alpha-difluoromethylornithine HCl, His-Tag® Endostatin™ Protein, fumagillin, herbimycin A, 4-hydroxyphenylretinamide, gamma-interferon, juglone, laminin, laminin hexapeptide, laminin pentapeptide, lavendustin A, medroxyprogesterone, medroxyprogesterone acetate, minocycline, minocycline HCl, placental ribonuclease inhibitor, suramin, sodium salt Suramin, human platelet thrombospondin, tissue inhibitor of metalloproteinase 1,neutrophil granulocyte tissue inhibitor of metalloproteinase 1, rheumatoid synovial fibroblast tissue inhibitor of metalloproteinase 2, and the like.

In a specific embodiment, Compound A, or a pharmaceutically acceptable salt, ester, solvate and/or prodrug thereof and at least one therapeutically active agent may be formulated into a single pharmaceutical composition and/or combination composition. In another embodiment, the composition may comprise Compound A, or a pharmaceutically acceptable salt, ester, solvate and/or prodrug thereof, as disclosed herein, in an amount of about 5 mg to about 500 mg. In another embodiment, the amount is about 20 mg to about 400 mg. In another embodiment, the amount is about 50 mg to about 300 mg. In another embodiment, the amount is about 100 mg to about 200 mg.

In another embodiment, the composition may comprise Compound A, or a pharmaceutically acceptable salt, ester, solvate and/or prodrug thereof, and a PARP inhibitor. In another embodiment, the PARP inhibitor is Olaparib.

In another embodiment, the composition may comprise Compound A, or a pharmaceutically acceptable salt, ester, solvate and/or prodrug thereof and Olaparib, wherein the amount of Olaparib in the composition is about 10 mg to about 800 mg. In another embodiment, the amount of Olaparib is about 20 mg to about 600 mg. In another embodiment, the amount of Olaparib is about 100 mg to about 500 mg. In another embodiment, the amount of Olaparib is about 300 mg to about 400 mg.

In another embodiment, the composition may comprise Compound A, or a pharmaceutically acceptable salt, ester, solvate and/or prodrug thereof, and a PI3K inhibitor. In another embodiment, the PI3K inhibitor is Idelalisib.

In another embodiment, the composition may comprise Compound A, or a pharmaceutically acceptable salt, ester, solvate and/or prodrug thereof and Idelalisib, wherein the amount of Idelalisib in the composition is about 10 mg to about 500 mg. In another embodiment, the amount of Idelalisib is about 40 mg to about 300 mg. In another embodiment, the amount of Idelalisib is about 75 mg to about 200 mg. In another embodiment, the amount of Idelalisib is about 100 mg to about 175 mg.

In another embodiment, the composition may comprise Compound A, or a pharmaceutically acceptable salt, ester, solvate and/or prodrug thereof, and one or more immunotherapeutic agent that induces endogenous production of cytokines. In another embodiment, the cytokines are TNF-α and/or IFN-γ.

In another embodiment, the composition may comprise Compound A, or a pharmaceutically acceptable salt, ester, solvate and/or prodrug thereof and an immunotherapeutic agent that induces endogenous production of TNF-α, wherein the amount of induced TNF-α in the tumor microenvironment (e.g., the physiological level as measured by ELISA) is about is about 0.01 ng/ml to about 20 ng/ml. In another embodiment, the amount of TNF-α is about 0.1 ng/ml to about 10 ng/ml. In another embodiment, the amount of TNF-α is about 0.2 ng/ml to about 5 ng/ml. In another embodiment, the amount of TNF-α is about 0.5 ng/ml to about 2 ng/ml. The induced amount of TNF-α can be determined by any suitable method, such as enzyme-linked immunosorbent assay (ELISA).

In another embodiment, the composition may comprise Compound A, or a pharmaceutically acceptable salt, ester, solvate and/or prodrug thereof and an immunotherapeutic agent that induces endogenous production of IFN-γ, wherein the amount of induced IFN-γ in the tumor microenvironment (e.g., the physiological level as measured by ELISA) is about is about 0.01 ng/ml to about 20 ng/ml. In another embodiment, the amount of IFN-γ is about 0.1 ng/ml to about 10 ng/ml. In another embodiment, the amount of IFN-γ is about 0.2 ng/ml to about 5 ng/ml. In another embodiment, the amount of IFN-γ is about 0.5 ng/ml to about 2 ng/ml. The induced amount of IFN-γ can be determined by any suitable method, such as enzyme-linked immunosorbent assay (ELISA).

In another embodiment, the composition may comprise Compound A, or a pharmaceutically acceptable salt, ester, solvate and/or prodrug thereof, and an immunotherapeutic agent that induces endogenous secretion of TNF-α, and IFN-γ in the ranges described above.

In another embodiment, the composition may comprise Compound A, or a pharmaceutically acceptable salt, ester, solvate and/or prodrug thereof, and an immunotherapeutic agent that induces endogenous secretion of TNF-α, and/or IFN-γ in the ranges described above, wherein the immunotherapeutic agent is a PD-1 inhibitor. In another embodiment, the composition may comprise Compound A, or a pharmaceutically acceptable salt, ester, solvate and/or prodrug thereof, and an immunotherapeutic agent that induces endogenous secretion of TNF-α, and/or IFN-γ in the ranges described above, wherein the PD-1 inhibitor is nivolumab. In a specific embodiment, the concentration of nivolumab in the composition is about 1 mg/mL to about 50 mg/mL. In another embodiment, the concentration is about 2.5 mg/mL to about 25 mg/mL. In another embodiment, the concentration is about 5 mg/mL to about 15 mg/mL. In another embodiment, the amount of nivolumab in the composition is about 25 mg to about 1,000 mg. In another embodiment, the amount of nivolumab in the composition is about 50 mg to about 500 mg. In another embodiment, the amount of nivolumab in the composition is about 150 mg to about 300 mg.

Pharmaceutical acceptable excipients may be added to the composition/formulation. For example, diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions and/or combinations that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition and/or combination in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition and/or combination, the composition and/or combination is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions and/or combinations may also be dyed using any pharmaceutically acceptable colorant to improve their appearance and/or facilitate patient identification of the product and unit dosage level.

In liquid pharmaceutical compositions and/or combinations may be prepared using the compound of formula (I), (IA), (IB), (II), (IIA), (III), (IIIA), and/or their subgenera, or Compound A, or a pharmaceutically acceptable salt, ester, solvate and/or prodrug thereof, of the present invention and any other solid excipients where the components are dissolved or suspended in a liquid carrier such as water, vegetable oil, alcohol, polyethylene glycol, propylene glycol, or glycerin.

Liquid pharmaceutical compositions and/or combinations may contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions and/or combinations may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition and/or combination may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions and/or combination of the present invention include powders, granulates, aggregates and compacted compositions and/or combinations. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions, aerosols and elixirs.

The dosage form of the present invention may be a capsule containing the composition and/or combination, preferably a powdered or granulated solid composition and/or combination of the invention, within either a hard or soft shell. The shell may be made from gelatin and optionally contain a plasticizer such as glycerin and sorbitol, and an opacifying agent or colorant.

A composition and/or combination for tableting or capsule filling may be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may be tableted, or other excipients may be added prior to tableting, such as a glidant and/or a lubricant.

A tableting composition and/or combination may be prepared conventionally by dry blending. For example, the blended composition and/or combination of the actives and excipients may be compacted into a slug or a sheet and then comminuted into compacted granules. The compacted granules may subsequently be compressed into a tablet.

As an alternative to dry granulation, a blended composition and/or combination may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting; however, they are not subjected to a final tableting step.

The active ingredient and excipients may be formulated into compositions and/or combinations and dosage forms according to methods known in the art.

In one embodiment, a dosage form may be provided as a kit comprising a compound of formula (I), (IA), (IB), (II), (IIA), (III), (IIIA), and/or their subgenera, or Compound A, or a pharmaceutically acceptable salt, ester, solvate and/or prodrug thereof and pharmaceutically acceptable excipients and carriers as separate components. In one embodiment, a dosage form may be provided as a kit comprising compound of formula (I), (IA), (IB), (II), (IIA), (III), (IIIA), and/or their subgenera, or Compound A, or a pharmaceutically acceptable salt, ester, solvate and/or prodrug thereof, at least one additional therapeutically active agent, and pharmaceutically acceptable excipients and carriers as separate components. In some embodiments, the dosage form kit allow physicians and patients to formulate an oral solution or injection solution prior to use by dissolving, suspending, or mixing the compound of formula (I), (IA), (IB), (II), (IIA), (III), (IIIA), and/or their subgenera, or a pharmaceutically acceptable salt, ester, solvate and/or prodrug thereof with pharmaceutically acceptable excipients and carriers. In one embodiment, a dosage form kit which provides a compound of formula (I), (IA), (IB), (II), (IIA), (III), (IIIA), and/or their subgenera, or Compound A, or a pharmaceutically acceptable salt, ester, solvate and/or prodrug thereof which has improved stability when compared to pre-formulated formulations a compound of formula (I), (IA), (IB), (II), (IIA), (III), (IIIA), and/or their subgenera, or Compound A, or a pharmaceutically acceptable salt, ester, solvate and/or prodrug thereof.

In one embodiment, a compound of formula (I), (IA), (IB), (II), (IIA), (III), (IIIA), and/or their subgenera, or Compound A, or a pharmaceutically acceptable salt, ester, solvate and/or prodrug thereof is used in the formulation. The compound of formula (I), (IA), (IB), (II), (IIA), (III), (IIIA), and/or their subgenera, or Compound A, or a pharmaceutically acceptable salt, ester, solvate and/or prodrug thereof, of the present invention may be used in pharmaceutical formulations or compositions and/or combinations as single components or mixtures together with other forms of a compound of formula (I), (IA), (IB), (II), (IIA), (III), (IIIA), and/or their subgenera, or Compound A. In one embodiment, pharmaceutical formulations or compositions and/or combinations of the present invention contain 25-100% or 50-100% by weight, of at least one compound of formula (I), (IA), (IB), (II), (IIA), (III), (IIIA), and/or their subgenera, or Compound A, or a pharmaceutically acceptable salt, ester, solvate and/or prodrug thereof, as described herein, in the formulation or composition and/or combination.

Therapeutic Use

The present invention also provides treatment of disorders related to proliferation of cells. In one embodiment, there is provided a method for selectively activating p53 protein comprising contacting a cell afflicted by disorder related to cell proliferation with the present compound. In one embodiment, the method comprises contacting cancer and/or tumor cells with the compound of formula (I), (IA), (IB), (II), (IIA), (III), (IIIA), and/or their subgenera, or Compound A, or a pharmaceutically acceptable salt, ester, solvate and/or prodrug thereof, as disclosed herein. In another embodiment, the method comprises contacting cancer and/or tumor cells with the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent, as disclosed herein.

In another embodiment, the method of contacting cancer and/or tumor cells with the compound of formula (I), (IA), (IB), (II), (IIA), (III), (IIIA), and/or their subgenera, or Compound A, or a pharmaceutically acceptable salt, ester, solvate and/or prodrug thereof, as disclosed herein, may induce cell apoptosis or alleviate or prevent the progression of the disorder. In one embodiment, the method of contacting cancer and/or tumor cells with the compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent, as disclosed herein, may induce cell apoptosis or alleviate or prevent the progression of the disorder.

In another embodiment, the method of contacting cancer and/or tumor cells with the compound of formula (I), (IA), (IB), (II), (IIA), (III), (IIIA), and/or their subgenera, or Compound A, or a pharmaceutically acceptable salt, ester, solvate and/or prodrug thereof, as disclosed herein, may reduce the incidence of cancer and/or tumor growth. Additionally, disclosed are methods for treating cancers, cancer cells, tumors, or tumor cells. Non limiting examples of cancer that may be treated by the methods of this disclosure include cancer or cancer cells of: colorectum, breast, ovary, cervix, lung, liver, pancreas, lymph node, colon, prostate, brain, head and neck, skin, kidney, bone (e.g., Ewing's sarcoma) and blood and heart (e.g., leukemia, lymphoma, carcinoma). Non limiting examples of tumors that may be treated by the methods of this disclosure include tumors and tumor cells of: colorectum, breast, ovary, cervix, lung, liver, pancreas, lymph node, colon, prostate, brain, head and neck, skin, kidney, bone (e.g., Ewing's sarcoma) and blood and heart (e.g., leukemia, lymphoma, carcinoma).

In one embodiment, the present invention provides a method of reducing or inhibiting cell proliferation, and/or a method of treating cancer comprising co-administering to a patient in need thereof a therapeutically effective amount of at least one compound of formula (I), (IA), (IB), (II), (IIA), (III), (IIIA), and/or their subgenera, or Compound A, or a pharmaceutically acceptable salt, ester, solvate and/or prodrug thereof and a PI3K inhibitor. In one embodiment of various methods disclosed herein, a co-administration comprises Compound A and a PI3K inhibitor. In one embodiment, a co-administration for any method disclosed herein comprises Compound A and Idelalisib.

In one embodiment, the present invention provides a method of reducing or inhibiting cell proliferation, and/or a method of treating cancer comprising co-administering to a patient in need thereof a therapeutically effective amount of at least one compound of formula (I), (IA), (IB), (II), (IIA), (III), (IIIA), and/or their subgenera, or Compound A, or a pharmaceutically acceptable salt, ester, solvate and/or prodrug thereof and a PARP inhibitor. In one embodiment of various methods disclosed herein, a co-administration comprises Compound A and PARP inhibitor. In one embodiment, a co-administration for any method disclosed herein comprises Compound A and Olaparib.

In one embodiment, the present invention provides a method of reducing or inhibiting cell proliferation, and/or a method of treating cancer comprising co-administering to a patient in need thereof a therapeutically effective amount of at least one compound of formula (I), (IA), (IB), (II), (IIA), (III), (IIIA), and/or their subgenera, or Compound A, or a pharmaceutically acceptable salt, ester, solvate and/or prodrug thereof and cytokines. In one embodiment of various methods disclosed herein, a co-administration comprises Compound A and cytokines. In one embodiment, a co-administration for any method disclosed herein comprises Compound A and TNF-α. In another embodiment, a co-administration for any method disclosed herein comprises Compound A and IFN-γ. In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof and at least one therapeutically active agent in a single pharmaceutical composition and/or combination composition. In one embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof, as disclosed herein, in an amount of about 5 mg to about 500 mg. In another embodiment, the amount is about 20 mg to about 400 mg. In another embodiment, the amount is about 50 mg to about 300 mg. In another embodiment, the amount is about 100 mg to about 200 mg.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof, and a PARP inhibitor. In another embodiment, the PARP inhibitor is Olaparib.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof and Olaparib, wherein the amount of Olaparib in the composition is about 10 mg to about 800 mg. In another embodiment, the amount of Olaparib is about 20 mg to about 600 mg. In another embodiment, the amount of Olaparib is about 100 mg to about 500 mg. In another embodiment, the amount of Olaparib is about 300 mg to about 400 mg.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof, and a PI3K inhibitor. In another embodiment, the PI3K inhibitor is Idelalisib.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof and Idelalisib, wherein the amount of Idelalisib in the composition is about 10 mg to about 500 mg. In another embodiment, the amount of Idelalisib is about 40 mg to about 300 mg. In another embodiment, the amount of Idelalisib is about 75 mg to about 200 mg. In another embodiment, the amount of Idelalisib is about 100 mg to about 175 mg.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof, and an immunotherapeutic agent that modulates the endogenous secretion of one or more cytokines. In another embodiment, the cytokines are TNF-α and/or IFN-γ.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof and an immunotherapeutic agent that induces endogenous secretion of TNF-α, wherein the amount of induced TNF-α is about 0.01 ng/ml to about 20 ng/ml. In another embodiment, the amount of induced TNF-α is about 0.1 ng/ml to about 10 ng/ml. In another embodiment, the amount of induced TNF-α is about 0.2 ng/ml to about 5 ng/ml. In another embodiment, the amount of induced TNF-α is about 0.5 ng/ml to about 2 ng/ml. The amount of induced endogenous production of TNF-α can be quantified by any suitable method, such as ELISA.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof and an immunotherapeutic agent that induces endogenous secretion of IFN-γ, wherein the amount of induced IFN-γ is about 0.01 ng/ml to about 20 ng/ml. In another embodiment, the amount of induced IFN-γ is about 0.1 ng/ml to about 10 ng/ml. In another embodiment, the amount of induced IFN-γ is about 0.2 ng/ml to about 5 ng/ml. In another embodiment, the amount of induced IFN-γ is about 0.5 ng/ml to about 2 ng/ml. The amount of induced endogenous production of IFN-γ can be quantified by any suitable method, such as ELISA.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof, and an immunotherapeutic agent that induces endogenous secretion of TNF-α, and/or IFN-γ in the ranges described above.

In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof, and an immunotherapeutic agent that induces endogenous secretion of TNF-α, and/or IFN-γ in the ranges described above, wherein the immunotherapeutic agent is a PD-1 inhibitor. In another embodiment, the methods may include reducing or inhibiting cell proliferation, and/or a method of treating cancer comprising co-administering to a patient in need thereof a therapeutically effective amount of Compound A, or a pharmaceutically acceptable salt, ester, solvate and/or prodrug thereof, and an immunotherapeutic agent that induces endogenous secretion of TNF-α, and/or IFN-γ in the ranges described above, wherein the PD-1 inhibitor is nivolumab. In a specific embodiment, the concentration of nivolumab in the composition is about 1 mg/mL to about 50 mg/mL. In another embodiment, the concentration is about 2.5 mg/mL to about 25 mg/mL. In another embodiment, the concentration is about 5 mg/mL to about 15 mg/mL. In another embodiment, the amount of nivolumab in the composition is about 25 mg to about 1,000 mg. In another embodiment, the amount of nivolumab in the composition is about 50 mg to about 500 mg. In another embodiment, the amount of nivolumab in the composition is about 150 mg to about 300 mg.

In one embodiment, the co-administration of Compound A, or a pharmaceutically acceptable salt, ester, solvate and/or prodrug thereof, with Olaparib, Idelalisib, or an immunotherapeutic agent that induces endogenous secretion of TNF-α and/or IFN-γ to a patient in thereof may be performed once daily, twice daily, three times daily, four times daily, five times daily, six times daily, seven times daily, eight times daily, nine times daily, or ten times daily.

In some embodiments, the cancer that can be treated by the methods provided in this disclosure is a homologous recombination dependent deoxyribonucleic acid double strand break repair (HR dependent DNA DSB repair) deficient cancer, also referred to as HRD cancer. In some embodiments, HR dependent DNA DSB repair deficient cancer is identified by determining the HR dependent DNA DSB repair activity of cancer cells obtained from subject.

In one embodiment, compositions and/or combinations disclosed herein is useful for treating HRD cancer. In one embodiment, co-administering of an effective amount of at least one compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent can be useful for treating HRD cancer. In another embodiment, co-administering of an effective amount of at least one compound of formula (I), (IA), (IB), (II), (IIA), (III), (IIIA), and/or their subgenera, or Compound A, or a pharmaceutically acceptable salt, ester, solvate and/or prodrug thereof and at least one therapeutically active agent selected from PI3K inhibitor, PARP inhibitor, and cytokines can be useful for treating HRD cancer. In another embodiment, co-administration of Compound A and at least one therapeutically active agent selected from PI3K inhibitor, PARP inhibitor, and cytokines can be useful for treating HRD cancer.

The present invention also provides methods of treating, preventing, ameliorating and/or alleviating the progression of disorders or conditions characterized by cell proliferation in a subject. More particularly, the methods of the present invention involve administration of an effective amount of the quinolone compounds described herein, in a subject to treat a disorder or a condition characterized by cell proliferation. The compound of formula (I), (IA), (IB), (II), (IIA), (III), (IIIA), and/or their subgenera, or Compound A, or a pharmaceutically acceptable salt, ester, solvate and/or prodrug thereof, can be administered in an amount effective selectively activate p53 proteins in cancer and/or tumor cells, which may lead to cell death or apoptosis. The terms "subject" and "patient" are used interchangeably throughout the present application.

As used herein, administering can be effected or performed using any of the various methods known to those skilled in the art. The compound of formula (I), (IA), (IB), (II), (IIA), (III), (IIIA), and/or their subgenera, or Compound A, or a pharmaceutically acceptable salt, ester, solvate and/or prodrug thereof, can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed compound of formula (I), (IA), (IB), (II), (IIA), (III), (IIIA), and/or their subgenera, or Compound A, or a pharmaceutically acceptable salt, ester, solvate and/or prodrug thereof, can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the compound of formula (I), (IA), (IB), (II), (IIA), (III), (IIIA), and/or their subgenera, or Compound A, or a pharmaceutically acceptable salt, ester, solvate and/or prodrug thereof, is administered (e.g., syrup, elixir, capsule, tablet, foams, emulsion, gel, etc.) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The compound of formula (I), (IA), (IB), (II), (IIA), (III), (IIIA), and/or their subgenera, or Compound A, or a pharmaceutically acceptable salt, ester, solvate and/or prodrug thereof, can also be used to coat bioimplantable materials to enhance neurite outgrowth, neural survival, or cellular interaction with the implant surface. The compound of formula (I), (IA), (IB), (II), (IIA), (III), (IIIA), and/or their subgenera, or Compound A, or a pharmaceutically acceptable salt, ester, solvate and/or prodrug thereof, disclosed herein can be administered together with other biologically active agents, such as anticancer agents, analgesics, anti-inflammatory agents, anesthetics and other agents which can control one or more symptoms or causes of a disorder or a condition characterized by cell proliferation.

In one embodiment, the compound of formula (I), (IA), (IB), (II), (IIA), (III), (IIIA), and/or their subgenera, or Compound A, or a pharmaceutically acceptable salt, ester, solvate and/or prodrug thereof and additional therapeutically active agent can be administered together with a second therapeutically active agent or more. In one embodiment, the second therapeutically active agent is an anticancer agent. In some embodiments, one or more therapeutically active anticancer agent includes, but is not limited to, paclitaxel, vinblastine, vincristine, etoposide, doxorubicin, herceptin, lapatinib, gefitinib, erlotinib, tamoxifen, fulvestrant, anastrazole, lectrozole, exemestane, fadrozole, cyclophosphamide, taxotere, melphalan, chlorambucil, mechlorethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin, C Bleomycin, combinations thereof, and the like.

Additionally, administration can comprise administering to the subject a plurality of dosages over a suitable period of time. Such administration regimens can be determined according to routine methods, upon a review of the instant disclosure.

Compound of formula (I), (IA), (IB), (II), (IIA), (III), (IIIA), and/or their subgenera, or Compound A, or a pharmaceutically acceptable salt, ester, solvate and/or prodrug thereof of the invention are generally administered in a dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. Time release preparations may be employed or the dose may be administered in as many divided doses as is convenient. When other methods are used (e.g. intravenous administration), the compound of formula (I), (IA), (IB), (II), (IIA), (III), (IIIA), and/or their subgenera, or Compound A, or a pharmaceutically acceptable salt, ester, solvate and/or prodrug thereof, are administered to the affected tissue at a rate from about 0.05 to about 10 mg/kg/hour, alternately from about 0.1 to about 1 mg/kg/hour. Such rates are easily maintained when the compound of formula (I), (IA), (IB), (II), (IIA), (III), (IIIA), and/or their subgenera, or Compound A, or a pharmaceutically acceptable salt, ester, solvate and/or prodrug thereof, are intravenously administered as discussed herein. Generally, topically administered formulations are administered in a dose of about 0.5 mg/kg/dose to about 10 mg/kg/dose range. Alternately, topical formulations are administered at a dose of about 1 mg/kg/dose to about 7.5 mg/kg/dose or even about 1 mg/kg/dose to about 5 mg/kg/dose.

A range of from about 0.1 to about 100 mg/kg is appropriate for a single dose. Continuous administration is appropriate in the range of about 0.05 to about 10 mg/kg.

Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) Cancer Chemother Rep. 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m$^2$.

A dosage form of the present invention may contain a compound of formula (I), (IA), (IB), (II), (IIA), (III), (IIIA), and/or their subgenera, or Compound A, or a pharmaceutically acceptable salt, ester, solvate and/or prodrug thereof, as disclosed herein, in an amount of about 5 mg to about 500 mg. That is, a dosage form of the present invention may contain Compound A in an amount of about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, or 500 mg.

A dosage form of the present invention may be administered, hourly, daily, weekly, or monthly. The dosage form of the present invention may be administered twice a day or once a day. The dosage form of the present invention may be administered with food or without food.

Insofar as the compound of formula (I), (IA), (IB), (II), (IIA), (III), (IIIA), and/or their subgenera, or Compound A, or a pharmaceutically acceptable salt, ester, solvate and/or prodrug thereof forms disclosed herein can take the form of a mimetic or fragment thereof, it is to be appreciated that the potency, and therefore dosage of an effective amount can vary. However, one skilled in the art can readily assess the potency of the compound of formula (I), (IA), (IB), (II), (IIA), (III), (IIIA), and/or their subgenera, or Compound A, or a pharmaceutically acceptable salt, ester, solvate and/or prodrug thereof of the type presently envisioned by the present application.

In settings of a gradually progressive disorder or condition characterized by cell proliferation, the compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent are generally administered on an ongoing basis. In certain settings administration of a compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent disclosed herein can commence prior to the development of disease symptoms as part of a strategy to delay or prevent the disease. In other settings the compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent disclosed herein is administered after the onset of disease symptoms as part of a strategy to slow or reverse the disease process and/or part of a strategy to improve cellular function and reduce symptoms.

It will be appreciated by one of skill in the art that dosage range will depend on the particular compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent, and its potency. The dosage range is understood to be large enough to produce the desired effect in which the neurodegenerative or other disorder and the symptoms associated therewith are ameliorated and/or survival of the cells is achieved, but not be so large as to cause unmanageable adverse side effects. It will be understood, however, that the specific dose level for any particular patient will depend on a variety of factors including the activity of the specific compound of formula (I), (IA), (IB), (II), (IIA), (III), (IIIA), and/or their subgenera, or Compound A, or a pharmaceutically acceptable salt, ester, solvate and/or prodrug thereof, employed; the age, body weight, general health, sex and diet of the individual being treated; the time and route of administration; the rate of excretion; other drugs which have previously been administered; and the severity of the particular disease undergoing therapy, as is well understood by those skilled in the art. The dosage can also be adjusted by the individual physician in the event of any complication. No unacceptable toxicological effects are expected when Compound A disclosed herein are used in accordance with the present application.

An effective amount of the compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent disclosed herein comprise amounts sufficient to produce a measurable biological response. Actual dosage levels of active ingredients of the present application can be varied so as to administer an amount of the compound of formula (I), (IA), (IB), (II), (IIA), (III), (IIIA), and/or their subgenera, or Compound A, or a pharmaceutically acceptable salt, ester, solvate and/or prodrug thereof and at least one additional therapeutically active agent that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

The following examples further illustrate the present invention but should not be construed as in any way limiting its scope.

EXAMPLES

Example 1: Anti-Proliferation Assay

Three human Lymphoma cell lines Toledo, MC116 and HT were purchased from the Bioresource Collection and Research Center (BCRC, Taiwan). All cells were incubated in a humidified atmosphere containing 5% $CO_2$ at 37° C.

CAL-101, also known as Idelalisib, is a PI3K-delta inhibitor with potential immunomodulating and antineoplastic activities. Anticancer activity of the combination of Compound A and CAL-101 on three human Lymphoma cell lines (Toledo, MC116, HT) was assessed using in vitro cell proliferation assay. Cell proliferation of drug-treated human cancer cells was determined at 96 hours post-treatment using the MTS (Promega) colorimetric assay. 50% inhibitory concentrations ($IC_{50}$) and 25% IC ($IC_{25}$) of a tested compound was calculated using GraphPad Prism software. The anti-proliferative effects of Compound A in single and combination treatments on three cell lines are shown in Tables 1-4.

Corrected absorbance values were obtained by subtracting the average 490 nm absorbance of the control wells (medium only, no cell) from all other absorbance values. Percentage inhibition of cell growth for compound treatment was calculated using this formula:

$$\% \text{ inhibition} = \left[1 - \frac{OD_{490} \text{ value in treated well}}{\text{Average } OD_{490} \text{ value in mock control well}}\right] \times 100$$

The sigmoidal dose-response curve is generated by fitting the percentage inhibition value as a function of logarithm of compound concentrations using GraphPad Prism software. $IC_{50}$ values are defined as the concentration needed for a 50% inhibition of cell growth. $IC_{25}$ values are defined as the concentration needed for a 25% inhibition of cell growth. All data represent the results of triplicate experiments.

Single Compound Treatment

The results indicated Compound A effectively inhibits cell proliferation of all three human Lymphoma cell lines, with $IC_{50}$ values ranging from 45.9 to 723.1 nM. Compound A exhibited the greatest inhibition effect on Toledo cell ($IC_{50}$ is 45.9 nM) and less potently on MC116 and HT cell ($IC_{50}$ is 723.1 and 525.5 nM, respectively). CAL-101 only exerts anti-proliferative effect against Toledo cell ($IC_{50}$ is 76.0 nM), and is insensitive to other two cell lines ($IC_{50}$ greater than 10 μM). The anti-proliferative effects of Compound A or CAL-101 were assessed and estimated $IC_{50}$ and $IC_{25}$ values are summarized in Table 1.

TABLE 1

Estimated $IC_{50}$ and $IC_{25}$ of the single drug treatment on 3 cell lines

|  |  | Compounds | |
| --- | --- | --- | --- |
| Cell Line (nM) |  | Compound A | CAL-101 |
| Toledo | $IC_{50}$ | 45.9 ± 2.3 | 76.0 ± 44.8 |
|  | $IC_{25}$ | 15.3 ± 0.8 | 25.3 ± 14.9 |
| MC116 | $IC_{50}$ | 723.1 ± 19.5 | 117860.0 ± 29613.6 |
|  | $IC_{25}$ | 241.0 ± 6.5 | 39286.7 ± 9871.2 |
| HT | $IC_{50}$ | 525.5 ± 19.9 | 10072.0 ± 1383.1 |
|  | $IC_{25}$ | 175.1 ± 6.6 | 3357.3 ± 461.0 |

Estimated $IC_{50}$ and $IC_{25}$ values were calculated based on non-linear regression of the dose-response curves of the cell proliferation ratio (%) as a function of logarithm of drug concentrations in single treatments.

Two-Compound Combination Treatment

The two-drug combination treatments on the cell proliferations were performed using three human Lymphoma cell lines (Toledo, MC116 and HT). CAL-101 was combined with Compound A at concentration close to their estimated $IC_{50}$ and $IC_{25}$. The anti-proliferative effects of Compound A in single and combination treatments on three cell lines are shown in Tables 2-4. As $IC_{25}$ value has shown, combination treatment with Compound A and CAL-101 synergistically enhanced anti-proliferative activity in MC116 and HT cells.

TABLE 2

Anti-Proliferative activity of Compound A in single and combination treatments on Toledo cell lines
Toledo cell

|  | Compounds | | |
| --- | --- | --- | --- |
|  | Compound A | CAL-101 | Compound A + CAL-101 |
| $IC_{50}$ conc. used (nM) | 50 | — | 50 |
|  | — | 400 | 400 |
| Inhibition* (%) | 25.6 ± 2.5 | 49.6 ± 1.7 | 66.0 ± 2.8 |

*Inhibition (%) showed the $IC_{50}$ value for proliferation inhibition in the Toledo cell.

TABLE 3

Anti-Proliferative activity of Compound A in single and combination treatments on MC116 cell lines
MC116 cell

|  | Compounds | | |
| --- | --- | --- | --- |
|  | Compound A | CAL-101 | Compound A + CAL-101 |
| $IC_{50}$ conc. used (nM) | 450 | — | 450 |
|  | — | 35000 | 35000 |
| Inhibition* (%) | 83.4 ± 1.2 | 70.4 ± 3.1 | 100.7 ± 1.4 |
| $IC_{25}$ conc. used (nM) | 150 | — | 150 |
|  | — | 17500 | 17500 |
| Inhibition* (%) | 44.3 ± 5.5 | 9.2 ± 3.4 | 88.0 ± 1.6 |

*Inhibition (%) showed the $IC_{50}$ value for proliferation inhibition in the MC116 cell.

TABLE 4

Anti-Proliferative activity of Compound A in single and combination treatments on HT cell lines
HT cell

|  | Compounds | | |
| --- | --- | --- | --- |
|  | Compound A | CAL-101 | Compound A + CAL-101 |
| $IC_{50}$ conc. used (nM) | 400 | — | 400 |
|  | — | 8000 | 8000 |
| Inhibition* (%) | 41.2 ± 1.9 | 37.6 ± 1.5 | 70.5 ± 1.8 |
| $IC_{25}$ conc. used (nM) | 133.3 | — | 133.3 |
|  | — | 2666.7 | 2666.7 |
| Inhibition* (%) | 15.2 ± 0.9 | 19.7 ± 4.3 | 51.5 ± 3.6 |

*Inhibition (%) showed the $IC_{50}$ value for proliferation inhibition in the HT cell.

Example 2: Analysis of Combination Assays

Combination interactions across the dose matrix were determined by the Loewe Additivity model using Horizon's Chalice™ Combination Analysis Software as outlined in the user manual: (http://chalice.horizondiscovery.com/chalice-portal/documentation/analyzer/home.jsp).

Synergy is determined by comparing the experimentally observed level of inhibition at each combination point with the value expected for additivity, which is derived from the single-agent responses along the edges of the matrix. Using Chalice™, potential synergistic interactions are visualized by plotting the calculated excess inhibition over expected, at each test point in the matrix, as a heat map, where brighter/warmer colours are indicative of higher activity levels.

The overall combination interactions can be scored using a simple volume score, which calculates the volume between the measured and the predicted response surface. This volume score shows whether the overall response to a combination is synergistic (positive values), antagonistic (negative values) or additive (values~0).

Drug Combination Study

The effect of combining Compound A with Olaparib was assessed in DLD1 Parental and DLD1-BRCA2 (−/−) isogenic cell lines across a matrix of concentrations using the Loewe Additivity model with Horizon's Chalice™ combination analysis software. The activity of the compounds was evaluated with short (48 hr) and long (6d, 144 hr) treatment time.

Using Chalice™, potential synergistic interactions were visualized by plotting the calculated excess inhibition over expected, at each test point in the matrix, as a heat map, where brighter/warmer colours are indicative of higher activity levels (FIGS. 1A-B and 2A-B).

Volume scores for this combination in both cell lines were positive, which further confirm that the interaction is synergistic (positive values) and (values~0). Volume and synergy scores for the combination in both lines are shown in FIGS. 1C-D and 2C-D and Table 5.

In Vivo Validation of PARP Inhibitor and Compound A Combination Treatment

In comparison with PARP inhibitor Olaparib alone treatment, combination treatment of Olaparib (50 mg/kg) and Compound A (50 mg/kg) significantly inhibited tumor growth of BRCA2-deficient triple-negative breast cancer (TNBC) patient-derived xenograft (PDX) model (FIGS. 3A-3B), confirming that the ability of Compound A to synergize with PARPi in vivo is associated with DNA repair pathways in tumors. In addition, we treated mice implanted with TNBC xenografts to Olaparib (50 mg, qd×28), followed by 2 subsequent doses of Compound A (50 mg qwk×2) followed by 7 subsequent doses of Olaparib (50 mg, qd×7) (FIGS. 3B-3C). A two-stage treatment system including Olaparib pre-treatment (FIG. 3B) or post treatment (FIG. 3C) demonstrated significant anti-tumor activity.

TABLE 5

Volume and synergy scores for the combination in DLD1 Parental and BRCA2 (−/−) isogenic cell lines
Loewe Volumes:

|  | 48 h | | 144 h | |
|---|---|---|---|---|
|  | Par | BRCA2 (−/−) | Par | BRCA2 (−/−) |
| CX-5461 × Olaparib | 1.34 | 1.32 | 0.828 | 1.81 |

Example 3: Anti-Proliferation Assay

BRCA1 negative (UWB1.289-2945) and BRCA1 positive (UWB1.289) human ovarian cancer cell lines were purchased from the American Type Culture Collection (ATCC). Those cell were incubated in a humidified atmosphere containing 5% $CO_2$ at 37° C.

The anticancer activity of Compound A on BRCA1 negative and BRCA1 positive human ovarian cancer cell lines were also assessed using in vitro cell proliferation assay. Cell proliferation of drug-treated human cancer cell was determined at 72 hours post-treatment using the CellTiter-Glo® Luminescent cell viability assay (Promega). $IC_{50}$ values are defined as the concentration needed for a 50% inhibition of cell growth and were calculated in GraphPad. The anti-proliferative effects of Compound A alone and in combination with cytokines on these two cell lines are shown in FIGS. 4-6.

Percentage inhibition of cell growth for compound treatment was calculated using this formula:

$$\% \text{ dead cells} = 100 - \left[ \frac{\text{luminescent value in treated well} \times 100}{\text{Average luminescent value in mock control well}} \right]$$

The data were processed using built-in excel-macro. Cell viability/proliferation was expressed as % dead cells with respect to the average signal from the untreated control wells of the respective plate. Out-liar values (of the triplicate) were rejected during QC. The processed data were plotted using Graphpad software. Statistical analysis was done using Excel (Microsoft) and Pair-wise comparison of two groups was made using the student's t test. All data represent the results of triplicate experiments.

As indicated in FIGS. 4 and B, the BRCA1 negative cell line (FIGS. 5A-B) is more sensitive to Compound A than BRCA1 positive cell line (FIGS. 4A-B). Compound A inhibited proliferation of BRCA1 negative human ovarian cancer cell lines with $IC_{50}$ values of around 2.34±1.67 nM to 3.78±2.24 nM. In BRCA1 positive ovarian cancer cell line UWB1.289, Compound A shows a dose dependent trend of cell toxicity. However, the maximum toxicity observed at the highest concentration (100 nM) does not exceed 40%. Therefore, $IC_{50}$ could not be calculated.

Early studies of CTLA-4 blockade demonstrated that in vivo treatment induces the expansion of memory CD8+ T-cell populations capable of producing intracellular cytokines. Here, two types of cytokines, TNF-α and IFN-γ, were used (0, 0.008, 0.04, 0.2, 1, 5 ng/mL) in response to together with Compound A.

Both cytokines, TNF-α and IFN-γ, by themselves show minimal, but increasing trend of cell toxicity with increasing dose on ovarian cancer cell lines. Combination drug assays were performed using BRCA1 negative and BRCA1 positive human ovarian cancer cell lines. In the presence of Compound A, these two cytokines, TNF-α and IFN-γ, show an additive effect on the cell toxicity on BRCA1 negative human ovarian cancer cells. The FIGS. 6A-6B shows the dose response curves of the effects of TNF-α and IFN-γ with various concentrations of Compound A on BRCA1 negative cells.

Example 4. Pharmaceutical Combination of Compound a and an Immunotherapeutic Agent Example 3 shows that in the presence of Compound A, cytokines TNF-α and IFN-γ have an additive cytotoxic effect on BRCA1 negative human ovarian cancer cells in a dose-dependent manner. Accordingly, the addition of another agent that increases or induces the production of endogenous cytokines in cancer cells should also assist in cancer cell toxicity.

One embodiment of the present invention may thus be a pharmaceutical combination comprising a compound of the present invention, such as Compound A, and an immunotherapeutic agent, such as an agent that can induce the production of endogenous cytotoxic cytokines (e.g., TNF-α and IFN-γ). Such a pharmaceutical combination should have a greater effect in treating or ameliorating cell proliferation disorder. Again, without wishing to be bound by any particular theory, we believe an immunotherapeutic agent can increases the local production of one or more cytokines that have cytotoxic effect on tumor cells, such as tumor necrosis factor α (TNF-α) and Interferon gamma (IFN-γ). Meanwhile, a chemical compound described herein, such as Compound A, can enhance the cytotoxic effect of TNF-α and/or IFN-γ, thus the combination can achieve greater therapeutic effect.

Indeed, an anti-PD-1 antibody is capable of enhancing T-cell responses and cytokine production in vitro. For example, Wang et al. (Cancer Immuno Res 2(9): 846-856, incorporated by reference in its entirety) demonstrated that in an allogeneic mixed lymphocyte reaction assay, PD-1 blockade with nivolumab (BMS-936558) systematically resulted in a titratable enhancement of IFN-γ release, and in some donor T-cell/DC pairs, enhanced T-cell proliferation was observed. (FIG. 7, adopted from Wang et al.). Using a CMV-restimulation assay, Wang et al. also showed that nivolumab resulted in a concentration-dependent augmentation of IFN-γ secretion from CMV-responsive donors.

Our results in Example 3 already demonstrated that TNF-α and IFN-γ show an additive effect on the cell toxicity on BRCA1 negative human ovarian cancer cells in the presence of Compound A. Particularly, FIGS. 6A-6B show that Compound A can enhance the cytotoxic effect of TNF-α and IFN-γ in a dose dependent manner. Therefore, a pharmaceutical combination comprising a compound of the present invention, such as Compound A, and an immunotherapeutic agent, such as an agent that can induce the production of endogenous cytotoxic cytokines (e.g., TNF-α and IFN-γ) should produce a greater efficiency in killing tumor cells.

The capability of a chemical compound of the present invention, such as Compound A, in increasing production of chemokines in tumor cells was also investigated. Chemokines are molecules produced by tumor cells which attract immune cells such as effector T-cells. Chemokines and chemokine receptors play a key role along tumor immunogenicity, since they not only comprise the main regulatory system leading leukocyte infiltration in primary tumors, but also intervene in cancer cells proliferation and in metastasis guidance. Cancer cells, stromal cells, and infiltrated immune cells can secrete chemokines. Cancer cells themselves can also express chemokine receptors and respond to these chemokines. This forms a complex chemokine network that influences tumor cell growth, survival, migration, and angiogenesis, as well as immune cell infiltration.

Compound A was applied to both HBCx-39 (BRCA2 wild type) and HBCx-17 (BRCA2 mutant) cancer cell lines in vitro. HBCx-17 is a homologous recombination deficiency tumor cell line having BRCA2 mutation. Surprisingly, our results demonstrated that Compound A is capable of inducing the production of several important chemokines in tumor cells (FIGS. 8A to 8C). In addition, Compound A treatment increased more CCL9. CCL21 and CXCL9 mRNA expression in cancer cells having BRCA2 mutant compared to wild type cancer cells. The results further proved that a pharmaceutical combination comprising a compound of the present invention, such as Compound A, and an immunotherapeutic agent, such as an agent that can induce the production of endogenous cytotoxic cytokines (e.g., TNF-α and IFN-γ), would have greater efficiency in treating cancer, because the chemokines induced by Compound A attract immune cells, such as dendritic cells (DCs), activated effector T-cells (e.g., CD8+ lymphocytes), and/or natural killer (NK) cells to tumor cells, and result in destruction of the tumor cells.

The dual functions of a pharmaceutical combination of the present invention as explained herein indicate that such pharmaceutical combination is surprisingly effective in treating cancers.

Example 5. Pharmaceutical Combination of Compound a and an Anti-PD-1 Antibody

Both in vitro and in vivo experiments are conducted to test the pharmaceutical combination comprising Compound A and an anti-PD-1 antibody, nivolumab, in treating cancers, such as leukemia, lymphoma, myeloma, multiple myeloma, breast cancer, ovarian cancer, pancreatic cancer, prostate cancer, lung cancer, Ewing's sarcoma, head and neck cancer, heme cancer, colorectum cancer, cervical cancer, liver cancer, cancer of the lymph nodes, colon cancer, prostate cancer, brain cancer, cancer of the head and neck, bone cancer, skin cancer, kidney cancer, and cancer of the heart. In some tests, the cancer is a homologous recombination (HR) dependent double strand break (DSB) repair deficient cancer or non-homologous end joining (NHEJ) DSB repair deficient cancer.

Compound A and nivolumab are co-administered either in vitro or in vivo to applicable cancer cell lines or patients, with the treatment of Compound A alone and treatment of the anti-PD-1 antibody alone as controls. The results indicate that the pharmaceutical combination shows a synergistic effect in treating cancers when compared to Compound A alone and the anti-PD-1 antibody treatment alone.

The patents and publications listed herein describe the general skill in the art and are hereby incorporated by reference in their entireties for all purposes and to the same extent as if each was specifically and individually indicated to be incorporated by reference. Nothing herein is to be construed as an admission that the present invention is not entitled to antedate such publication by virtue of prior invention. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. Many modifications and other embodiments of the inventions set forth herein will come to mind to one skilled in the art to which these inventions pertain having the benefit of the teachings presented in the foregoing descriptions and the associated drawings. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A pharmaceutical combination comprising a therapeutically effective amount of Compound A:

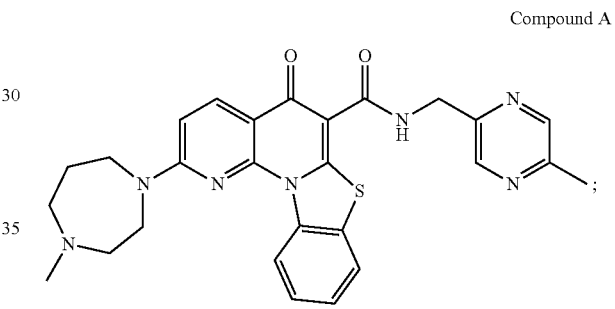

Compound A or a pharmaceutically acceptable salt, ester, solvate and/or prodrug thereof; and at least one anti-PD-1 antibody.

2. The pharmaceutical combination of claim 1, wherein Compound A and at least one anti-PD-1 antibody are in single dosage form or in separate dosage forms.

3. The pharmaceutical combination of claim 2, wherein the separate dosage forms are administered via same mode of administration or different modes of administration.

4. The pharmaceutical combination of claim 3, wherein the separate dosage forms are co-administered via simultaneous administration, sequential administration, overlapping administration, interval administration, continuous administration, or a combination thereof.

5. The pharmaceutical combination of claim 1, wherein the at least one anti-PD-1 antibody disrupts the interaction between Programmed Death-1 (PD-1) and Programmed Death Ligand-1 (PD-L1).

6. The pharmaceutical combination of claim 1, wherein the anti-PD-1 antibody is a monoclonal antibody.

7. The pharmaceutical combination of claim 1, wherein the anti-PD-1 antibody is a humanized antibody.

8. The pharmaceutical combination of claim 1, wherein the anti-PD-1 antibody is selected from one or more of the group consisting of nivolumab, lambrolizumab, pidilizumab, pembrolizumab, and clone RPM1-14.

9. The pharmaceutical combination of claim 8, wherein the monoclonal antibody is selected from the group consisting of nivolumab and pembrolizumab.

10. The pharmaceutical combination of claim 1, which is a pharmaceutical formulation further comprising a pharmaceutically acceptable excipient or a pharmaceutically acceptable carrier.

11. The pharmaceutical combination of claim 1 wherein Compound A is present in an amount from about 1 mg to about 500 mg.

12. The pharmaceutical combination of claim 1, wherein the anti-PD-1 antibody is nivolumab.

* * * * *

UNITED STATES PATENT AND TRADEMARK OFFICE
CERTIFICATE OF CORRECTION

PATENT NO. : 10,857,156 B2
APPLICATION NO. : 15/347656
DATED : December 8, 2020
INVENTOR(S) : John Soong Page 1 of 1

It is certified that error appears in the above-identified patent and that said Letters Patent is hereby corrected as shown below:

In the Claims

In Claim 8, Column 56, Line 64, please replace:
"pembrolizumab, and clone RPM1-14"
With:
--pembrolizumab, AMP-224, and clone RPM1-14--.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*